US012258613B2

United States Patent
Heath et al.

(10) Patent No.: US 12,258,613 B2
(45) Date of Patent: Mar. 25, 2025

(54) PAIRING ANTIGEN SPECIFICITY OF A T CELL WITH T CELL RECEPTOR SEQUENCES

(71) Applicant: CALIFORNIA INSTITUTE OF TECHNOLOGY, Pasadena, CA (US)

(72) Inventors: James R. Heath, Pasadena, CA (US); Songming Peng, San Mateo, CA (US); Alphonsus Hon-Chung Ng, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 1265 days.

(21) Appl. No.: 16/492,588

(22) PCT Filed: Mar. 8, 2018

(86) PCT No.: PCT/US2018/021611
§ 371 (c)(1),
(2) Date: Sep. 9, 2019

(87) PCT Pub. No.: WO2018/165475
PCT Pub. Date: Sep. 13, 2018

(65) Prior Publication Data
US 2023/0069843 A1    Mar. 9, 2023

Related U.S. Application Data

(60) Provisional application No. 62/468,448, filed on Mar. 8, 2017.

(51) Int. Cl.
*C12Q 1/6804* (2018.01)
*B01L 3/00* (2006.01)
*C12N 15/10* (2006.01)

(52) U.S. Cl.
CPC ...... *C12Q 1/6804* (2013.01); *B01L 3/502761* (2013.01); *C12N 15/1037* (2013.01);
(Continued)

(58) Field of Classification Search
CPC ............ C12N 15/1037; C12N 15/1065; C12N 15/1055; B01L 3/502761; B01L 2200/0652; B01L 2300/0864; B01L 2400/02
(Continued)

(56) References Cited

U.S. PATENT DOCUMENTS

| 4,818,680 A | 4/1989 | Collins et al. |
| 6,037,167 A | 3/2000 | Adelman et al. |

(Continued)

FOREIGN PATENT DOCUMENTS

| AU | 2007100888 A4 | 11/2007 |
| AU | 2010202492 A1 | 7/2010 |

(Continued)

OTHER PUBLICATIONS

Bentzen et al. Large-scale detection of antigen-specific T cells using peptide-MHC-I multimers labeled with DNA barcodes. Nature Biotechnology. 34(10), 2016, 1037-1045. (Year: 2016).*

(Continued)

*Primary Examiner* — Aaron A Priest
*Assistant Examiner* — Randi Lynn Beil
(74) *Attorney, Agent, or Firm* — KNOBBE, MARTENS, OLSON & BEAR, LLP

(57) ABSTRACT

Compositions and methods for identifying antigen-specific T cells, including determining paired T cell receptor sequences for a specific antigen, are described. Compositions and methods for identifying neoantigen-specific T cells
(Continued)

are also described. Microfluidic devices useful for identifying antigen-specific T cells, and methods of using the same, are also described.

161 Claims, 15 Drawing Sheets

Specification includes a Sequence Listing.

(52) U.S. Cl.
CPC ..... *C12N 15/1055* (2013.01); *C12N 15/1065* (2013.01); *B01L 2200/0652* (2013.01); *B01L 2300/0864* (2013.01); *B01L 2400/02* (2013.01)

(58) Field of Classification Search
USPC .......................................................... 506/9
See application file for complete search history.

(56) References Cited

U.S. PATENT DOCUMENTS

| | | | |
|---|---|---|---|
| 6,100,079 A | 8/2000 | Tajima | |
| 6,387,622 B1 | 5/2002 | Siiman et al. | |
| 6,649,378 B1 | 11/2003 | Kozwich et al. | |
| 6,730,269 B2 | 5/2004 | Mirkin et al. | |
| 6,861,221 B2 | 3/2005 | Mirkin et al. | |
| 6,969,761 B2 | 11/2005 | Mirkin et al. | |
| 6,974,669 B2 | 12/2005 | Mirkin et al. | |
| 7,094,555 B2 | 8/2006 | Kwok et al. | |
| 7,098,320 B1 | 8/2006 | Mirkin et al. | |
| 7,147,687 B2 | 12/2006 | Mirkin et al. | |
| 7,169,556 B2 | 1/2007 | Park et al. | |
| 7,186,814 B2 | 3/2007 | Garimella et al. | |
| 7,208,587 B2 | 4/2007 | Mirkin et al. | |
| 7,250,499 B2 | 7/2007 | Mirkin et al. | |
| 7,259,252 B2 | 8/2007 | Mirkin et al. | |
| 7,323,309 B2 | 1/2008 | Mirkin et al. | |
| 7,381,529 B2 | 6/2008 | Yamakawa et al. | |
| 7,531,726 B2 | 5/2009 | Chan et al. | |
| 7,625,702 B2 | 12/2009 | Cha | |
| 7,807,372 B2 | 10/2010 | Mirkin et al. | |
| 8,323,888 B2 | 12/2012 | Mirkin et al. | |
| 8,354,231 B2 | 1/2013 | Kwong et al. | |
| 8,394,590 B2 | 3/2013 | Kwong et al. | |
| 8,617,884 B2 | 12/2013 | Berenson et al. | |
| 8,709,722 B2 | 4/2014 | Tan et al. | |
| 8,993,714 B2 | 3/2015 | Salemme et al. | |
| 8,999,263 B2 | 4/2015 | Peterman et al. | |
| 9,011,774 B2 | 4/2015 | Kim et al. | |
| 9,023,650 B2 | 5/2015 | Farquar et al. | |
| 9,173,840 B2 | 11/2015 | Amiji et al. | |
| 10,481,158 B2 | 11/2019 | Heath et al. | |
| 2002/0168663 A1 | 11/2002 | Phan et al. | |
| 2003/0027234 A1 | 2/2003 | Murugan et al. | |
| 2003/0219752 A1 | 11/2003 | Short | |
| 2003/0223938 A1 | 12/2003 | Nagy et al. | |
| 2004/0072231 A1 | 4/2004 | Mirkin et al. | |
| 2004/0102369 A1 | 5/2004 | Wu et al. | |
| 2004/0137642 A1 | 7/2004 | Erfle et al. | |
| 2005/0019843 A1 | 1/2005 | Chen et al. | |
| 2005/0048546 A1 | 3/2005 | Penn et al. | |
| 2005/0287611 A1 | 12/2005 | Thomas, IV et al. | |
| 2006/0014172 A1 | 1/2006 | Muller et al. | |
| 2006/0040286 A1 | 2/2006 | Mirkin et al. | |
| 2006/0240416 A1 | 10/2006 | Banerjee et al. | |
| 2007/0264652 A1 | 11/2007 | Upadhyay et al. | |
| 2008/0188374 A1 | 8/2008 | Chen et al. | |
| 2008/0220982 A1 | 9/2008 | Vu | |
| 2009/0017455 A1 | 1/2009 | Kwong et al. | |
| 2009/0036324 A1 | 2/2009 | Fan et al. | |
| 2010/0004138 A1 | 1/2010 | Sato et al. | |
| 2011/0039717 A1 | 2/2011 | Kwong et al. | |
| 2011/0166034 A1 | 7/2011 | Kwona et al. | |
| 2011/0171749 A1 | 7/2011 | Alocilja et al. | |
| 2011/0237449 A1 | 9/2011 | McMaster et al. | |
| 2012/0121649 A1 | 5/2012 | Santamaria | |
| 2012/0157329 A1 | 6/2012 | Castellano et al. | |
| 2012/0276109 A1 | 11/2012 | Fraser et al. | |
| 2013/0130364 A1 | 5/2013 | Seo et al. | |
| 2013/0260447 A1* | 10/2013 | Link ................. C12Q 1/686 435/283.1 |
| 2013/0330414 A1 | 12/2013 | Santamaria | |
| 2014/0272972 A1 | 9/2014 | Lee | |
| 2015/0044672 A1 | 2/2015 | Stojanovic et al. | |
| 2015/0050747 A1 | 2/2015 | Alocilja et al. | |
| 2015/0051089 A1 | 2/2015 | Robins et al. | |
| 2015/0132758 A1 | 5/2015 | Medina-Llamas et al. | |
| 2015/0157737 A1 | 6/2015 | Gu et al. | |
| 2015/0166997 A1 | 6/2015 | Messmer | |
| 2015/0290611 A1 | 10/2015 | Pine et al. | |
| 2015/0322494 A1 | 11/2015 | Garcia et al. | |
| 2016/0271237 A1 | 9/2016 | Santamaria | |
| 2016/0282255 A1 | 9/2016 | Irimia et al. | |
| 2016/0287152 A1 | 10/2016 | Schwartz et al. | |

FOREIGN PATENT DOCUMENTS

| | | |
|---|---|---|
| AU | 2016203838 A1 | 6/2016 |
| CN | 1464070 A | 12/2003 |
| CN | 101684503 A | 3/2010 |
| CN | 101852808 A | 10/2010 |
| CN | 102072931 A | 5/2011 |
| CN | 102147414 A | 8/2011 |
| CN | 102168066 A | 8/2011 |
| CN | 102234682 A | 11/2011 |
| CN | 102321762 A | 1/2012 |
| CN | 103266170 A | 8/2013 |
| CN | 103276087 A | 9/2013 |
| CN | 103333967 A | 10/2013 |
| CN | 104962570 A | 10/2015 |
| CN | 105648069 A | 6/2016 |
| CN | 105651992 A | 6/2016 |
| CN | 105755118 A | 7/2016 |
| DE | 102008013715 | 4/2010 |
| EP | 1328540 B1 | 3/2005 |
| EP | 0837946 B1 | 3/2009 |
| EP | 1747295 B1 | 1/2012 |
| EP | 2842570 A1 | 3/2015 |
| JP | 2004354164 A | 12/2004 |
| JP | 2006158276 A | 6/2006 |
| JP | 2006328032 A | 12/2006 |
| JP | 2007262114 A | 10/2007 |
| JP | 2009068869 A | 4/2009 |
| JP | 2013092501 A | 5/2013 |
| JP | 2014514331 A | 6/2014 |
| JP | 2015173626 A | 10/2015 |
| KR | 100823684 B1 | 4/2008 |
| KR | 20110133843 A | 12/2011 |
| KR | 20130114932 A | 4/2012 |
| KR | 20130121550 A | 11/2013 |
| KR | 20140097679 A | 8/2014 |
| KR | 20150049697 A | 5/2015 |
| KR | 20150144644 A | 12/2015 |
| WO | WO1991017265 | 11/1991 |
| WO | WO1992007952 | 5/1992 |
| WO | WO1993025660 | 12/1993 |
| WO | WO1995005399 | 2/1995 |
| WO | WO1999002728 | 1/1999 |
| WO | WO2000028088 | 5/2000 |
| WO | WO2000040750 | 7/2000 |
| WO | WO2001096023 | 12/2001 |
| WO | WO2002031501 | 4/2002 |
| WO | WO2002083292 | 10/2002 |
| WO | WO2003035829 | 5/2003 |
| WO | WO2004003142 | 1/2004 |
| WO | WO2004015395 | 2/2004 |
| WO | WO2004033497 | 4/2004 |
| WO | WO2004053163 | 6/2004 |
| WO | WO2004067742 | 8/2004 |
| WO | WO2004106546 | 12/2004 |
| WO | WO2005001113 | 1/2005 |
| WO | WO2005021800 | 3/2005 |
| WO | WO2005108612 | 11/2005 |
| WO | WO2005111624 | 11/2005 |

(56) References Cited

FOREIGN PATENT DOCUMENTS

| | | |
|---|---|---|
| WO | WO2006031883 | 3/2006 |
| WO | WO2006076793 | 7/2006 |
| WO | WO 2007/014267 | 2/2007 |
| WO | WO2007024676 | 3/2007 |
| WO | WO2007024840 | 3/2007 |
| WO | WO2007133807 | 11/2007 |
| WO | WO2008001376 | 1/2008 |
| WO | WO2008016680 | 2/2008 |
| WO | WO2008017507 | 2/2008 |
| WO | WO2008030071 | 3/2008 |
| WO | WO2008090557 | 7/2008 |
| WO | WO2008091364 | 7/2008 |
| WO | WO2008157649 | 12/2008 |
| WO | WO2009003492 | 1/2009 |
| WO | WO2009055068 | 4/2009 |
| WO | WO2009083856 | 7/2009 |
| WO | WO2009106322 | 9/2009 |
| WO | WO2009124296 | 10/2009 |
| WO | WO2009149091 | 12/2009 |
| WO | WO 2010/037395 | 4/2010 |
| WO | WO2010037397 | 4/2010 |
| WO | WO2011090445 | 7/2011 |
| WO | WO2011100669 | 8/2011 |
| WO | WO2011104497 | 9/2011 |
| WO | WO 2012/044999 | 4/2012 |
| WO | WO2012062904 | 5/2012 |
| WO | WO2012111685 | 8/2012 |
| WO | WO2012111686 | 8/2012 |
| WO | WO2012111687 | 8/2012 |
| WO | WO2012148960 | 11/2012 |
| WO | WO2013071520 | 5/2013 |
| WO | WO2013119793 | 8/2013 |
| WO | WO2014124543 | 8/2014 |
| WO | WO2014144892 | 9/2014 |
| WO | WO2014189257 | 11/2014 |
| WO | WO2014192937 | 12/2014 |
| WO | WO2014197840 | 12/2014 |
| WO | WO2015060417 | 4/2015 |
| WO | WO2015100373 | 7/2015 |
| WO | WO2015135856 | 9/2015 |
| WO | WO2015161173 | 10/2015 |
| WO | WO2015174862 | 11/2015 |
| WO | WO2015200384 | 12/2015 |
| WO | WO2016015027 | 1/2016 |
| WO | WO2016075172 | 5/2016 |
| WO | WO2016090115 | 6/2016 |
| WO | WO2016115500 | 7/2016 |
| WO | WO2016127158 | 8/2016 |
| WO | WO2016160908 | 10/2016 |
| WO | WO 2016/196691 | 12/2016 |
| WO | WO-2016196691 A2 * 12/2016 ............. C07H 21/04 |
| WO | WO-2018057051 A1 * 3/2018 ......... C12N 15/1065 |
| WO | WO 2018/165475 | 9/2018 |

OTHER PUBLICATIONS

Bakker, Arnold H. et al.; "Conditional MHC class I ligands and peptide exchange technology for the human MHC gene products HLA-A1, -A3, -A11, and -87"; PNAS; Mar. 11, 2008; vol. 105; No. 10; pp. 3825-3830.

Coulie, Pierre G. et al.; "Tumour antigens recognized by T lymphocytes: at the core of cancer immunotherapy"; Nature Reviews Cancer; vol. 14; Feb. 2014; pp. 135-146.

Extended European Search Report, European Application No. 16804369. 3, Dec. 13, 2018, 10 pages.

Fritsch, Edward F. et al.; "HLA-binding properties of tumor neoepitopes in humans"; Cancer Immunol Res.; Jun. 2014; 2(6); pp. 522-529.

International Search Report and Written Opinion mailed Nov. 29, 2016 in corresponding International Application No. PCT/US2016/035357, 10pp.

International Search Report and Written Opinion mailed Aug. 3, 2018 in corresponding International Application No. PCT/US2018/021611, 10pp.

Kwong, Gabriel A. et al.; "Modular nucleic acid assembled p/MHC microarrays for multiplexed sorting of antigen-specific T cells"; J Am Chem Soc.; Jul. 22, 2009; 131(28); pp. 9695-9703.

Novak, Erik J. et al.; "MHC class II tetramers identify peptide-specific human CD4+ T cells proliferating in response to influenza A antigen"; J Clin Invest.; Dec. 5, 1999; 104(12); pp. R63-R67.

Rodenko, Boris et al.; "Generation of peptide-MHC class I complexes through UV-mediated ligand exchange"; Nature Protocols; vol. 1; No. 3; 2006; pp. 1120-1132.

Sano, Takeshi et al.; "Expression of a cloned streptavidin gene in *Escherichia coli*"; Proc Natl Acad Sci USA; Jan. 1990; 87(1); pp. 142-146.

Stoeva, S.I. et al., "Multiplexed Detection of Protein Cancer Markers with Biobarcoded Nanoparticle Probes," Journal of the American Chemical Society, Jul. 5, 2006, vol. 128, No. 26, pp. 8378-8379.

Stone, D.J. et al., "HLA-restricted epitope identification and detection of functional Tcell responses by using MHC-peptide and costimulatory microarrays," Proceedings of the National Academy of Sciences of the United States of America, Mar. 8, 2005, vol. 102, No. 10, pp. 3744-3749.

Toebes, Mireille et al.; "Design and use of conditional MHC class I ligands"; Nature Medicine; vol. 12; No. 2; Feb. 2006; pp. 246-251.

Andersen, Rikke Sick et al.; "Parallel detection of antigen-specific T cell responses by combinatorial encoding of MHC multimers"; Nature Protocols; vol. 7; No. 5; 2012; pp. 891-902.

File History of U.S. Appl. No. 15/170,919, filed Jun. 1, 2016 in 478 pages.

File History of U.S. Appl. No. 16/347,559, filed May 3, 2019 in 775 pages.

International Search Report and Written Opinion mailed Mar. 6, 2018 in International Application No. PCT/US2017/059598, in 15 pages.

* cited by examiner

SEQUENCE LISTING

```
<160> NUMBER OF SEQ ID NOS: 174

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: (S)-3-(Fmoc-amino)-3-(2-nitrophenyl)propionic
      acid

<400> SEQUENCE: 1

Lys Ile Leu Gly Phe Val Phe Xaa Val
1               5

<210> SEQ ID NO 2
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 2
aaaaaaaaaa taggcatccc gaggattcag                                          30

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcgtcggcag cgtcagatgt gtataagaga cag                                      33

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tctctcagct ggtacacggc                                                     20

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gatggctcaa acacagcgac ctc                                                 23

<210> SEQ ID NO 6
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(41)
<223> OTHER INFORMATION: a, c, t, g, unknown or other

<400> SEQUENCE: 6
tcgtcggcag cgtcagatgt gtataagaga cagnnnnnnn ncgagtctct ctcagctggt         60
acacggc                                                                   67

<210> SEQ ID NO 7
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(41)
<223> OTHER INFORMATION: a, c, t, g, unknown or other

<400> SEQUENCE: 7
```

```
tcgtcggcag cgtcagatgt gtataagaga cagnnnnnnn ncgagtcgat ggctcaaaca    60
cagcgacctc                                                            70
```

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ctgaatcctc gggatgccta                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
taggcatccc gaggattcag                                                 20

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Leu Leu Met Trp Ile Thr Gln Val
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Leu Val Pro Met Val Ala Thr Val
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: (S)-3-(Fmoc-amino)-3-(2-nitrophenyl)propionic
      acid

<400> SEQUENCE: 12

Lys Ile Leu Gly Phe Val Phe Xaa Val
1               5
```

```
<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu Leu Ala Gly Ile Gly Ile Leu Thr Val
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Leu Cys Thr Leu Val Ala Met Leu
1               5

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Ala Ser Ser Thr Val Ser Gly Ala Pro Ser Glu Gln Phe Phe
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Ala Leu Tyr Phe Phe Phe Gly Asn Glu Lys Leu Thr Phe
1               5                   10

<210> SEQ ID NO 17
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(41)
<223> OTHER INFORMATION: a, c, t, g, unknown or other

<400> SEQUENCE: 17
tcgtcggcag cgtcagatgt gtataagaga cagnnnnnnn nactcttgat ggctcaaaca     60
cagcgacctc                                                           70

<210> SEQ ID NO 18
<211> LENGTH: 67
<212> TYPE: DNA
<213> ORGANISM: Artificial Sequence
```

<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(41)
<223> OTHER INFORMATION: a, c, t, g, unknown or other

<400> SEQUENCE: 18
tcgtcggcag cgtcagatgt gtataagaga cagnnnnnnnn nactctttct ctcagctggt      60
acacggc                                                                67

<210> SEQ ID NO 19
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(41)
<223> OTHER INFORMATION: a, c, t, g, unknown or other

<400> SEQUENCE: 19
tcgtcggcag cgtcagatgt gtataagaga cagnnnnnnnn ncgagtctct ctcagctggt      60
acacggc                                                                67

<210> SEQ ID NO 20
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(41)
<223> OTHER INFORMATION: a, c, t, g, unknown or other

<400> SEQUENCE: 20
tcgtcggcag cgtcagatgt gtataagaga cagnnnnnnnn ncgagtcgat ggctcaaaca      60
cagcgacctc                                                             70

<210> SEQ ID NO 21
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(41)
<223> OTHER INFORMATION: a, c, t, g, unknown or other

<400> SEQUENCE: 21
tcgtcggcag cgtcagatgt gtataagaga cagnnnnnnnn ntagacgtct ctcagctggt      60
acacggc                                                                67

<210> SEQ ID NO 22
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<221> NAME/KEY: modified_base
<222> LOCATION: (34)..(41)
<223> OTHER INFORMATION: a, c, t, g, unknown or other

<400> SEQUENCE: 22
tcgtcggcag cgtcagatgt gtataagaga cagnnnnnnn ntagacggat ggctcaaaca    60
cagcgacctc                                                          70

<210> SEQ ID NO 23
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(41)
<223> OTHER INFORMATION: a, c, t, g, unknown or other

<400> SEQUENCE: 23
tcgtcggcag cgtcagatgt gtataagaga cagnnnnnnn nttcaggtct ctcagctggt    60
acacggc                                                             67

<210> SEQ ID NO 24
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(41)
<223> OTHER INFORMATION: a, c, t, g, unknown or other

<400> SEQUENCE: 24
tcgtcggcag cgtcagatgt gtataagaga cagnnnnnnn nttcagggat ggctcaaaca    60
cagcgacctc                                                          70

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Gln Gly Asn Leu Ile Phe
1               5

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Cys Ala Val Glu Tyr Gly Asn Gln Phe Tyr Phe
1               5                   10

<210> SEQ ID NO 27
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ile Met Glu Glu Ala Lys Glu
1               5

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Ala Ser Ser Thr Gly Ala Gly Ala Pro Ser Glu Gln Phe Val
1               5                   10                  15

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Ile Val Arg Val Ala Ser Ser Gly Gly Ala Thr Asn Lys Leu Ile
1               5                   10                  15

Phe

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Ala Tyr Arg Ser Ala Leu Asn Asp Lys Ile Ile Phe
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Ala Leu Tyr Phe Phe Phe
1               5

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 32

Cys Ala Ser Ser Thr Val Ser Gly Ala Pro Ser Glu Gln Gly Val
1               5                   10                  15

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Cys Ala Ser Ser Phe Ser Pro Pro Asp Gly Ile Ser Tyr Glu Gln Tyr
1               5                   10                  15

Phe

<210> SEQ ID NO 34
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Leu Val Gly Asp Gly Asn Gln Ala Gly Thr Ala Leu Ile Phe
1               5                   10                  15

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Gly Asn Leu Ile Phe
1               5

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Ala Ser Ser Thr Val Ser Gly Ala Pro Ser Glu Gln Gly Val
1               5                   10                  15

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Cys Val Val Val
1

<210> SEQ ID NO 38
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Cys Ala His Thr Ala Ser Gly Thr Tyr Lys Tyr Ile Phe
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Cys Ala Ala Gln Asp Arg Gly Ser Glu Gln Phe Phe
1               5                   10

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Ile Val Arg Asp Arg Met Asp Ser Asn Tyr Gln Leu Ile Trp
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Ala Ser Ser Trp Val Ala Gly Glu Gly Ser Glu Gln Phe Phe
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Val Val Ser Ala Gly Gly Thr Ser Tyr Gly Lys Leu Thr Phe
1               5                   10                  15

<210> SEQ ID NO 43
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
```

```
aaaaaaaaac tatgtcgata caagtcagat agttcaactc gttcactata actgaatcct    60
cgggatgcct a                                                         71
```

<210> SEQ ID NO 44
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

```
tacaggaagc ctcagca                                                   17
```

<210> SEQ ID NO 45
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

```
caggagggct cggca                                                     15
```

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

```
ggacaaagcc ttgagcagcc ctc                                            23
```

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

```
ggacaaaaca ttgaccagcc cactg                                          25
```

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

```
aaggaccaag tgtttcagcc ttccac                                         26
```

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gctcagtcag tggctcagcc gga                                              23

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cttgctaaga ccacccagcc catc                                             24

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggagaggatg tggagcagag tcttttcc                                         28

<210> SEQ ID NO 52
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
agccaaaaga tagaacagaa ttccgaggc                                        29

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaggccctga acattcagga ggg                                              23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gaaaaccagg tggagcacag ccc                                              23

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gcccagtctg tgagccagca taacc                                          25

<210> SEQ ID NO 56
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gcccagtcgg tgacccagct tg                                             22

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gcccagtcgg tgacccagct tag                                            23

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcccagtcag tgacccagcc tg                                             22

<210> SEQ ID NO 59
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctcttctggt atgtgcaata ccccaacc                                       28

<210> SEQ ID NO 60
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gttgaaccat atctcttctg gtatgtgcaa tacc                                34

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gcccagtctg tgacccagct tgac                                           24

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
acccagtcgg tgacccagct tg                                              22

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggagattcag tggtccagac agaaggc                                         27

<210> SEQ ID NO 64
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggaaattcag tgacccagat ggaagg                                          26

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ggagattcag tgacccagat ggaagg                                          26

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
aaaaaccaag tggagcagag tcctcagtc                                       29

<210> SEQ ID NO 67
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ctacatacac tggagcagag tccttcattc c                                    31

```
<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cggaaggagg tggagcagga tcc                                          23

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cagaaggagg tggagcagaa ttctgg                                       26

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggacccctca gtgttccaga ggg                                          23

<210> SEQ ID NO 71
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cagaaggagg tggagcagga tcctg                                        25

<210> SEQ ID NO 72
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ggagagaatg tggagcagca tccttc                                       26

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ggagagagtg tggggctgca tcttc                                        25
```

```
<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcccagaaga taactcaaac ccaaccag                                      28

<210> SEQ ID NO 75
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cagaagataa ctcaaaccca accaggaatg                                    30

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcccagagag tgactcagcc cga                                           23

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
agtcaacagg gagaagagga tcctcagg                                      28

<210> SEQ ID NO 78
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ggagactcgg ttacccagac agaagg                                        26

<210> SEQ ID NO 79
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gctcagaagg taactcaagc gcagactg                                      28

<210> SEQ ID NO 80
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gaagaccagg tgacgcagag tccc                                           24

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
aaacaggagg tgacgcagat tcctgc                                         26

<210> SEQ ID NO 82
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ggaatacaag tggagcagag tcctccag                                       28

<210> SEQ ID NO 83
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cagcagcagg tgaaacaaag tcctca                                         26

<210> SEQ ID NO 84
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cagcaggtga acaaagtcc tcaatctttg                                      30

<210> SEQ ID NO 85
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
atactgaacg tggaacaaag tcctcagtca c                                   31

<210> SEQ ID NO 86
<211> LENGTH: 31
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ggacaacagg taatgcaaat tcctcagtac c                                    31

<210> SEQ ID NO 87
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gatgctaaga ccacccagcc ccc                                             23

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gatgctaaga ccacccagcc cacc                                            24

<210> SEQ ID NO 89
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gatgctaaga ccacacagcc aaattcaatg                                      30

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
acccagctgc tggagcagag cc                                              22

<210> SEQ ID NO 91
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gaccagcaag ttaagcaaaa ttcaccatc                                       29

<210> SEQ ID NO 92
<211> LENGTH: 26
<212> TYPE: DNA
```

<213> ORGANISM: Artificial Sequence
<220> FEATURE:
<223> OTHER INFORMATION: Description of Artificial Sequence: Synthetic
    primer

<400> SEQUENCE: 92
caacaaccag tgcagagtcc tcaagc 26

<210> SEQ ID NO 93
<211> LENGTH: 27
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 93
agccaagaac tggagcagag tcctcag 27

<210> SEQ ID NO 94
<211> LENGTH: 29
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 94
ggtcaacagc tgaatcagag tcctcaatc 29

<210> SEQ ID NO 95
<211> LENGTH: 31
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 95
gaagacaagg tggtacaaag ccctctatct c 31

<210> SEQ ID NO 96
<211> LENGTH: 29
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 96
gaagacaagg tggtacaaag ccctcaatc 29

<210> SEQ ID NO 97
<211> LENGTH: 28
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 97
gcccagacag tcactcagtc tcaaccag 28

<210> SEQ ID NO 98
<211> LENGTH: 25
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 98
gcccagacag tcactcagtc ccagc                                           25

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
gctcagacag tcactcagtc tcaaccagag                                      30

<210> SEQ ID NO 100
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gagctgaaag tggaacaaaa ccctctgttc                                      30

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
agcaattcag tcaagcagac gggc                                            24

<210> SEQ ID NO 102
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
aaaaatgaag tggagcagag tcctcagaac                                      30

<210> SEQ ID NO 103
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gatactggaa ttacccagac accaaaatac ctg                                  33

<210> SEQ ID NO 104
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 104
gaacctgaag tcacccagac tcccag                                          26

<210> SEQ ID NO 105
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gacacagctg tttcccagac tccaaaatac                                      30

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gacacagccg tttcccagac tcca                                            24

<210> SEQ ID NO 107
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gacactgaag ttacccagac accaaaacac                                      30

<210> SEQ ID NO 108
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
cacctggtca tgggaatgac aaataagaag                                      30

<210> SEQ ID NO 109
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gaaacgggag ttacgcagac accaag                                          26

<210> SEQ ID NO 110
<211> LENGTH: 32
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 110
aagaagtctt tgaaatgtga acaacatctg gg                                32

<210> SEQ ID NO 111
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
aaggctggag tcactcaaac tccaagatat c                                 31

<210> SEQ ID NO 112
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
agggctgggg tcactcaaac tcc                                          23

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
gaggctggag tcacccaaag tccc                                         24

<210> SEQ ID NO 114
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gagactggag tcacccaaag tcccac                                       26

<210> SEQ ID NO 115
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cagcaagtga cactgagatg ctcttctcag                                   30

<210> SEQ ID NO 116
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 116
actgtgtcct ggtaccaaca ggccct                                          26

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gacgctggag tcacccaaag tcc                                             23

<210> SEQ ID NO 118
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gaggctggag tcacacaaag tcccac                                          26

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
aggacagcaa gcgactctga gatgc                                           25

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
aatgctggtg tcactcagac ccca                                            24

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
attgctggga tcacccaggc ac                                              22

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 122
actgctggga tcacccaggc ac                                              22

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
ggtgctggag tctcccagtc cctg                                            24

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ggagctggag tctcccagtc ccc                                             23

<210> SEQ ID NO 125
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ggagctggag tttcccagtc ccc                                             23

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
ggtgctggag tctcccagac cc                                              22

<210> SEQ ID NO 127
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tgggagctca ggtgtgatcc aatttc                                          26

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
```
ggtgctggag tctcccagtc cc 22

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 129
ggtgctggag tctcccagtc tccc 24

<210> SEQ ID NO 130
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 130
gatactggag tctcccagaa ccccag 26

<210> SEQ ID NO 131
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 131
gatactggag tctcccagga ccccag 26

<210> SEQ ID NO 132
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 132
atatctggag tctcccacaa ccccagac 28

<210> SEQ ID NO 133
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 133
cacaaccgcc tttattggta ccgacag 27

<210> SEQ ID NO 134
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 134
gattctggag tcacacaaac cccaaagc                                              28

<210> SEQ ID NO 135
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gatgctgaaa tcacccagag cccaag                                                26

<210> SEQ ID NO 136
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gatgctggaa tcacccagag ccca                                                  24

<210> SEQ ID NO 137
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
aaggcaggtg accttgatgt gtcacc                                                26

<210> SEQ ID NO 138
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
gaagctgaag ttgcccagtc ccc                                                   23

<210> SEQ ID NO 139
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gaagctggag ttgcccagtc tcccag                                                26

<210> SEQ ID NO 140
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gaagctggag tggttcagtc tcccaga                                               27

<210> SEQ ID NO 141
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ggtctcccag atataagatt atagagaaga aacagc                              36

<210> SEQ ID NO 142
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gatgctggtg ttatccagtc acccagg                                        27

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gatgctggca ttatccagtc acccaag                                        27

<210> SEQ ID NO 144
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
gatgctggag ttatccagtc acccc                                          25

<210> SEQ ID NO 145
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gatgctagag tcacccagac accaagg                                        27

<210> SEQ ID NO 146
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gctgctggag tcatccagtc ccc                                            23

<210> SEQ ID NO 147
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 147
gaagctggag ttactcagtt ccccagc                27

<210> SEQ ID NO 148
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 148
gatgccatgg tcatccagaa cccaag                 26

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 149
ggtgaagaag tcgcccagac tcca                   24

<210> SEQ ID NO 150
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 150
gagcctggag tcagccagac cc                     22

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 151
aatgccggcg tcatgcagaa c                      21

<210> SEQ ID NO 152
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 152
gatggtggaa tcactcagtc cccaaag                27

```
<210> SEQ ID NO 153
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
ggtgctgtcg tctctcaaca tccgag                                         26

<210> SEQ ID NO 154
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
agtgctgtcg tctctcaaca tccgag                                         26

<210> SEQ ID NO 155
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gacaccaagg tcacccagag acctagac                                       28

<210> SEQ ID NO 156
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gacaccaagg tcacccagag acctagattt c                                   31

<210> SEQ ID NO 157
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
catgccaaag tcacacagac tccagg                                         26

<210> SEQ ID NO 158
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gatgctgatg ttacccagac cccaag                                         26

<210> SEQ ID NO 159
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gaagctgaca tctaccagac cccaagatac                                         30

<210> SEQ ID NO 160
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
gatgctgtag ttacacaatt cccaagacac ag                                      32

<210> SEQ ID NO 161
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
gatgctgtag ttacacaatt ctcaagacac agaatc                                  36

<210> SEQ ID NO 162
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gaagcccaag tgacccagaa ccc                                                23

<210> SEQ ID NO 163
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 163
gatgtgaaag taacccagag ctcgagatat c                                       31

<210> SEQ ID NO 164
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
agtgctgtca tctctcaaaa gccaagc                                            27

<210> SEQ ID NO 165
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
acgatccagt gtcaagtcga tagccaag                                        28

<210> SEQ ID NO 166
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
tctcagacta ttcatcaatg gccagcg                                         27

<210> SEQ ID NO 167
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
actattcatc aatggccagc gaccc                                           25

<210> SEQ ID NO 168
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
tcgtcggcag cgtcagatg                                                  19

<210> SEQ ID NO 169
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gtctcgtggg ctcggagatg tgtataagag acagtacagg aagcctcagc a              51

<210> SEQ ID NO 170
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gtctcgtggg ctcggagatg tgtataagag acagcaggag ggctcggca                 49

<210> SEQ ID NO 171
<211> LENGTH: 62
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 171
aatgatacgg cgaccaccga gatctacact cgtcggcagc gtcagatgtg tataagagac    60
ag                                                                   62

<210> SEQ ID NO 172
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
caagcagaag acggcatacg agatgtctcg tgggctcgga gatgtgtata agagacag     58

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Leu Ile Phe Gly Asn Glu Lys Leu Thr Phe
1               5                   10

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Thr Gly Lys Leu Ile Phe
1               5
```

PAIRING ANTIGEN SPECIFICITY OF A T CELL WITH T CELL RECEPTOR SEQUENCES

CROSS REFERENCE TO RELATED APPLICATIONS

This application is the National Stage of International Application No. PCT/US2018/021611, filed Mar. 8, 2018, which claims the benefit of U.S. Provisional Application No. 62/468,448, filed Mar. 8, 2017, both of which are hereby incorporated by reference herein in their entirety, for all purposes.

STATEMENT REGARDING FEDERALLY SPONSORED RESEARCH OR DEVELOPMENT

This invention was made with government support under CA199090 awarded by the National Institutes of Health. The government has certain rights in the invention.

SEQUENCE LISTING

The instant application contains a Sequence Listing which has been submitted via EFS-Web and is hereby incorporated by reference in its entirety. Said ASCII copy, created on Apr. 12, 2018, is named 39730WO_CRF_sequencelisting.txt, and is 42,495 bytes in size.

BACKGROUND

An outstanding challenge in immunology is that of matching, for a given T cell, the T cell receptor (TCR) sequence with the antigen-specificity of that T cell. The T cell receptor gene of many T cells is a heterodimeric protein, with two components-alpha ($\alpha$) and beta (B) chains. Similar to antibodies, these two chains have a constant region and a variable region. If T cells are collected from a patient, generally each individual T cell has a unique TCR gene that enables that T cell to recognize a unique antigen.

Pairing the antigen specificity of a T cell with the TCR gene is informative and useful. For example, knowledge of the antigens that a T cell subset recognizes can guide the design of therapy. Likewise, knowledge of TCR genes can guide the design of an engineered cell-based therapy. However, previous approaches for antigen-specific T cell pairing have shown to be laborious, non-quantitative, and/or they may only identify one or two T cell populations per HLA genotype due to limited sensitivity. Thus, the ability to analyze TCR antigen specificity at the single cell level remains a significant need in the field.

SUMMARY

Disclosed herein is a composition comprising at least one particle, wherein the composition comprises: a) an MHC display moiety comprising at least one antigenic peptide; b) a first single-stranded polynucleotide sequence, the first sequence comprising in a 5' to 3' orientation: 1) a universal target sequence; 2) a unique, defined barcode sequence, wherein the defined barcode sequence is operably associated with the identity of the antigenic peptide; and 3) a T cell receptor (TCR) a primer sequence, wherein the TCR$\alpha$ primer sequence is complementary to a TCR$\alpha$ RNA transcript; and c) a second single-stranded polynucleotide sequence, the second sequence comprising in a 5' to 3' orientation: 1) the universal target sequence; 2) the defined barcode sequence; and 3) a TCR$\beta$ primer sequence, wherein the TCR$\beta$ primer sequence is complementary to a TCR$\beta$ RNA transcript; and d) the at least one particle; and wherein the MHC display moiety, the first single-stranded polynucleotide sequence, and the second single-stranded polynucleotide sequence are attached, with or without a linker, to the particle.

Also disclosed herein is a composition comprising at least one particle, wherein the composition comprises: a) an MHC display moiety comprising: a streptavidin core bound to four copies of a biotinylated MHC, and four copies of a neoantigen, wherein each copy is independently bound to one of the biotinylated MHCs a first polynucleotide hybridization domain; b) a first single-stranded polynucleotide sequence, the first sequence comprising in a 5' to 3' orientation: 1) a biotin; 2) a photocleaveable group; 3) a universal target sequence; 4) a unique, defined barcode sequence, wherein the defined barcode sequence is operably associated with the identity of the antigenic peptide; and 5) a T cell receptor (TCR) a primer sequence, wherein the TCR$\alpha$ primer sequence is complementary to a TCR$\alpha$ RNA transcript; and c) a second single-stranded polynucleotide sequence, the second sequence comprising in a 5' to 3' orientation: 1) a biotin; 2) a photocleaveable group; 3) the universal target sequence; 4) the defined barcode sequence; and 5) a TCR$\beta$ primer sequence, wherein the TCR$\beta$ primer sequence is complementary to a TCR$\beta$ RNA transcript; and d) at least one magnetic nanoparticle comprising: streptavidin and a second polynucleotide hybridization domain complementary to the first polynucleotide hybridization domain; and wherein the MHC display moiety is attached to the at least one magnetic nanoparticle by hybridization of the first and the second polynucleotide hybridization domains, and wherein the first and the second single-stranded polynucleotide sequence are independently attached to the at least one magnetic nanoparticle through a biotin-streptavidin interaction.

In some embodiment, the universal target sequence is a polymerase chain reaction (PCR) primer target sequence.

In some embodiments, wherein the at least one particle is selected from the group consisting of: a surface, a nanoparticle, a bead, and a polymer. In some embodiments, the nanoparticle is a magnetic nanoparticle or a polystyrene nanoparticle. In some embodiments, the magnetic nanoparticle comprises magnetic iron oxide. In some embodiments, the bead is an agarose bead or a SEPHAROSE bead.

In some embodiments, the composition further comprising a fluorophore. In some embodiments, the fluorophore is attached, with or without a linker, to the at least one particle.

In some embodiments, the first and the second single-stranded polynucleotide sequences are each independently and directly attached to the at least one particle.

In some embodiments, the first and the second single-stranded polynucleotide sequences each further comprise a cleavage moiety positioned between the at least one particle and the respective sequence. In some embodiments, the cleavage moiety comprises a photocleavable group. In some embodiments, the photocleavable group is cleavable by UV-light. In some embodiments, the photocleavable group comprises the formula:

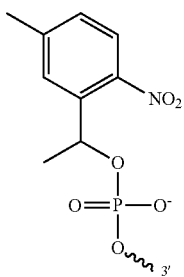

In some embodiments, the MHC display moiety is directly attached to the at least one particle. In some embodiments, the at least one particle further comprises a first polynucleotide hybridization domain and the MHC display moiety further comprises a second polynucleotide hybridization domain. In some embodiments, the first polynucleotide hybridization domain comprises the nucleotide sequence CTGAATCCTCGGGATGCCTA (SEQ ID NO: 8) and the second polynucleotide hybridization domain comprises the reverse complement TAGGCATCCCGAGGATTCAG (SEQ ID NO: 9). In some embodiments, the MHC display moiety is attached to the at least one particle by hybridization of the first polynucleotide hybridization domain to the second polynucleotide hybridization domain.

In some embodiments, the first and the second single-stranded polynucleotide sequences further comprise an attachment moiety, and the at least one particle further comprises a complementary attachment moiety. In some embodiments, the attachment moiety comprises biotin and the complementary attachment moiety comprises streptavidin, and wherein the first and the second sequences are attached to the at least one particle through a biotin-streptavidin interaction. In some embodiments, the streptavidin is a cysteine-modified streptavidin. In some embodiments, the attachment moiety further comprises a fluorophore. In some embodiments, the cleavage moiety is positioned between the attachment moiety and the first single-stranded polynucleotide sequence. In some embodiments, the cleavage moiety is positioned between the attachment moiety and the second single-stranded polynucleotide sequence.

In some embodiments, the at least one antigenic peptide is selected from the group consisting of: a tumor antigen, a neoantigen, a tumor neoantigen, a viral antigen, a phosphoantigen, a bacterial antigen, a microbial antigen, and combinations thereof. In some embodiments, the at least one antigenic peptide is a neoantigen. In some embodiments, the neoantigen is selected by analyzing tumor, viral, or bacterial sequencing data from a subject to identify one or more somatic mutations. In some embodiments, the analyzing is performed using an in silico predictive algorithm. In some embodiments, the predictive algorithm comprises an MHC binding algorithm to predict binding between the neoantigen and a MHC allele of the subject. In some embodiments, the MHC display moiety is the MHC allele of the subject.

In some embodiments, the MHC display moiety comprises a mammalian MHC. In some embodiments, the mammalian MHC comprises a human MHC.

In some embodiments, the mammalian MHC comprises a MHC class I molecule. In some embodiments, the MHC class I molecule comprises a MHC molecule selected from the group consisting of: HLA-A, HLA-B, and HLA-C. In some embodiments, the at least one antigenic peptide is 7-15, 7-10, 8-9, 7, 8, 9, 10, 11, 12, 13, 14, or 15 amino acids in length. In some embodiments, the at least one antigenic peptide is between 8-10 amino acids in length.

In some embodiments, the mammalian MHC comprises a MHC class II molecule. In some embodiments, the MHC class II molecule comprises and MHC molecule selected from the group consisting of: HLA-DQ and HLA-DR. In some embodiments, the at least one antigenic peptide is 11-30, 14-20, 15-18, 11, 12, 13, 14, 15, 16, 17, 18, 19, 20, 21, 22, 23, 24, 25, 26, 27, 28, 29, or 30 amino acids in length. In some embodiments, the at least one antigenic peptide is between 10 and 35, between 10 and 30, between 10 and 25, or between 10 and 20 amino acids in length.

The composition of any of the embodiments of the thirteenth-to-the-first paragraphs preceding the present paragraph, wherein the MHC display moiety comprises a multimerized MHC. In some embodiments, the multimerized MHC comprises a streptavidin core bound to multiple MHCs. In some embodiments, the streptavidin core further comprises a fluorescent molecule. In some embodiments, the streptavidin core is bound to four copies of biotinylated MHC. In some embodiments, the streptavidin core is bound to three copies of biotinylated MHC.

In some embodiments, the MHC display moiety comprises a single chain trimer MHC. In some embodiments, the single chain trimer comprises a disulfide trap.

In some embodiments, the universal target sequence is between 10-50, between 15-40, between 15-35, between 15-30, between 20-40, between 25-40, or between 30-40 nucleotides in length. In some embodiments, the universal target sequence is between 25-35 nucleotides in length. In some embodiments, the universal target sequence is at least about 15 nucleotides in length. In some embodiments, the universal target sequence comprises the sequence TCGTCGGCAGCGTCAGATGTGTATAAGAGACAG (SEQ ID NO: 3)

In some embodiments, the defined barcode sequence is between 4-10 nucleotides in length. In some embodiments, the defined barcode sequence is about 6 nucleotides in length. In some embodiments, the defined barcode sequence is 6 nucleotides in length. In some embodiments, the defined barcode sequence is at least 6 nucleotides in length.

In some embodiments, the TCRα primer sequence and the TCRβ primer sequence are between 10-50, between 15-40, between 15-35, between 15-30, between 15-25, between 15-20, or between 10-20 nucleotides in length. In some embodiments, the TCRα primer sequence is designed to hybridize to a TCRα RNA transcript sequence. In some embodiments, the TCRα RNA transcript sequence comprises a TCRα constant region sequence. In some embodiments, the TCRα primer sequence comprises the nucleotide sequence TCTCTCAGCTGGTACACGGC (SEQ ID NO: 4).

In some embodiments, the TCRβ primer sequence is designed to hybridize to a TCRβ RNA transcript sequence. In some embodiments, the TCRβ RNA transcript sequence comprises a TCRβ constant region sequence. In some embodiments, the TCRβ primer sequence comprises the nucleotide sequence GATGGCTCAAACACAGCGACCTC (SEQ ID NO: 5).

In some embodiments, the TCRα RNA transcript and the TCRβ RNA transcript comprise mammalian transcripts. In some embodiments, the mammalian transcripts comprise human transcripts.

In some embodiments, the first and the second single-stranded polynucleotide sequences each further comprise a random nucleotide sequence. In some embodiments, each of the random nucleotide sequences is between 6-20, between 6-15, between 6-12, between 6-10, or between 6-8 nucleotides in length. In some embodiments, each of the random nucleotides sequence is 8 nucleotides in length. In some embodiments, each of the random nucleotide sequences is positioned between the universal target sequence and the defined barcode sequence.

In some embodiments, multiple copies of the first and the second single-stranded polynucleotide sequences are attached to the bead. In some embodiments, each of the multiple copies of the first and the second single-stranded polynucleotide sequences comprise a random nucleotide sequence, wherein each of the random sequences is unique for each of the multiple copies.

In some embodiments, the at least one particle is further bound to a TCR, wherein the TCR specifically binds the MHC display moiety. In some embodiments, the TCR is on the surface of a T cell. In some embodiments, the T cell is selected from the group consisting of: a CTL, a CD8+ T cell, a CD4+ T cell, a primary T cell, an ex vivo cultured T cell, a tumor infiltrating T cell, and an engineered T cell. In some embodiments, the T cell is isolated from a subject. In some embodiments, the subject is known or suspected to have cancer.

In some embodiments, the at least one particle is isolated within a droplet. In some embodiments, the droplet is a water-in-oil emulsion. In some embodiments, the droplet further comprises a lysis reagent, wherein the lysis reagent optionally comprises a surfactant. In some embodiments, the surfactant comprises IGEPAL CA 630. In some embodiments, the IGEPAL CA 630 is at a final concentration of about 0.25%.

In some embodiments, the droplet further comprises one or more components for reverse transcription. In some embodiments, the components for reverse transcription are selected from the group consisting of: reverse transcriptase, dNTPs, RNase inhibitors, buffering agents, chelators, DTT, and combinations thereof. In some embodiments, reverse transcriptase comprises a RNaseH positive recombinant reverse transcriptase In some embodiments, the final concentration of the DTT is about 5 mM.

In some embodiments, the droplet further comprises components for DNA PCR amplification. In some embodiments, the components for DNA PCR amplification are selected from the group consisting of: DNA polymerase, dNTPs, buffering agents, chelators, amplification primers, and combinations thereof. In some embodiments, DNA polymerase is a recombinant *Thermococcus kodakaraensis* KOD1 DNA polymerase.

In some embodiments, the amplification primers comprise a TCRα forward primer and a TCRβ forward primer. In some embodiments, the TCRα forward primer and TCRβ forward primer are designed to amplify at least a portion of a TCR complementarity determining region (CDR) 3 sequence. In some embodiments, the TCRα forward primer and TCRβ forward primer are multiplexed primers. In some embodiments, the TCRα multiplexed primers are selected from the group consisting of the Vα sequences in Table 3, and the TCRβ multiplexed primers are selected from the group consisting of the Vβ sequences in Table 4.

In some embodiments, the droplet has been exposed to a releasing stimulus. In some embodiments, the releasing stimulus comprises a light stimulus. In some embodiments, the light stimulus comprises UV light. In some embodiments, the releasing stimulus comprises a releasing reagent introduced into the droplet. In some embodiments, the releasing reagent is an enzymatic or chemical reagent. In some embodiments, the releasing reagent comprises a reducing reagent.

In some embodiments, the droplet further comprises the first and the second single-stranded polynucleotide sequences unattached to the at least one particle. In some embodiments, the composition further comprises a) a second particle; b) a second MHC display moiety comprising at least one second antigenic peptide, wherein the second antigenic peptide has a distinct sequence relative to the at least one antigenic peptide of any of the composition embodiments of the $28^{th}$-to-the-first paragraphs preceding the present paragraph; c) a third single-stranded polynucleotide sequence, the third sequence comprising in a 5' to 3' orientation: 1) the universal polymerase chain reaction (PCR) primer target sequence; 2) a second unique, defined barcode sequence, wherein the second defined barcode sequence is operably associated with the identity of the second antigenic peptide, and wherein the second defined barcode sequence is distinct from the defined barcode sequence of any of the above composition claims; and 3) the T cell receptor (TCR) a primer sequence, and d) a fourth single-stranded polynucleotide sequence, the fourth sequence comprising in a 5' to 3' orientation: 1) the universal target sequence; 2) the second defined barcode sequence; and 3) the TCRβ primer sequence; wherein the second MHC display moiety, the third single-stranded polynucleotide sequence, and the fourth single-stranded polynucleotide sequence are attached, with or without a linker, to the second particle. In some embodiments, the composition further comprises a plurality of the first and the second particles.

Also described herein is a library comprising any of the above compositions, wherein the library comprises greater than or equal to two distinct particles, each distinct particle comprising a unique antigen and a unique, defined barcode sequence operably associated with the identity of each unique antigen. The second particle and the greater than or equal to two distinct particles can have any of the properties of the at least one particle described above.

Also described herein is a kit comprising the composition of any of the embodiments of the $30^{th}$-to-the-second paragraphs preceding the present paragraph, and instructions for use.

Also described herein is a method for manufacturing any of the above compositions, the method comprising the steps of: a) obtaining elements (a)-(d) of any of the embodiments of the $31^{st}$-to-the-third paragraphs preceding the present paragraph, wherein one or more of elements (a)-(c) are optionally attached to the at least one particle prior to obtaining elements (a)-(d); and b) attaching one or more of elements (a)-(c) to the at least one particle. In some embodiments, the at least one antigenic peptide comprises a cleavable peptide and the method further comprises the steps of: c) displacing the cleavable peptide from the MHC display moiety; and d) providing an antigenic peptide of interest. In some embodiments, the obtaining step comprises: synthesizing or having synthesized one or more of elements (a)-(c).

Also described herein is a method for isolating an antigen specific T cell, the method comprising the steps of: a) providing any of the above compositions; b) providing a sample known or suspected to comprise one or more T cells; c) contacting the composition with the sample, wherein the contacting comprises providing conditions sufficient for a single T cell to bind the MHC display moiety attached to the at least one particle, and d) isolating the single T cell associated with the at least one particle.

In some embodiments, the isolating comprises magnetic separation when the at least one particle is magnetic. In some embodiments, the magnetic separation comprises capturing the at least one particle against a wall with a magnet and removing elements not captured against the wall. In some embodiments, the isolating comprises using fluorescence-activated cell sorting (FACS).

In some embodiments, the isolating step comprises using a microfluidic device. In some embodiments, the microfluidic device comprises a flow cytometer. In some embodiments, the microfluidic device comprises a deterministic lateral displacement (DLD) device. In some embodiments, the DLD device that separates the single T cell associated with the at least one particle from unbound particles.

In some embodiments, the microfluidic device comprises a droplet generating device that isolates the single T cell in a droplet, and the droplet does not contain another T cell or an unbound particle. In some embodiments, the droplet comprises an aqueous fluid encapsulated in an immiscible carrier fluid. In some embodiments, the immiscible carrier fluid comprises an oil. In some embodiments, the oil comprises a fluorinated oil. In some embodiments, the fluorinated oil comprises HFE-7500.

In some embodiments, the immiscible carrier fluid further comprises a surfactant. In some embodiments, the surfactant comprises a fluorosurfactant. In some embodiments, the fluorosurfactant comprises a 5% w/w PEG-PFPE amphiphilic block copolymer.

In some embodiments, the method further comprises adding a lysis reagent In some embodiments, the lysis reagent is added immediately prior to isolating the single T cell in the droplet, such that the lysis reagent is contained within the droplet.

In some embodiments, the method further comprises adding a RNA reverse transcriptase. In some embodiments, the RNA reverse transcriptase is added immediately prior to isolating the single T cell in the droplet, such that the reverse transcriptase is contained within the droplet. In some embodiments, the RNA reverse transcriptase comprises a RNaseH positive recombinant reverse transcriptase.

In some embodiments, the method further comprises adding a DNA polymerase. In some embodiments, the DNA polymerase is added immediately prior to isolating the single T cell in the droplet, such that the DNA polymerase is contained within the droplet. In some embodiments, the DNA polymerase is a recombinant *Thermococcus kodakaraensis* KOD1 DNA polymerase.

In some embodiments, the method further comprises adding: a) a TCRα forward primer, the TCRα forward primer comprising a second universal target sequence and a sequence designed to hybridize to a TCRα variable region sequence; b) a TCRβ forward primer, the TCRβ forward primer comprising the second universal target sequence and a sequence designed to hybridize to a known TCRβ variable region sequence; wherein the TCRα forward primer and TCRβ forward primer are contained within the droplet.

In some embodiments, the TCRα forward primer and TCRβ forward primer are added immediately prior to isolating the single T cell in the droplet, such that the TCRα forward primer and TCRβ forward primer are contained within the droplet. In some embodiments, the TCRα forward primer and TCRβ forward primer are designed to amplify at least a portion of a TCR complementarity determining region (CDR) 3 sequence. In some embodiments, the e TCRα forward primer and TCRβ forward primer comprise TCRα multiplexed primers and TCRβ multiplexed primers. In some embodiments, the TCRα multiplexed primers are selected from the group consisting of the Vα sequences in Table 3, and the TCRβ multiplexed primers are selected from the group consisting of the Vβ sequences in Table 4.

In some embodiments, the method further comprises adding dithiothreitol (DTT). In some embodiments, the DTT is added immediately prior to isolating the single T cell in the droplet, such that the DTT is contained within the droplet. In some embodiments, the final concentration of the DTT is about 5 mM.

In some embodiments, the method further comprises adding additional components for nucleic acid amplification, wherein the additional components are selected from the group consisting of: dNTPs, DNase inhibitors, RNase inhibitors, buffering agents, chelators, divalent ions, and combinations thereof. In some embodiments, the one or more of the additional components are added immediately prior to isolating the single T cell in the droplet such that the additional components are contained within the droplet.

In some embodiments, the isolating step comprises collecting the droplet, optionally in a collection tube. In some embodiments, the isolating step comprises dispersing the droplet in tubing, followed by collecting the droplet in a collection tube.

In some embodiments, the droplet is 70 micrometers or less, 65 micrometers or less, 60 micrometers or less, 55 micrometers or less, or 50 micrometers or less in diameter. In some embodiments, the droplet is 40-70 micrometers, 40-60 micrometers, or 50-60 micrometers in diameter. In some embodiments, the droplet is about 55 micrometers in diameter. In some embodiments, the droplet is 30-110 picoliters, 50-100 picoliters, 60-100 picoliters, 70-100 picoliters, 70-90 picoliters, or 75-85 picoliters in volume. In some embodiments, the droplet is about 80 picoliters in volume.

In some embodiments, the method further comprises releasing a portion of the first and a portion of the second sequence from the at least one particle, each portion comprising the universal target sequence, the defined barcode sequence, and the respective TCRα or TCRβ primer sequence. In some embodiments, the releasing comprises cleaving the cleavage moiety. In some embodiments, the cleaving comprises exposing the at least one particle to ultraviolet (UV) light. In some embodiments, the e cleaving comprises exposing the at least one particle to a releasing agent. In some embodiments, the releasing agent comprises an enzymatic or chemical reagent. In some embodiments, the chemical cleavage reagent is a reducing agent. In some embodiments, the method further comprises adding the releasing agent immediately prior to isolating the single T cell in the droplet, such that the releasing agent is contained within the droplet. In some embodiments, the releasing is performed in the collection tube. In some embodiments, the releasing in performed is tubing prior to collecting the droplet in the collection tube.

In some embodiments, the method further comprises generating or having generated a cDNA mixture, wherein the generating comprises reverse transcription, and the resulting cDNA mixture comprises a sequence complementary to the TCRα RNA transcript and a sequence complementary to the TCRβ RNA transcript. In some embodiments, the method further comprises extracting or having extracted the cDNA mixture from the droplet. In some embodiments, the extracting comprises the steps of: A) adding a de-emulsification reagent; B) collecting the aqueous solution, wherein the aqueous solution comprises the cDNA mixture. In some embodiments, the method further comprises an amplification step, the step comprising: i) contacting the resulting cDNA mixture with a forward amplification primer, the forward amplification primer comprising a third universal target sequence and a sequence capable of hybridizing to at least a portion of the first universal target sequence; ii) contacting the resulting cDNA mixture with a reverse amplification primer, the reverse amplification primer comprising a fourth universal target sequence and a sequence capable of hybridizing to at least a portion of the second universal target sequence; iii) performing a DNA amplification to produce an amplified cDNA mixture; and iv) optionally, purifying the amplified cDNA mixture. In some embodiments, the purifying comprises isolating the cDNA mixture on an agarose gel.

In some embodiments, the method further comprises sequencing or having sequenced the cDNA mixture. In some embodiments, the sequencing comprises next generation sequencing. In some embodiments, the method further comprises assigning or having assigned a paired TCRα sequence and TCR β sequence to the at least one antigenic peptide associated with the single T cell using the defined barcode sequence.

In some embodiments, the antigen specific T cell is selected from the group consisting of: a primary T cell, an ex vivo cultured T cell, a tumor infiltrating T cell, and an engineered T cell. In some embodiments, the sample is selected from the group consisting of: blood, plasma, a peripheral blood mononuclear cell population, a tissue homogenate, a tumor homogenate, and an ex vivo T cell culture.

Also disclosed herein is a method of treatment for a subject in need thereof, the method comprising administering a therapeutically effective amount of treatment comprising the paired TCRα sequence and TCR β sequence identified using any of the above methods.

Also disclosed herein is a microfluidic device comprising: a sample inlet; a separation channel comprising an array of obstacles disposed within the separation channel, wherein the array of obstacles comprises a plurality of rows of obstacles and a plurality of columns of obstacles, the plurality of rows of obstacles extending at an angle relative to the average flow direction of the separation channel; a droplet generator; and a collection outlet, wherein the separation channel is disposed between and in fluidic communication with the sample inlet and the droplet generator, and the collection outlet is in fluidic communication with and downstream of the droplet generator.

In some embodiments, the separation channel bifurcates into a waste channel and a collection channel, wherein the collection channel forms a fluidic junction between the array of obstacles and the droplet generator, and wherein the waste channel forms a fluidic junction between the array of obstacles and a waste outlet.

In some embodiments, the array of obstacles is adapted to separate particles having a size at or above a critical size from particles having a size less than the critical size in a flow of a heterogeneous fluid sample through the separation channel. In some embodiments, the particles having a size at or above the critical size comprise a nanoparticle bound to a cell, and the particles having a size less than the critical size comprise an unbound nanoparticle. In some embodiments, the cell is a T cell.

In some embodiments, the critical size is a diameter from 2 to 7 μm. In some embodiments, the particles having the size at or above the critical size are at least twice the diameter, at least three times the diameter, at least four times the diameter, at least five times the diameter, at least six times the diameter, at least seven times the diameter, or at least at least eight times the diameter of the particles having a size less than the critical size. In some embodiments, the particles having a size at or above the critical size are at least eight times the diameter of the particles having a size less than the critical size.

In some embodiments, the array of obstacles is configured to deflect the particles having a size at or above the critical size towards a first wall of the separation channel. In some embodiments, the array of obstacles is configured to deflect particles having a size less than the critical size towards a second wall of the separation channel opposite from the first wall, wherein the separation channel is bounded by the first wall and the second wall. In some embodiments, the collection channel is bounded by the first wall on one side, and the waste channel is bounded by the second wall on one side.

In some embodiments, the array of obstacles are fixed in position and separated by gaps arranged so that the particles having a size at or above the critical size deflect towards a first wall of the separation channel during flow of the heterogeneous fluid sample through the separation channel. In some embodiments, the obstacles are I-shaped. In some embodiments, the angle relative to the average flow direction of the separation channel is from 1 degree to 15 degrees, from 3 degrees to 12 degrees, from 4 degrees to 8 degrees, from 5 degrees to 7 degrees, or from 5.5 degrees to 6 degrees. In some embodiments, the angle relative to the average flow direction of the separation channel is about 6 degrees. In some embodiments, the angle relative to the average flow direction of the separation channel is about 3 degrees, 4 degrees, 5 degrees, 6 degrees, 7 degrees, 8 degrees, 9 degrees, or 10 degrees. In some embodiments, the plurality of rows of obstacles comprises a gap between adjacent rows of from 8 μm to 15 μm. In some embodiments, the plurality of rows of obstacles comprises a gap between adjacent rows of from 10 μm to 13 μm. In some embodiments, the plurality of columns of obstacles comprise a gap between adjacent columns of from 8 μm to 15 μm. In some embodiments, the plurality of columns of obstacles comprise a gap between adjacent columns of from 10 μm to 13 μm.

In some embodiments, the array of obstacles extends into the collection channel. In some embodiments, the array of obstacles extends into the waste channel.

In some embodiments, the microfluidic device further comprises a cell-focusing channel disposed between and in fluidic communication with the separation channel and the one or more capture areas In some embodiments, the cell-focusing channel is configured to orderly arrange particles having a size at or above a critical size. In some embodiments, the cell-focusing channel is configured to reduce the flow rate of the particles having a size at or above a critical size. In some embodiments, the cell-focusing channel is serpentine-shaped.

In some embodiments, the microfluidic device further comprises a buffer inlet disposed adjacent to the sample inlet and in fluidic communication with the separation channel.

In some embodiments, the microfluidic device further comprises a collection container, wherein the collection container is downstream from and in fluidic communication with the collection outlet, and the collection container is configured to collect discrete droplets. In some embodiments, the collection container is not physically attached to the collection outlet. In some embodiments, the collection container is selected from the group consisting of: a tube, a PCR tube, a microcentrifuge tube, a test tube, a round-bottom tube, a conical tube, and a multi-well plate.

In some embodiments, the microfluidic device further comprises a tubing, wherein the tubing is in fluidic communication with and disposed between the droplet outlet and the collection outlet. In some embodiments, the tubing comprises a UV permissible material.

In some embodiments, the microfluidic device further comprises a first syringe pump connected to the waste outlet and a second syringe pump connected to the collection outlet. In some embodiments, the first, the second, or the first and second syringe pumps are configured to supply a vacuum. In some embodiments, no inlets are connected to a syringe pump.

In some embodiments, the first syringe pump is capable of producing a first withdrawal flow rate, and the second syringe pump is capable of producing a second withdrawal flow rate. In some embodiments, the first and the second withdrawal flow rate are at rates so that only the particles having a size at or above the critical size deflect towards a first wall of the separation channel during flow of the heterogeneous fluid sample through the separation channel. In some embodiments, the first and the second withdrawal flow rate are different rates.

In some embodiments, the droplet generator comprises: a) a flow-focusing nozzle; b) a carrier inlet; and c) a droplet outlet, wherein the flow-focusing nozzle is configure to receive a particle-containing fluid from the separation channel, the carrier inlet intersects the flow-focusing nozzle, and the intersection of the carrier inlet and the flow-focusing nozzle is arranged in fluidic communication with the droplet outlet so that a discrete droplet encapsulating the particle-containing fluid is capable of forming and entering the droplet outlet.

In some embodiments, the carrier inlet is adapted to carry an immiscible carrier fluid. In some embodiments, the carrier inlet, the flow-focusing nozzle, and the droplet outlet are arranged to produce discrete droplets 70 micrometers or less, 65 micrometers or less, 60 micrometers or less, 55 micrometers or less, or 50 micrometers or less in diameter. In some embodiments, the carrier inlet, the flow-focusing nozzle, and the droplet outlet are arranged to produce discrete droplets 40-70 micrometers, 40-60 micrometers, or 50-60 micrometers in diameter. In some embodiments, the carrier inlet, the flow-focusing nozzle, and the droplet outlet are arranged to produce discrete droplets about 55 micrometers in diameter. In some embodiments, the flow-focusing nozzle comprises a flow-focusing inlet that tapers in diameter to a flow-focusing outlet, and the carrier inlet intersects the flow-focusing outlet. In some embodiments, the flow-focusing outlet is 60 micrometers or less in diameter.

In some embodiments, the carrier inlet, the flow-focusing nozzle, and the droplet outlet are arranged to produce discrete droplets 30-110 picoliters, 50-100 picoliters, 60-100 picoliters, 70-100 picoliters, 70-90 picoliters, or 75-85 picoliters in volume. In some embodiments, the carrier inlet, the flow-focusing nozzle, and the droplet outlet are arranged to produce discrete droplets about 80 picoliters in volume.

In some embodiments, the microfluidic device further comprises a second carrier inlet, and wherein the two carrier inlets both intersect the flow-focusing nozzle. In some embodiments, the flow-focusing nozzle and the droplet outlet are in a linear arrangement. In some embodiments, the carrier inlet or inlets intersect the flow-focusing nozzle at a 90 degree angle. In some embodiments, the carrier inlet or inlets intersect the flow-focusing nozzle at less than a 90 degree angle.

In some embodiments, the microfluidic device further comprises at least one reagent inlet, wherein the reagent inlet is in fluidic communication with and upstream of the flow-focusing nozzle. In some embodiments, the reagent channel is configured to introduce a miscible fluid into the particle-containing fluid. In some embodiments, the reagent channel is configured to produce about a 2:1 ratio of miscible fluid to particle-containing fluid. In some embodiments, the reagent channel is configured to produce a 2:1 ratio of miscible fluid to particle-containing fluid.

Also described herein is a method of producing a droplet encapsulated particle, the method comprising the steps of: a) providing a heterogeneous fluid sample comprising a plurality of particles having a size at or above a critical size and a plurality of particles having a size less than the critical size; b) introducing the heterogeneous fluid sample into the sample inlet of any one of the above microfluidic devices; and c) collecting discrete droplets comprising the particles having a size at or above a critical size.

In some embodiments, the discrete droplets comprise only 0 or 1 particles having a size at or above the critical size, and do not comprise a particle having a size less than the critical size. In some embodiments, the droplets comprise reagents for producing cDNA.

In some embodiments, the method further comprises the step of generating a cDNA mixture within the droplet. In some embodiments, the method further comprises the step of extracting the cDNA mixture from the droplet. In some embodiments, the method further comprises the step of sequencing the cDNA mixture. In some embodiments, the method further comprises the step of analyzing data generated from the sequencing step.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION

Figure 1A:
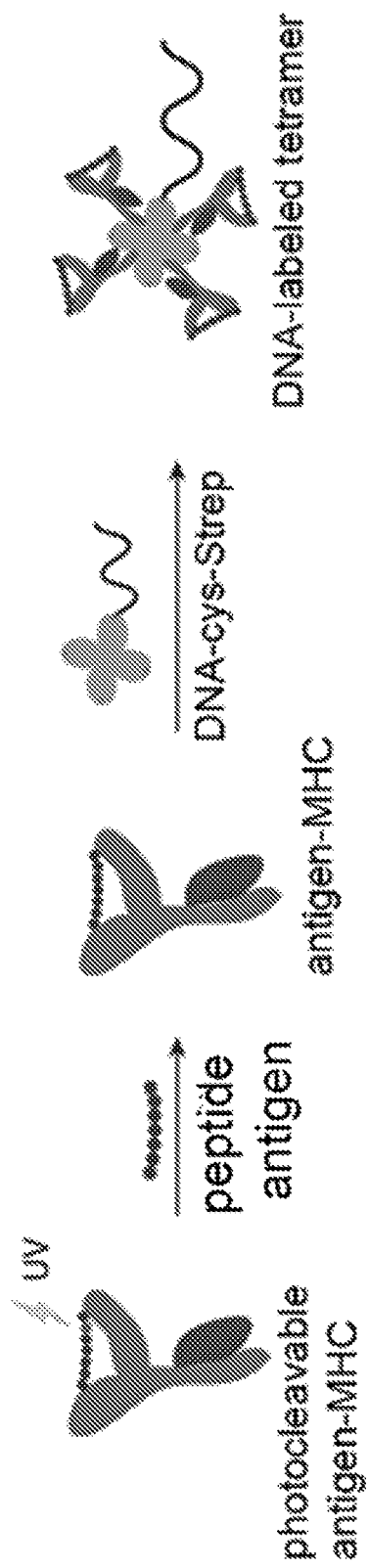
FIG. 1A illustrates an exemplary method for generating MHC display moieties.

The details of various embodiments of the invention are set forth in the description below. Other features, objects, and advantages of the invention will be apparent from the description and the drawings, and from the claims.

Definitions

Terms used in the claims and specification are defined as set forth below unless otherwise specified.

As used herein, "antigen-specific T cells" refer to cells that are distinguished from one another by their T cell receptors (TCRs), which give them their antigen specificity.

Embodiments of the present invention include a recombinant antigen-MHC complex that is capable of pairing with cognate T cells. As used herein, "antigen-MHC," "antigen-MHC complex," "recombinant antigen-MHC complex," "peptide MHC," and "p/MHC," are used interchangeably to refer to a major histocompatibility complex with a peptide in the antigen binding groove of MHC.

As used herein, "antigen" includes any antigen including patient-specific neoantigens. "Antigenic peptide" refers to a peptide fragment capable of binding an MHC molecule. "Neoantigen" refers to an antigen that has at least one alteration that makes the neoantigen or presentation of the neoantigen distinct from its corresponding wild-type antigen, e.g., mutations in the polypeptide sequence, differences is post-translation modifications, or differences in expression level. "Tumor neoantigens" refer to neoantigens that are derived from a tumor or a cancer, e.g., from the tumor of a patient."

As used herein, a "barcoded T cell," "paired T cell," "T-cell bound nanoparticle," and "T cell paired antigen MHC complex" refers to the complex of a T cell having a T cell receptor that binds to an antigen peptide presented by an MHC molecule on a barcoded NP-antigen-MHC complex.

The terms "DLD array" and "obstacle array" are used synonymously herein and can describe an ordered array of obstacles that are disposed in a flow channel through which a particle-bearing fluid can be passed.

In a DLD array, "fluid flow" and "bulk fluid flow" can be used synonymously to refer to the macroscopic movement of fluid in a general direction across an obstacle array. These terms do not take into account the temporary displacements of fluid streams for fluid to move around an obstacle in order for the fluid to continue to move in the general direction.

"The direction of bulk fluid flow" in an obstacle array device can refer to the average (e.g., macroscopic) direction of fluid flow through the device (i.e., ignoring local flow deviations necessitated by flow around obstacles in the fluid channel).

In a DLD array, the tilt angle θ can be the angle between the direction of bulk fluid flow and the direction defined by alignment of rows of sequential (in the direction of bulk fluid flow) obstacles in the array.

A "critical size" or "predetermined size" of particles passing through a DLD array can be a parameter that describes the size limit of particles that are able to follow the laminar flow of fluid nearest one side of a gap through which the particles are travelling when flow of that fluid diverges from the majority of fluid flow through the gap. Particles larger than the critical size can be 'bumped' from the flow path of the fluid nearest that side of the gap into the flow path of the majority of the fluid flowing through the gap. In a DLD array, such a particle can be displaced by the distance of (the size of one obstacle+the size of the gap between obstacles) upon passing through the gap and encountering the downstream column of obstacles, while particles having sizes lower than the critical size (or predetermined size) will not necessarily be so displaced. When a profile of fluid flow through a gap is symmetrical about the plane that bisects the gap in the direction of bulk fluid flow, the critical size can be identical for both sides of the gap; however when the profile is asymmetrical, the critical sizes of the two sides of the gap can differ. When assessing a non-spherical particle, its size can be considered to be the spherical exclusion volume swept out by rotation of the particle about a center of gravity in a fluid, at least for particles moving rapidly in solution. The size characteristics of non-spherical particles can be determined empirically using a variety of known methods, and such determinations can be used in selecting or designing appropriate obstacle arrays for use as described herein. Calculation, measurement, and estimation of exclusion volumes for particles of all sorts are well known.

The term "in vivo" refers to processes that occur in a living organism.

The term "mammal" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease.

It must be noted that, as used in the specification and the appended claims, the singular forms "a," "an" and "the" include plural referents unless the context clearly dictates otherwise.

INTRODUCTION

T-cell mediated immunity can be characterized by the activation of antigen-specific cytotoxic T cells that are able to induce death in cells that display antigen in a major histocompatibility complex (MHC) on their surface. These cells displaying an MHC complex loaded with antigen include virus-infected cells, cells with intracellular bacteria, cells that have internalized or phagocytosed extracellular sources of protein, and cancer cells displaying tumor antigens.

To utilize the T-cell mediated immunity process, e.g., for patient-specific cancer immunotherapy, one of the initial steps can include identification of the patient's tumor-specific antigens (e.g., neoantigens). For identification of a patient's putative neoantigens (tumor or pathogen), in silico predictive algorithmic programs can be utilized that analyze the tumor, viral, or bacterial sequencing data including whole genome, whole exome, or transcriptome sequencing data, to identify one or more mutations corresponding to putatively expressed neoantigens. Additionally, human leukocyte antigen (HLA) typing can be determined from a tumor or blood sample of the patient, and this HLA information can be utilized together with the identified putative neoantigen peptide sequences in a predictive algorithm for MHC binding, as verified by Fritsch et al., 2014, *Cancer Immunol Res.*, 2:522-529, the entire contents of which are herein incorporated by reference. HLAs commonly found in the human population can also be included in neoantigen prediction algorithms, such as HLA-A*02, 24, 01; HLA-B*35, 44, 51; DRB1*11, 13, 07 in caucasians, HLA-A*02, 03, 30; HLA-B*35, 15, 44; DRB1*13, 11, 03 in afro-brazialians, and HLA-A*24, 02, 26; HLA-B*40, 51, 52; DRB1*04, 15, 09 in Asians. Specific pairing of HLA alleles can also be used. Common alleles found in the human population is further described in Bardi et al. (Rev Bras Hematol Hemoter. 2012; 34 (1): 25-30.)

Additional examples of methods to identify neoantigens include combining sequencing with mass-spectrometry and MHC presentation prediction (e.g., US Publication No. 2017/0199961), and combining sequencing with MHC binding affinity prediction (e.g., issued U.S. Pat. No. 9,115,402). In addition, methods useful for identifying whether neoantigen specific T cells are present in a patient sample can be used in combination with the methods described here, e.g., as described in US Publication No. 2017/0003288 and PCT/US17/59598, herein incorporated by reference in their entirety. These analyses result in a ranked list of the patient's candidate neoantigen peptides which can be readily synthesized using routine methods for screening of cognate antigen-specific T cells.

Embodiments of the present invention use antigen-loaded MHC compositions for isolation and identification of patient-specific T cell populations targeted to patient-specific antigens, e.g., neoantigens. Specifically, the specific TCRα and TCRβ chains expressed in a single antigen specific T cell are determined allowing identification of a TCR that specifically recognizes a given antigen-MHC complex. In certain embodiments, a nanoparticle (NP) can have two barcoded polynucleotides for sequencing both the TCRα and TCRβ chains expressed in a T cell. The nanoparticle can be further attached to an antigen-MHC complex displaying a unique antigenic peptide. Utilizing the barcoded nanoparticle-antigen-MHC complex, T cells that pair with the antigen-MHC complex can then be isolated, e.g., by selective isolation of the nanoparticle. This typically results in a population that has a small number of nanoparticles with a T cell paired antigen MHC complex (i.e., bound nanoparticles), and a large number of nanoparticles that have an antigen MHC complex that is not bound to a T cell (i.e., unbound nanoparticles).

To correctly sequence the TCRα and TCRβ chains, single T cells bound to nanoparticles are separated from the unbound nanoparticles and isolated as single cells. In some embodiments, methods and devices are provided herein to separate bound and unbound nanoparticles, as well as to isolate nanoparticle bound T cells as single cells, e.g. in single-cell droplets or wells, to facilitate analysis and/or subsequent post-analysis processing.

In some embodiments provided herein is a microfluidic device that facilitates separation of bound and unbound nanoparticles and isolation of nanoparticle bound cells for analysis. In some embodiments, separation of bound and unbound nanoparticles is achieved in a microfluidic channel based upon deterministic lateral displacement (DLD), a size-based particle separation technique that relies on selective displacement of particles by an array of obstacles disposed in a flowing fluid.

In some embodiments, methods and devices are provided herein to isolate nanoparticle bound cells (i.e., barcoded T cells). In some embodiments, the isolation is performed in a microfluidic device designed to isolate barcoded T cells into individual single cell droplets or reaction vessels, where they can be further processed and analyzed. In some embodiments, barcoded T cells are isolated in droplets in a microfluidic device designed to provide reagents for high-throughput sequencing of TCR chains specific to each barcoded T cell.

The devices and methods described herein can be used, for example, to identify neoantigen-specific T cell populations, including their specific TCR chain pairing, from the tumor infiltrating lymphocytes (TILs) or peripheral blood mononuclear cells (PBMCs) of a cancer patient. In some embodiments, the analysis of such T cells and their respective TCR sequences informs the construction of immunotherapies such as personalized cancer vaccines or engineered-TCR T cell immunotherapies.

Barcoded Nanoparticle Library Formation

Figure 1B:
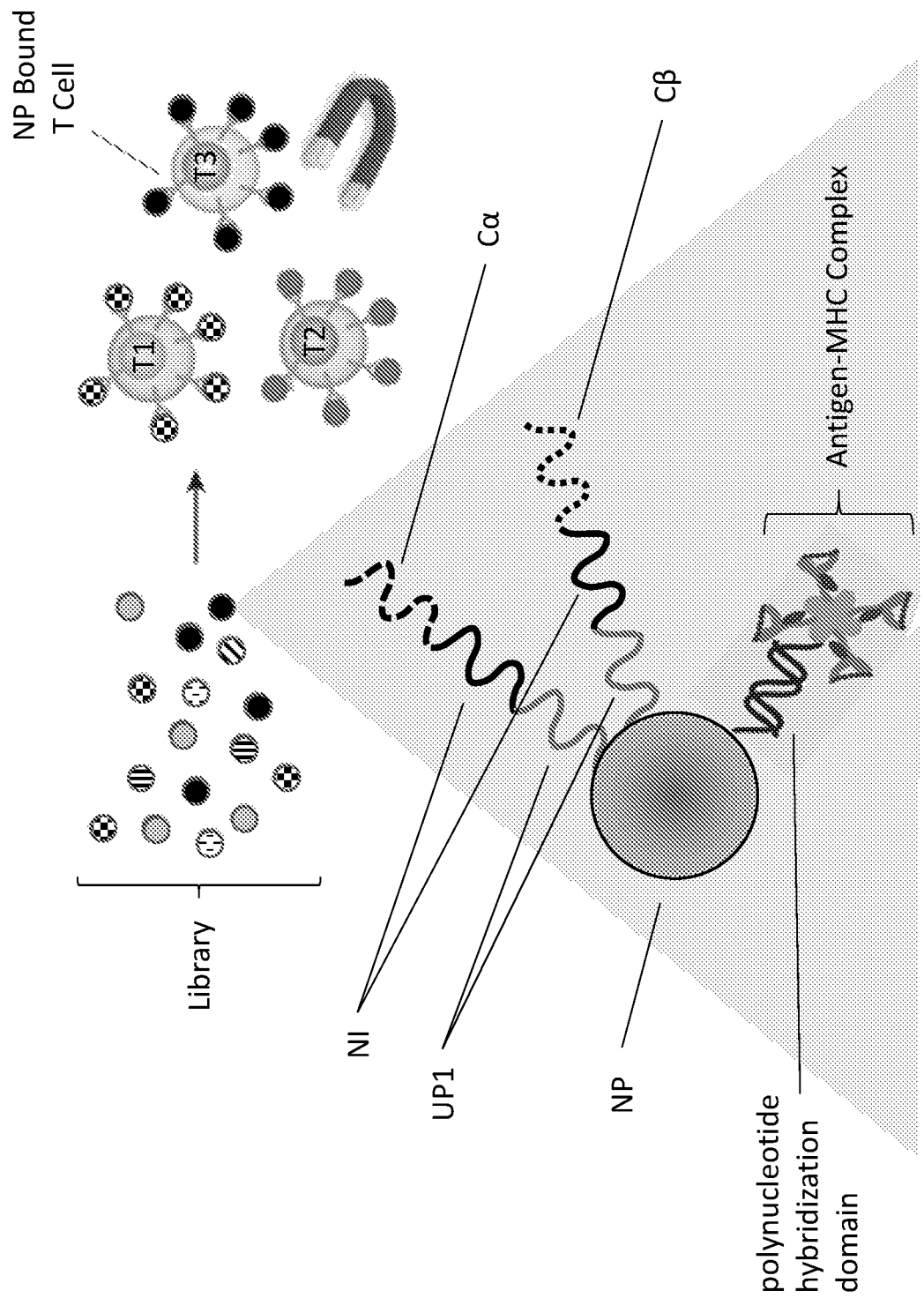
FIG. 1B illustrates the individual features of a barcoded-NP-antigen-MHC complex and its use for capturing antigen-specific T cells.

Compositions can include antigen-MHC complexed with a barcoded nanoparticle (NP) agent to form a barcoded NP-antigen-MHC complex. Formation of an exemplary antigen-specific MHC tetramer bound to a DNA linker (i.e., an antigen-MHC complex) to be linked with a nanoparticle is schematically shown in FIG. 1A. The barcoded NP-antigen-MHC complex can be modular in form as schematically shown in FIG. 1B. The exemplary barcoded NP-antigen-MHC complex is made of an antigen-MHC complex (e.g., the MHC display moiety comprising at least one antigenic peptide") (FIG. 1A) and a barcoded NP complex linked together by polynucleotide hybridization domains. The barcoded polynucleotides comprises a defined barcode sequence to identify the antigen in the antigen-MHC complex (also referred to herein as a neoantigen identifier or "NI"). In addition, the barcoded polynucleotides can comprise either a T cell receptor (TCR) a primer sequence ("Cα") or a TCRβ primer sequence ("CB"). The primer sequences are complementary to TCRα and TCRβ RNA transcripts, respectively. The barcoded polynucleotides can also comprise a universal target sequence ("UP1"). The universal target sequence can be a polymerase chain reaction (PCR) primer target sequence. The universal target sequence can also be any sequence that allows for barcoding, such as a target that is complementary to a fluorescent nucleotide probe or allows for capturing to a solid substrate.

In other examples, primer sequences to TCRγ and TCRδ can be used instead of TCRα and TCRβ. Specifically, the barcoded NP-antigen-MHC complex comprises (a) an MHC display moiety comprising at least one antigenic peptide, (b) a first single-stranded polynucleotide sequence, the first sequence comprising in a 5' to 3' orientation: 1) a universal target sequence; 2) a unique, defined barcode sequence, wherein the defined barcode sequence is operably associated with the identity of the antigenic peptide; and 3) a TCRγ primer sequence, wherein the TCRγ primer sequence is complementary to a TCRγ RNA transcript; and c) a second single-stranded polynucleotide sequence, the second sequence comprising in a 5' to 3' orientation: 1) the universal target sequence; 2) the defined barcode sequence; and 3) a TCRδ primer sequence, wherein the TCRδ primer sequence is complementary to a TCRδ RNA transcript; and d) the at least one particle; and wherein the MHC display moiety, the first single-stranded polynucleotide sequence, and the second single-stranded polynucleotide sequence are attached, with or without a linker, to the particle. The various properties described herein for the barcoded NP-antigen-MHC complexes comprising TCRα and TCRβ primer sequences are applicable in all instances to barcoded NP-antigen-MHC complexes comprising TCRγ and TCRδ primer sequences.

The components of the NP-barcoded NACS library are not shown to scale. The nanoparticle itself is much larger than the DNA-labeled tetramers or barcoded polynucleotides, so that each nanoparticle can have, e.g., up to $10^5$ identical antigen-MHC complexes and $10^3$ or more of each of the barcoded polynucleotides attached. This complex can also be referred to as a nanoparticle sorting agent, methods of using the complex can be referred to as nanoparticle-barcoded nucleic acid cell sorting (NP-barcoded NACS), and a collection of complexes can be referred to as an NP-barcoded NACS library. Each library element can be prepared separately, and designed so that each antigen is associated with a unique barcode.

NP-barcoded NACS is a parallel method for searching through a heterogeneous mixture of lymphocytes for a group of antigen-specific T cell populations, which are then separated from the mixture. Once separated, the invention allows for the antigen-specificity of each individual T cell to be assigned by downstream sequencing of the barcode. The invention also allows correct pairing of the expressed TCRα and TCRβ sequences to identify the antigen specific TCR for each individual T cell following sequencing.

Additional description of exemplary capture agents and related methods and systems for detecting and/or sorting antigen-specific T cells is found in U.S. Pat. No. 8,394,590 and US Publication No. 2017/0003288, each of which are incorporated by reference herein in its entirety. Specifically, U.S. Pat. No. 8,394,590 describes the construction of a library of DNA-labeled antigen-major histocompatibility complex (MHC) tetramers, and US 2017/0003288 describes coupling of the DNA-labeled tetramers to DNA-functionalized magnetic nanoparticles to prepare the NP-barcoded NACS library. Additionally, PCT/US17/59598 describes separating and capturing antigen-specific T cells using DLD arrays. Each of the modular components of the barcoded NP-antigen-MHC complex is described in more detail below.

Nanoparticles

As used herein, "nanoparticles" or alternatively "particles" refer to substrates capable of being specifically sorted or isolated, and to which other entities can be attached. In some embodiments, the nanoparticle is magnetic, e.g., for isolation using a magnet. In some embodiments, the magnetic nanoparticle comprises magnetic iron oxide. Examples of magnetic particles include, but are not limited to, Dynabeads™ (Thermo Fisher). In some embodiments, the nanoparticle is a polystyrene particle, e.g., for isolation by gravity. In other embodiments, the particle can be a surface, a bead, or a polymer. Examples of beads include, but are not limited to, agarose beads and SEPHAROSE beads. In particular embodiments, the particle or nanoparticle can be fluorescent or attached to a fluorophore directly or indirectly.

According to certain embodiments, the nanoparticle is modified with an attachment moiety for attaching additional, such as polynucleotides including the polynucleotide hybridization domain and the barcoded polynucleotides comprising the defined barcodes sequences. Modification of the nanoparticle includes an attachment moiety that can pair with (e.g., covalently bind to) a corresponding cognate (e.g., complementary) attachment moiety attached to polynucleotides. Any suitable pair of attachment moieties may be used to modify the nanoparticle and the polynucleotide detection tag for attachment. Non-limiting examples of attachment moiety pairs include a streptavidin/biotin system, a thiol group (e.g., cysteine) and maleimide, adamantane and cyclodextrin, an amino group and a carboxy group, and an azido group and alkynl group. In some embodiments, the attachment moiety can comprise a cleavage moiety. In other embodiments, the attachment moiety bound to complementary cognate attachment moiety can be reversible, such as a reducible thiol group. In an exemplary embodiment, the modified nanoparticle is a streptavidin coated magnetic nanoparticle, such as 1 μm nanoparticles (e.g., Dynabeads™ MyOne™ Streptavidin T1 beads from ThermoFisher Scientific), and the polynucleotides can be biotinylated for attachment to the modified nanoparticle.

NP-Antigen-MHC Complex

Each antigen, from an NP-barcoded NACS library, can potentially be recognized by, and bind to, a specific T cell, by interacting with the T cell receptor. The antigen can be prepared so that it can be recognized by the T cell receptor that defines the T cell population of interest. It can also be prepared so that it is attached to a magnetic nanoparticle (NP). In this way, once the antigen-specific T cells bind to the antigen, those T cells can be separated from the mixture using a magnet. In some embodiments, computational analysis of a cancer patient's tumor genome can be used to define a series of candidate neoantigens used to build the NP-barcoded NACS library. Additional description of methods to identify neoantigens can be found in US Publication No. 2017/0003288, US Publication No. 2017/0199961, and issued U.S. Pat. No. 9,115,402, each incorporated by reference in their entirety.

An MHC display moiety can include a recombinant MHC molecule. The MHC display moiety can bind peptide antigens to form an antigen-MHC complex such that the antigens are capable of recognition by a cognate TCR molecule. In some embodiments, the MHC complex can be an MHC Class I (MHC I) complex that pairs with CD8-positive (CD8+) T "killer" cells. In other embodiments, the MHC complex can be an MHC Class II (MHC II) complex that pairs with CD4+ "helper" T cells. In some embodiments, the recombinant MHC molecule is an MHC Class II molecule expressed and loaded with a candidate antigen peptide as described in Novak et al., 1999, J. Clin. Invest. 104: R63-R67, the entire contents of which are herein incorporated by reference. Additional description of types of MHC molecules that can be used can be found in US Publication No. 2017/0003288. In certain embodiments, an MHC display moiety can comprise an attachment moiety, including the MHC display moiety being directly biotinylated.

In some embodiments, the MHC display moiety is an MHC Class I molecule expressed with a conditional ligand. As the MHC class I molecule is unstable in the absence of peptide (i.e. antigen peptide), a recombinant MHC Class I molecule is expressed with a cleavable peptide, that upon irradiation with UV light dissociates from the complex and disintegrates. However, if the UV disintegration of the cleavable peptide is performed in the presence of a "rescue peptide," the rescue peptide will readily replace the UV irradiated peptide in the binding groove, as described in Toebes et al., 2006, *Nat. Med.* 12:246-251 and Bakker et al., *PNAS*, 2008, 105:3825-3830, the entire contents of both of which are herein incorporated by reference. Using this technology, several assembled MHC Class I molecules can be loaded with candidate antigens, including neoantigens, to form a MHC class I antigen library for screening T cells.

In other embodiments, the MHC display moiety is a single chain trimer. Single-chain trimers are described in more detail in US Publication No. 2003/0003535, US Publication No. 2009/0117153, and US Publication No. 2008/0219947, each of which are incorporated by reference herein in its entirety. Briefly, as used herein, "single chain trimers" refer to recombinant MHC molecules expressed as a single polypeptide fusion of an antigen peptide, a β2-microglobulin, and a MHC class I heavy chain comprising the α1, α2, and α3 domains. In certain embodiments, single-chain trimers can comprise disulfide traps, as described in US Publication No. 2009/0117153 and US Publication No. 2008/0219947.

In some embodiments, an MHC display moiety is a tetramer complex of four MHC molecules each loaded with the same candidate antigen. Since neoantigens can have low binding affinities ($K_d$) for MHC proteins (e.g., 500 nM or lower) a tetrameric MHC complex allows for increased binding avidity, thereby increasing the sensitivity of this antigen-MHC tetrameric probe for pairing with low abundance cognate T cells.

In some embodiments, an MHC tetramer is formed using modified streptavidin conjugated with four biotin-modified MHC molecules. The streptavidin can also be modified to enable attachment of a polynucleotide (e.g., DNA or RNA) linker, e.g., a polynucleotide hybridization domain. Modification of the streptavidin can include an attachment moiety that can pair with (e.g., covalently bind to) a corresponding cognate attachment moiety attached to the polynucleotide linker. Any suitable pair of attachment moieties may be used to modify streptavidin and the polynucleotide linker for attachment. Non-limiting examples of attachment moiety pairs include a thiol group (e.g., cysteine) and maleimide, adamantane and cyclodextrin, an amino group and a carboxy group, and an azido group and alkynl group (i.e., click chemistry). An example of a cysteine-modified streptavidin ("SAC") attached to a maleimide-modified polynucleotide hybridization domain (the "DNA-cys-Strep" also referred to as "DNA-SAC") is shown in FIG. 1A. Biotinylated MHC display moieties complexed with antigen peptides are then bound to the DNA-cys-Strep to form MHC tetramers as exemplified in FIG. 1A (the "DNA-labeled tetramer").

In other embodiments, the MHC display moiety is a trimer complex of three MHC molecules each loaded with the same candidate antigen. In specific embodiments, the trimer complex can also be complexed with a fluorophore (also referred to as a fluorochrome). Fluorophore-MHC trimer complexes are described in more detail in Bethune et al., *BioTechniques* 62:123-130 Mar. 2017, herein incorporated by reference for all it teaches.

According to certain embodiments, a polynucleotide hybridization domain is attached to the barcoded NP, and a second polynucleotide hybridization domain is attached to the streptavidin scaffold of the antigen-MHC complex. The first and second polynucleotide hybridization domain cans be sufficiently complementary, including being the reverse complement of each other, to hybridize. Accordingly, the antigen-MHC complex is linked to a barcoded nanoparticle through hybridization of complementary hybridization domains. In some embodiments, the first polynucleotide hybridization domain and the second polynucleotide hybridization domain may be single stranded DNA (ssDNA) having a first and a second hybridization sequence, respectively, where the first and second hybridization sequences are complementary, resulting in a linker of hybridized double stranded DNA (dsDNA), e.g., as shown as overlapping black lines in FIG. 1B.

In particular embodiments, the cleavable peptide is replaced by the antigen of interest before the antigen-MHC complex is linked to the barcoded nanoparticle. In other embodiments, an antigen-MHC complex is linked to a barcoded nanoparticle with the cleavable peptide still bound to the MHC. This can be used to generate a library of barcoded nanoparticles with MHCs that can subsequently have the cleavable peptide released, e.g., the barcoded nanoparticle library irradiated, and replaced by an antigen of interest.

Barcoded Polynucleotides

Embodiments can include a modified nanoparticle attached to barcoded polynucleotides comprising a defined barcode sequence. In some embodiments, the barcoded polynucleotides is a polynucleotide that provides a unique antigen-specific sequence for identification after T cell isolation. Therefore, each unique antigen-MHC complex is attached (i.e., hybridized) to a nanoparticle with a unique defined barcode sequence. This allows an operative association between a given antigen and a given barcode that is unique to the pair.

In some embodiments the barcoded polynucleotides are ssDNA. In some embodiments, the polynucleotides comprising the barcodes are modified at their 5' end to comprise an attachment moiety for attachment to a nanoparticle. For example, the polynucleotides comprising the barcode sequences are conjugated to a biotin molecule for binding to a streptavidin-nanoparticle; however any suitable attachment moiety may be used.

As described herein and as understood by a person skilled in the art, suitable attachment moiety pairs are known in the art. Non-limiting examples of attachment moieties include thiol, maleimide, adamantane, cyclodextrin, amine, carboxy, azide, and alkyne.

In some embodiments, the polynucleotide sequences are modified at their 5' end to include a cleavage moiety. Subsequent to attachment of the polynucleotide sequences to a nanoparticle, the cleavage moiety allows for release of the barcoded polynucleotides from the nanoparticle. For example, following isolation of a T cell associated with the barcoded NP-antigen-MHC complex, the barcoded polynucleotides can be cleaved (i.e., released) from the nanoparticle complex. In certain embodiments, the cleavage moiety is a photocleaveable moiety, such as UV cleavable moieties. An example of a UV cleavable linker is a biotin modification with a photocleavable group having the formula shown below ("5PCBio", synthesized by IDT):

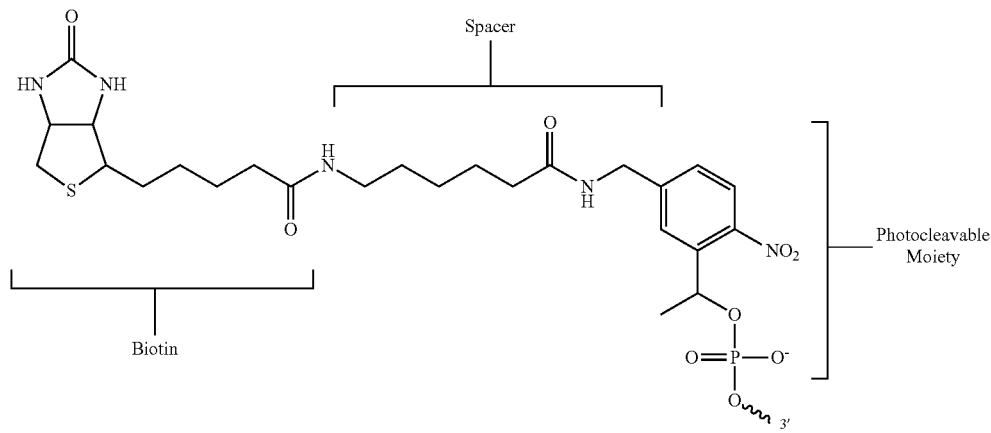

<www (dot) idtdna (dot) com/pages/education/decoded/article/which-biotin-modification-to-use-> (retrieved Mar. 1, 2018)

In other embodiments, the cleavage moiety can comprise a reversible group, such as a reducible thiol group. Examples of cleavage moieties using reversible groups are described in US Publication No 2015/0376609, herein incorporated by reference.

According to embodiments and shown in FIG. 1B, the barcoded polynucleotides comprise three elements: (1) a universal PCR primer target sequence (UP1), (2) a defined barcode sequence (NI), and (3) a TCR primer sequence (Cα or Cβ). The elements are oriented in a 5' to 3' orientation of UP1-NI-Cα/Cβ.

When a NP-barcoded NACS library element binds to a T cell, the nanoparticle complex is also attached to the T cell. Such a T cell is said to be 'barcoded.' All barcoded T cells can thus be separated from the other non-barcoded T cells using magnetic separation techniques, if the nanoparticle is magnetic, or fluorescence-activated cell sorting (FACS) techniques, such as when the nanoparticle or complex is fluorescent or non-magnetic.

Purification of Antigen-Specific T Cells

Various embodiments include use of a barcoded nanoparticle-antigen-MHC complex for screening antigen-specific T cells. As understood by a person skilled in the art, a single antigen may be assayed using the complex in the presence of T cells. However, assaying one candidate antigen is typically not as efficient as screening multiple candidate antigens in a multiplex fashion.

According to some embodiments, isolation and identification of patient-derived and antigen-specific T cells using a library of barcoded-NP-antigen-MHC complexes includes incubating the candidate antigen complexes with patient-derived T cells. In some embodiments, T cells are prepared using standard methods that start from a tissue such as blood, a lymph node, or a tumor.

In some embodiments, patient-derived T cells are isolated from the patient's peripheral blood mononuclear cells (PBMCs) or tumor infiltrating lymphocytes (TILs). In some embodiments, both CD4+ and CD8+ T cells are labeled and sorted from PBMCs or TILS using anti-CD4 and anti-CD8 fluorescent antibodies with live populations of CD4+ and CD8+ single-positive cells sorted using fluorescence-activated cell sorting (FACS), to isolate only CD4+ or CD8+ cells. In some embodiments, T cells that are positive for both CD4 and CD8 may be isolated using an anti-CD3 fluorescent antibody followed by FACS. A person skilled in the art is able to determine the type of T cells to isolate for the type or types of antigen-MHC complex being used.

Embodiments include incubating a barcoded NP-antigen-MHC complex library with a suspension of CD4+, CD8+ or CD4+/CD8+ T cells. Each library element is separately prepared (FIG. 1B), but then all library elements are combined and mixed with a single cell suspension of T cells. Incubation of the nanoparticle library with the T cell suspension allows for a complete and thorough exposure of the nanoparticle-bound antigen to the various T-cell receptors. This method may include rocking or rotation of the cells.

Following incubation of the antigen complex and the T cells, the nanoparticle is selectively separated or selectively collected. Barcoded T cells will likely be bound to many identical copies of identical NP-barcoded NACS library elements, and can be separated based on these interactions. For example, if the nanoparticle is magnetic, applying a magnet to the suspension allows for separation of nanoparticles in a complex with antigen paired T cells and removal of unpaired T cells. An example of multiple distinct barcoded NP-antigen-MHC complexes bound to specific T cells ("NP bound T cells T1, T2, and T3") and capable of magnetic isolation is shown schematically in FIG. 1B. Alternatively, if the nanoparticle is a polystyrene nanoparticle, the unpaired T cells may be separated by gravity (e.g., centrifugation). After removal of unpaired T cells, in some embodiments, the separated bound nanoparticles are washed at least once to remove any non-specifically associated T cells. In other embodiment, the nanoparticle complex contains a fluorophore that enables single-cell fluorescent associated cell sorting (FACS) to sort T cells. In some embodiments, a combination of separation techniques can be used, e.g., magnetic separation can be followed by FACS sorting, or vice versa.

A full NP-barcoded NACS library may include 5-1000 different antigens, each with their own DNA barcode ("NI"), although a 50-element library is typical. T cells can range from 8-20 micrometers in diameter. In some embodiments, the magnetic nanoparticles used in the library are around 1 micrometer in diameter. Each antigen-specific T cell can have many copies of an identical T cell receptor (TCR), so that an antigen-specific T cell can potentially be barcoded by many identical copies of a specific NP-barcoded NACS library element. In one embodiment, the T cells will appear dark in color when barcoded by magnetic nanoparticles, since the nanoparticles themselves can be black.

For a sample of tumor infiltrating lymphocytes (TILs) or Peripheral Blood Mononuclear Cells (PBMCs) that contains $10^4$ CD8+ T cells, and for a (typical) NP-barcoded NACS library size of 50, often between 5 and 200 T cells will be barcoded by between 1 and 15 of the 50 library elements. Because the T cell receptor interaction with the antigens is highly specific, each individual barcoded T cell will only be associated with a single library element, although multiple copies of that library element can (and will likely) be attached to the T cell. Each barcoded T cell will thus be associated with between 1-400 nanoparticles. In some embodiments, isolation of T cells require multiple copies of that library element to be attached, e.g., for fluorescent complexes, wherein isolation requires a sufficient signal for isolation. In other embodiments, isolation requires binding to variations of the same barcoded-NP-antigen-MHC complex with the same barcode, but other variations in the complex, e.g., different fluorophores, and isolation is determined by binding to fluorescent complexes with the same barcode (NI) and antigen but different fluorophores. Approximately $10^8$ nanoparticles, representing the 50 NP-barcoded NACS library elements, might be mixed with the $10^4$ T cells in the barcoding process. Unbound NP-barcoded elements can outnumber the barcoded T cells by about $10^6:1$ or more.

Microfluidic Device for Separation and Isolation

After magnetic separation of barcoded T cells from unbound T cells, the population comprising barcoded T cells can also include captured barcoded nanoparticles that are not bound to T cells. When the barcoded nanoparticles have a plurality of distinct barcodes, this could generate many false positive signals unless the unbound nanoparticles are separated from the T cell bound nanoparticles. However, there are typically a vast number of unbound nanoparticles relative to the nanoparticles bound to the T cells. Therefore, in order to correctly read out the DNA barcodes on the barcoded T cells, or to do further analysis of those T cells, it is desirable to completely separate the barcoded T cells from the excess nanoparticles. This represents a challenging separation problem. Provided herein is a device and a high throughput method to separate bound and unbound nanoparticles (i.e., separating barcoded T cells from barcoded nanoparticles that are not bound to T cells).

Provided herein, according to some embodiments, is a microfluidic device that performs two key functions. First, the unattached nanoparticles are spatially separated from the barcoded T cells with a high fidelity (e.g., 100% fidelity). Second, the barcoded T cells are isolated into individual single cell droplets or for subsequent processing and analysis. In some embodiments, the analysis assigns expressed TCRα and TCRβ genes (i.e., a TCR) for each individual isolated T cell to be assigned to a specific antigen. In some embodiments, two separate microfluidic devices are used to perform the two key functions described.

Deterministic Lateral Displacement (DLD) Array

In some embodiments, the microfluidic device uses the principle of deterministic lateral displacement (DLD) to separate, in a flowing solution of particles and solvent, particles according to the particle size. In other words, the invention takes advantage of the size difference of a T cell (8-20 micrometers diameter) relative to an unbound NP-antigen-MHC complex (~1 micrometer) to separate barcoded T cells. Once separated, the barcoded T cells are isolated in single-cell droplets in preferred embodiments using a droplet generator attached directly to the DLD array containing device, or in other embodiments a separate droplet generating device.

Figure 3:
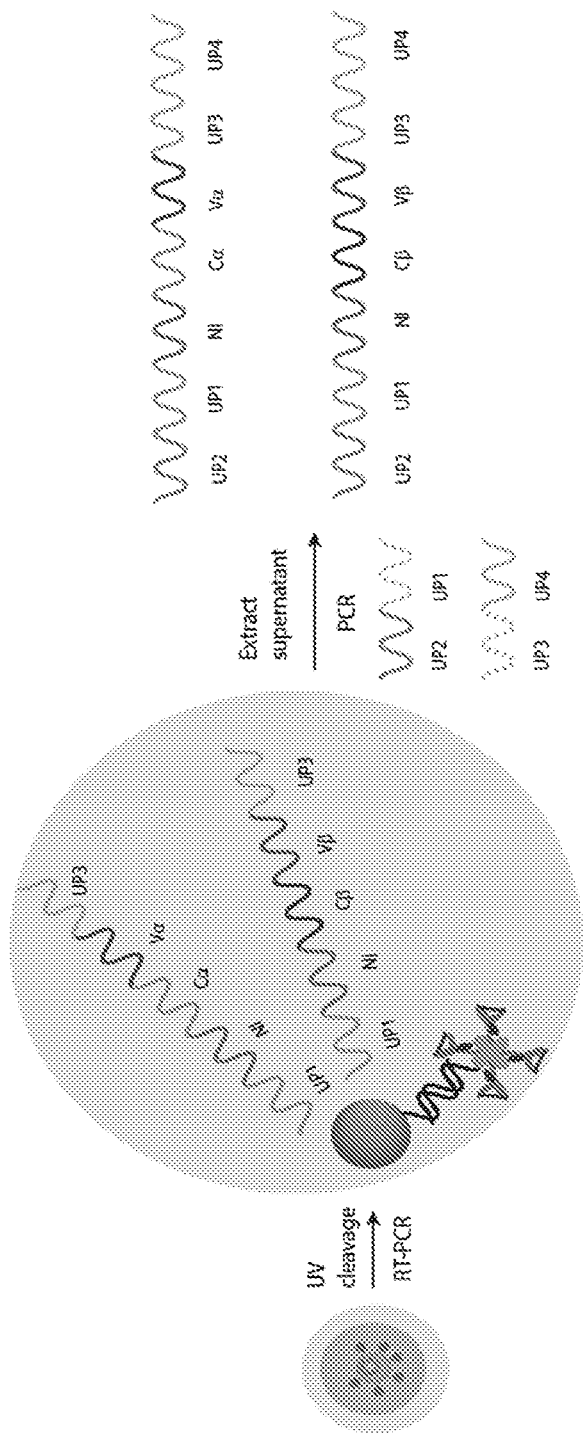
FIG. 3 illustrates the general amplification strategy for generating the final sequencing product.

DLD arrays (also known as "obstacle array") devices have been described, and their basic operation is explained, for example in U.S. Pat. No. 7,150,812, which is incorporated herein by reference in its entirety. Referring to FIGS. 3 and 4 of U.S. Pat. No. 7,150,812, a DLD array can operate essentially by segregating particles passing through an array (generally, a periodically-ordered array) of obstacles, with segregation occurring between particles that follow an "array direction" that is offset from the direction of bulk fluid flow or from the direction of an applied field.

Figure 8:
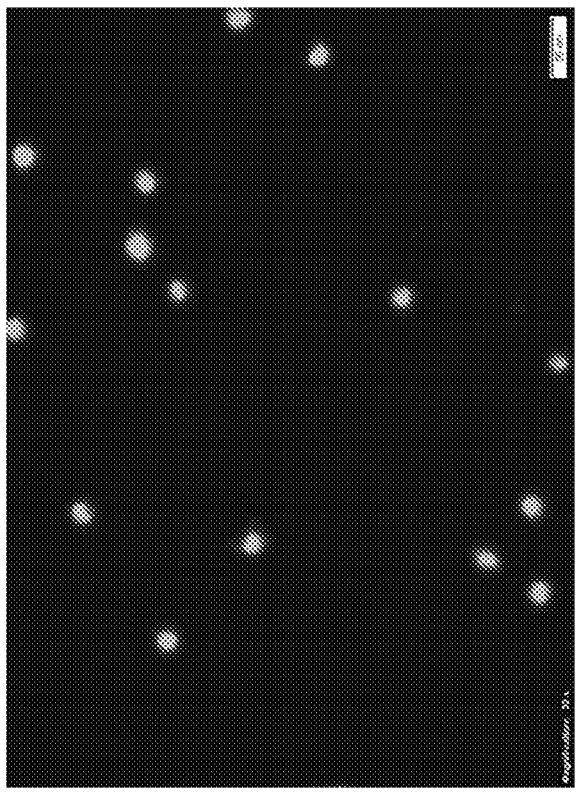
FIG. 8 shows microscope images of cells using fluorescence (right panel) or brightfield images (left panel).
Figure 8:
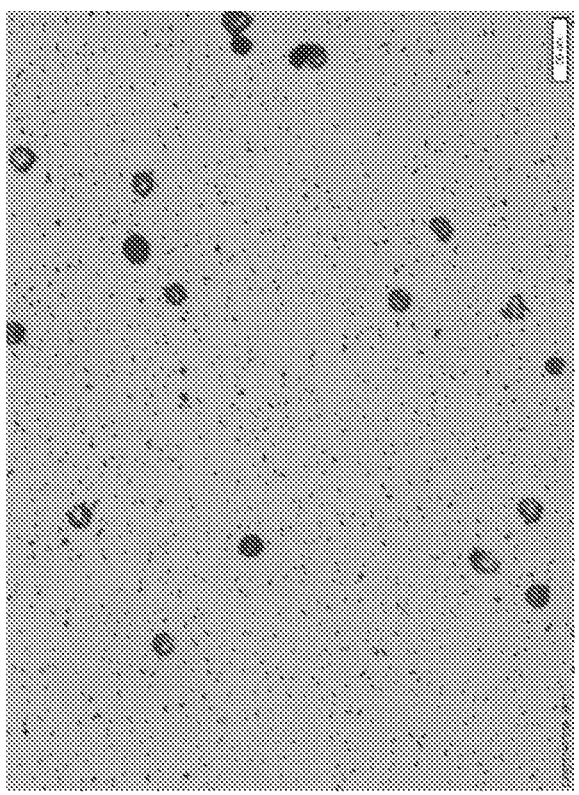

At the level of flow between two adjacent obstacles under conditions of relatively low Reynold's number, fluid flow can occur in a laminar fashion. Considering the volumetric flow between two obstacles in hypothetical layers (e.g., modeling the flow by considering multiple adjacent stream tubes of equal volumetric flow between the obstacles, as shown in FIG. 8 of U.S. Pat. No. 7,150,812), the likelihood that fluid in a layer will pass on one side or the other of the next (i.e., downstream) obstacle can be calculable by standard methods (see, e.g., Inglis et al., 2006, Lab Chip 6:655-658). For an ordered array of obstacles offset from the direction of bulk fluid flow, the arrangement of the obstacles can define an array direction corresponding to the direction in which the majority of fluid layers between two obstacles travels. A minority of fluid layers can travel around the downstream obstacle in a direction other than the array direction.

The path that a particle passing between the two obstacles can take can depend on the flow of the fluid in the layers occupied by the particle. Conceptually, for a particle having a size equal to one of the hypothetical fluid layers described in the preceding paragraph, the particle can follow the path of the fluid layer in which it occurs, unless it diffuses to a different layer. For particles larger than a single fluid layer, the particle can take the path corresponding to the majority of the fluid layers acting upon it. Particles having a size greater than twice the sum of the thicknesses of the minority of layers that travel around a downstream obstacle in the direction other than the array direction can be acted upon by more fluid layers moving in the array direction, meaning that such particles will travel in the array direction. This concept is also illustrated in FIGS. 5-11 of U.S. Pat. No. 7,150,812. Thus, there can be a "critical size" for particles passing between two obstacles in such an array, such that particles having a size greater to that critical size can travel in the array direction, rather than in the direction of bulk fluid flow and particles having a size less than the critical size can travel in the direction of bulk fluid flow. Particles having a size precisely equal to the critical size can have an equal chance of flowing in either of the two directions. By operating such a device at a high Peclet number (i.e., such that advective particle transport by fluid layers greatly outweighs diffusive particle between layers), the effects of diffusion of particles between fluid layers can be ignored.

Devices for separating particles based on size and/or using DLD are described, e.g., in U.S. Pat. Nos. 7,150,812, 7,318,902, 7,472,794, 7,735,652, 7,988,840, 8,021,614, 8,282,799, 8,304,230, 8,579,117, and PCT Publication No. WO2012/094642, which are incorporated by reference herein in their entireties.

Described herein are devices comprising a DLD array that are useful for segregating particles by size. In one embodiment, a device includes a body defining a microfluidic flow channel for containing fluid flow. An array of obstacles is disposed within the flow channel, such that fluid flowing through the channel flows around the obstacles. The obstacles extend across the flow channel, generally being either fixed to, integral with, or abutting the surface of the flow channel at each end of the obstacle.

The obstacles can be arranged in rows and columns, in such a configuration that the rows define an array direction that differs from the direction of fluid flow in the flow channel by a tilt angle (θ) that has a magnitude greater than zero. The maximum operable value of θ can be ⅓ radian. The value of c can be preferably ⅕ radian or less, and a value of ⅒ radian has been found to be suitable in various embodiments of the arrays described herein. The obstacles that are in columns define gaps between themselves, and fluid flowing through the flow channel is able to pass between these gaps, in a direction that is generally transverse with respect to the columns (i.e., generally perpendicular to the long axis of the obstacles in the column and generally perpendicular to a plane extending through the obstacles in the column).

The obstacles can have shapes so that the surfaces (upstream of, downstream of, or bridging the gap, relative to the direction of bulk fluid flow) of two obstacles defining a gap are asymmetrically oriented about the plane that extends through the center of the gap and that is parallel to the direction of bulk fluid flow through the channel. That is, the portions of the two obstacles can cause asymmetric fluid flow through the gap. The result can be that the velocity profile of fluid flow through the gap is asymmetrically oriented about the plane. As a result of this, the critical particle size for particles passing through the gap adjacent to one of the obstacles can be different than the critical particle size for particles passing through the gap adjacent to the other of the obstacles.

The obstacles can be solid bodies that extend across the flow channel, in some cases from one face of the flow channel to an opposite face of the flow channel. Where an obstacle is integral with (or an extension of) one of the faces of the flow channel at one end of the obstacle, the other end of the obstacle can be sealed to or pressed against the opposite face of the flow channel. A small space (preferably too small to accommodate any of particles of interest for an intended use) can be tolerable between one end of an obstacle and a face of the flow channel, provided the space does not adversely affect the structural stability of the obstacle or the relevant flow properties of the device. In some embodiments described herein, obstacles are defined by a cross-sectional shape (e.g., circular, "I-shaped," round, or triangular). Methods of imparting a shape to an obstacle formed from a monolithic material are well known (e.g., photolithography and various micromachining techniques) and substantially any such techniques may be used to fabricate the obstacles described herein. The sizes of the gaps, obstacles, and other features of the arrays described herein depend on the identity and size of the particles to be handled and separated in the device, as described elsewhere herein. Typical dimensions are on the order of micrometers or hundreds of nanometers, but larger and smaller dimensions are possible, subject to the limitations of fabrication techniques.

The obstacles can generally be organized into rows and columns (use of the terms rows and columns does not mean or imply that the rows and columns are perpendicular to one another). Obstacles that are generally aligned in a direction transverse to fluid flow in the flow channel can be referred to as obstacles in a column. Obstacles adjacent to one another in a column can define a gap through which fluid flows. Obstacles in adjacent columns can be offset from one another by a degree characterized by a tilt angle, designated θ (theta). Thus, for several columns adjacent to one another (i.e., several columns of obstacles that are passed consecutively by fluid flow in a single direction generally transverse to the columns), corresponding obstacles in the columns can be offset from one another such that the corresponding obstacles form a row of obstacles that extends at the angle ε relative to the direction of fluid flow past the columns. The tilt angle can be selected and the columns can be spaced apart from each other such that 1/θ (when θ is expressed in radians) is an integer, and the columns of obstacles repeat periodically. The obstacles in a single column can also be offset from one another by the same or a different tilt angle. By way of example, the rows and columns can be arranged at an angle of 90 degrees with respect to one another, with both the rows and the columns tilted, relative to the direction of bulk fluid flow through the flow channel, at the same angle of θ.

Microfluidic Devices for Separation of Unbound Nanoparticles and Barcoded T cells In some embodiments, provided herein is a microfluidic device comprising a separation channel. The separation channel comprises an array of obstacles adapted to disperse particles having a size at or above a critical size in a differential manner deviating from the average flow direction in a flow of a heterogeneous fluid sample through the separation channel. In certain embodiments, the particles having a size at or above the critical size comprise a nanoparticle bound to a cell, and the particles having a size less than the critical size comprise an unbound nanoparticle. In specific embodiments, the cell is a T cell.

The array of obstacles are based on the principles of deterministic lateral displacement (DLD), and are designed to offer continuous separation, focusing, and separation of the barcoded T-cells for the analysis of antigen specific T cells, e.g., neoantigen-specific CD8+ T cells. Firstly, the engineered obstacle array is situated in the device in order to separate the barcoded T-cells (large particles) from the mixture of such T-cells and unattached small nanoparticles (e.g., the unbound barcoded-NP-antigen-MHC complexes) based on the size differential. In some embodiments, this obstacle array comprises a plurality of columns of obstacles and a plurality of rows of obstacles. In some embodiments, the plurality of rows of columns extend at an angle relative to the average flow direction of said separation channel. In some embodiments, the plurality of rows of columns extend at an angle relative to the average flow direction In some embodiments, the plurality of rows of columns extend at an angle relative to the average flow direction through the separation channel of from 1 degree to 15 degrees, from 3 degrees to 12 degrees, from 4 degrees to 8 degrees, or from 5 degrees to 7 degrees, or from 5.5 degrees to 6 degrees.

In some embodiments, the plurality of rows of columns extend at an angle relative to the average flow direction through the separation channel of about 6 degrees.

In some embodiments, the plurality of rows of columns extend at an angle relative to the average flow direction through the separation channel of about 3 degrees, 4 degrees, 5 degrees, 6 degrees, 7 degrees, 8 degrees, 9 degrees, or 10 degrees.

In some embodiments, the rows of obstacles comprises a gap between adjacent rows of from about 8 µm to about 15 µm. In some embodiments, the plurality of rows of obstacles comprises a gap between adjacent rows of from about 10 µm to about 13 µm.

In some embodiments, the plurality of columns of obstacles comprise a gap between adjacent columns of from about 8 µm to about 15 µm. In some embodiments, the plurality of columns of obstacles comprise a gap between adjacent columns of from about 10 µm to about 13 µm.

In some embodiments, the array of obstacles extends into the collection channel. In some embodiments, the array of obstacles extends into the waste channel.

In specific embodiments, the separation channel bifurcates into a collection channel and a waste channel. After flowing through the separation channel, in some embodiments, the separated particles above the critical size (e.g., the barcoded T cells) continuously flow along one wall of the microfluidic channel from the separation channel and plurality of obstacles acting as a DLD array into the collection channel, while particles below the critical size (e.g., the unbound barcoded-NP-antigen-MHC complexes) flow along an opposite wall into the waste channel.

In some embodiments, the collection channel directs particles above the critical size (e.g. cells) towards a droplet generator to encapsulate individual particles with high-efficiency single particle isolation into droplets. In some embodiments, a cell focusing channel connects the collection channel to the droplet generator. The cell focusing channel acts to slow and orderly arrange particles having a size at or above a critical size, e.g., orderly arrange barcoded T cells into a single-cell stream. The ordered arrangement improves the efficiency of isolating only a single cell in a droplet. Flow focusing channels are known to those skilled in the art, an example of which is described in more detail in US Publication No. 2009/0014360, the entirety of which is incorporated by reference.

In alternative embodiments, the collection channel directs particles above the critical size (e.g., the barcoded T cells) towards a collection tube, multi-well plate, other collection device.

Single Cell Droplet Generation

In embodiments of the present invention, following separation of particles using the DLD array described above, particles above the critical size (e.g., the barcoded T cells) are individually isolated in droplets using a droplet generating microfluidic device (i.e., a "droplet generator"). Droplet generating devices used to encapsulate single cells are known to those skilled in the art, e.g., as described in US Publication No. 2006/0079583, US Publication No. 2006/0079584, US Publication No. 2010/0021984, US Publication No. 2015/0376609, US Publication No. 2009/0235990, and US Publication No. 2004/0180346.)

In some embodiments, the particles above the critical size flow from the collection channel, optionally through a cell focusing channel, and into a flow focusing nozzle. The flow focusing nozzle is configured to intersect one or more carrier inlet channels carrying an immiscible carrier fluid such that the immiscible carrier fluid encapsulates single particles (e.g., single cells) generating discrete single particle droplets. Specifically, the particle containing fluid is extruded out of the flow focusing nozzle directly into the immiscible carrier fluid such that the immiscible carrier fluid encapsulates the particle. Droplets containing the single particles then enter into a droplet outlet and collected downstream. It is also to be understood that the current invention contemplates that only a fraction of droplets may comprise a particle, while a fraction or even the majority of the droplets do not comprise a particle. In some embodiments, microfluidic device configuration and/or microfluidic device operational parameters (e.g. flow rates, particle concentration in the sample, etc.) are optimized to reduce the incidence of droplets containing more than one particle, as droplets containing even two particles can compromise downstream sequencing analysis, e.g., the correct paring of TCRα and TCRβ chains with an antigen-specific T cell.

In certain embodiments, the particles are in an aqueous fluid and the immiscible carrier fluid is an oil such that water-in-oil droplets are generated. In some embodiments, the oil can be fluorinated, such as HFE-7500 (3M) or FC40 (Sigma-Aldrich). In specific embodiments, the oil can also comprise fluorinated surfactants to further stabilize droplets, including PEG-PFPE amphiphilic block copolymer surfactant. The surfactant can be added at various concentrations to the oil, typically at about 2-5% w/w. In preferred embodiments, the fluorinated surfactant is a 5% w/w PEG-PFPE amphiphilic block copolymer surfactant. Fluorinated surfactants (also referred to as fluorosurfactants) are described in greater detail in US Publication No. 2010/0105112, herein incorporated by reference in its entirety.

The size and volume of the droplets are important characteristics optimized in the current invention. Droplets that are too large have the potential to be less stable during downstream thermocycling reactions. Droplets that are too small may contain insufficient reagents to generate enough amplified DNA for downstream sequencing analysis. In embodiments of the current invention, the flow focusing nozzle and the carrier inlets are configured to generate discrete droplets of a specific diameter and volume. In some embodiments, the discrete droplets can be 70 micrometers or less, 65 micrometers or less, 60 micrometers or less, 55 micrometers or less, or 50 micrometers or less in diameter. In other embodiments, the droplet is 40-70 micrometers, 40-60 micrometers, or 50-60 micrometers in diameter. In specific embodiments, the droplet is about 55 micrometers in diameter. In other preferred embodiments, the droplets are 30 picoliters to 110 picoliters in volume. In certain embodiments, the discrete droplets can be 30-110 picoliters, 50-100 picoliters, 60-100 picoliters, 70-100 picoliters, 70-90 picoliters, or 75-85 picoliters in volume. In specific embodiments, the discrete droplet is about 80 picoliters in volume.

In some embodiments, the flow focusing nozzle comprises a flow focusing inlet that receives the particle containing fluid which then tapers in diameter to a flow-focusing outlet of a defined diameter, and the particle is extruded from the flow-focusing outlet into the immiscible carrier fluid. The defined diameter of the flow-focusing outlet can be adjusted to generate droplets of different sizes. In some embodiments the distance between the flow focusing inlet and outlet is 30 micrometers in length.

In preferred embodiments, the flow focusing nozzle intersects two carrier inlets at a shared intersection. In some embodiments, the angle of intersection with each carrier inlet is at or approximately at 90 degrees. In this embodiment, immiscible carrier fluid is introduced at the intersection with the flow focusing nozzle from opposing directions and the generated droplet continues in the same fluid path and enters the droplet outlet configured in a linear arrangement with the flow focusing nozzle.

In other embodiments, the flow focusing nozzle intersects one carrier inlet. In some embodiments, the angle of intersection is at or approximately at 90 degrees. In this embodiment, immiscible carrier fluid is introduced at the intersection with the flow focusing nozzle from a single direction and the generated droplet is deflected, e.g. sheared, into the fluid path of the immiscible carrier fluid and enters the droplet outlet configured in a 90 degree or approximately at 90 degree arrangement with the flow focusing nozzle.

In the embodiments of the present invention, the microfluidic device is configured such that additional reagents used in downstream reactions are capable of being encapsulated within the droplet. Reagents include, but are not limited to, lysis reagents, reverse transcription polymerase chain reaction (RT-PCR) reagents, and DNA PCR amplification reagents, described below in greater detail. In preferred embodiments, the microfluidic device is configured to introduce reagents through one or more reagent inlets into the particle containing fluid prior to droplet generation. In some embodiments, the reagent inlet(s) are in fluidic communication with and upstream of the flow-focusing nozzle. In some embodiments, the reagent inlet(s) are downstream of the collection channel and optional cell focusing channel. In some embodiments, the reagents are in a fluid that is miscible with the particle containing fluid. In particular embodiments, microfluidic device configuration and/or microfluidic device operational parameters are adjusted such that the ratio of reagent containing miscible fluid to particle-containing fluid are optimized for DNA yield to facilitate downstream sequencing analysis. In specific embodiments, the ratio is about a 2:1 ratio of miscible fluid to particle-containing fluid.

Following droplet generation, droplets containing single particles (e.g., the barcoded T cells) flow from the droplet outlet to a collection outlet where the droplets are collected in a collection container. As discussed above, droplets that do not contain a particle can also be collected. Collection containers include, but are not limited to, a tube, a PCR tube, a microcentrifuge tube, a test tube, a round-bottom tube, a conical tube, and a multi-well plate. In some embodiments, the collection containers are capable of being thermocycled directly, e.g., a thin-walled PCR tube. In some embodiments, the collection container is physically attached to the collection outlet. In other embodiments, the collection container is not physically attached to the collection outlet, specifically, the collection container is positioned to collect droplets that exit the collection outlet and fall by gravity into the collection container.

In some embodiments, prior to collection, generated droplets pass through a channel or tubing downstream of the droplet outlet. In specific embodiments, the tubing is fabricated from a UV permissible material, examples of which include 500 µm diameter Tygon tubing. In certain embodiments, the droplets dispersed within the tubing are exposed to UV light from a separate light source (not shown). Following UV exposure, droplets are collected in the collection containers described above.

In some embodiments, the droplets can be further sorted, such as further separation or isolation steps based on droplet properties, e.g., fluorescence, magentisism, or size.

Control of Fluid Flow

Control of fluid flow within the microfluidic device is an integral part to the efficient collection of droplets containing single particles having a size at or above a critical size (e.g., barcoded T cells). In embodiments of the present invention, the flow rates through each of the components of the microfluidic device is optimized to maximize efficiency of generating droplets containing at most one particles having a size at or above a critical size. In general, microfluidic devices have a syringe pump attached to each inlet. Thus, in certain embodiments, the microfluidic device comprises a syringe pump attached to each inlet or inlets providing a given fluid, i.e., a pump can be attached to a single inlet providing a fluid, or a pump can be attached to more than one inlet providing the same fluid (e.g., one pump can be attached to the two inlets providing the immiscible carrier fluid).

However, the above strategy of connecting a pump to each inlet can be expensive and can make the microfluidic device more complicated to operate. Thus, in exemplary embodiments, the geometry of the microfluidic device of the present invention in configured to simply design construction and operation by using only two syringe pumps attached to the waste outlet and collection outlet. In specific embodiments, the two syringe pumps are tuned to produce withdrawal flow rates so that only the particles having a size at or above the critical size deflect towards a first wall of the separation channel during flow of the heterogeneous fluid sample through the separation channel, i.e., the efficiency for generating droplets containing only particles having a size at or above the critical size (e.g., barcoded T cells) is maximized. In some embodiments, the syringe pumps generate a vacuum at one or both outlets. In certain embodiments, the pump attached to the waste outlet is adjusted to produce a first withdrawal flow rate, and the pump attached to collection outlet is adjusted to produce a second withdrawal flow rate. In a specific embodiment, the first withdrawal flow rate is different from the second withdrawal flow rate, and that each flow rate is optimized so only the particles having a size at or above the critical size deflect towards a first wall of the separation channel. In specific embodiments, syringes are attached to one or outlets and automated syringe pumps, e.g. a PHD 22/2000 syringe pump (Harvard Apparatus), are attached to each syringe. The syringes can be any size and volume for establishing the flow rates of the invention. In certain embodiments, the syringes attached to each outlet are different sizes and volumes, e.g. a 1 ml syringe attached to the waste outlet and a 60 ml syringe attached to the collection out. However, one skilled in the art can recognize that different syringe sizes and volumes and different syringe pumps can be combined in order to establish a desired fluid flow rate(s).

Exemplary Microfluidic Device

Provided below are exemplary embodiments of microfluidic devices of the present invention, which can be used to separate barcoded T cells from unbound barcoded NP-antigen-MHC complexes (e.g., unattached nanoparticles), and for isolating individual T cells for subsequent analysis or processing in single cell droplets.

Figure 4A:
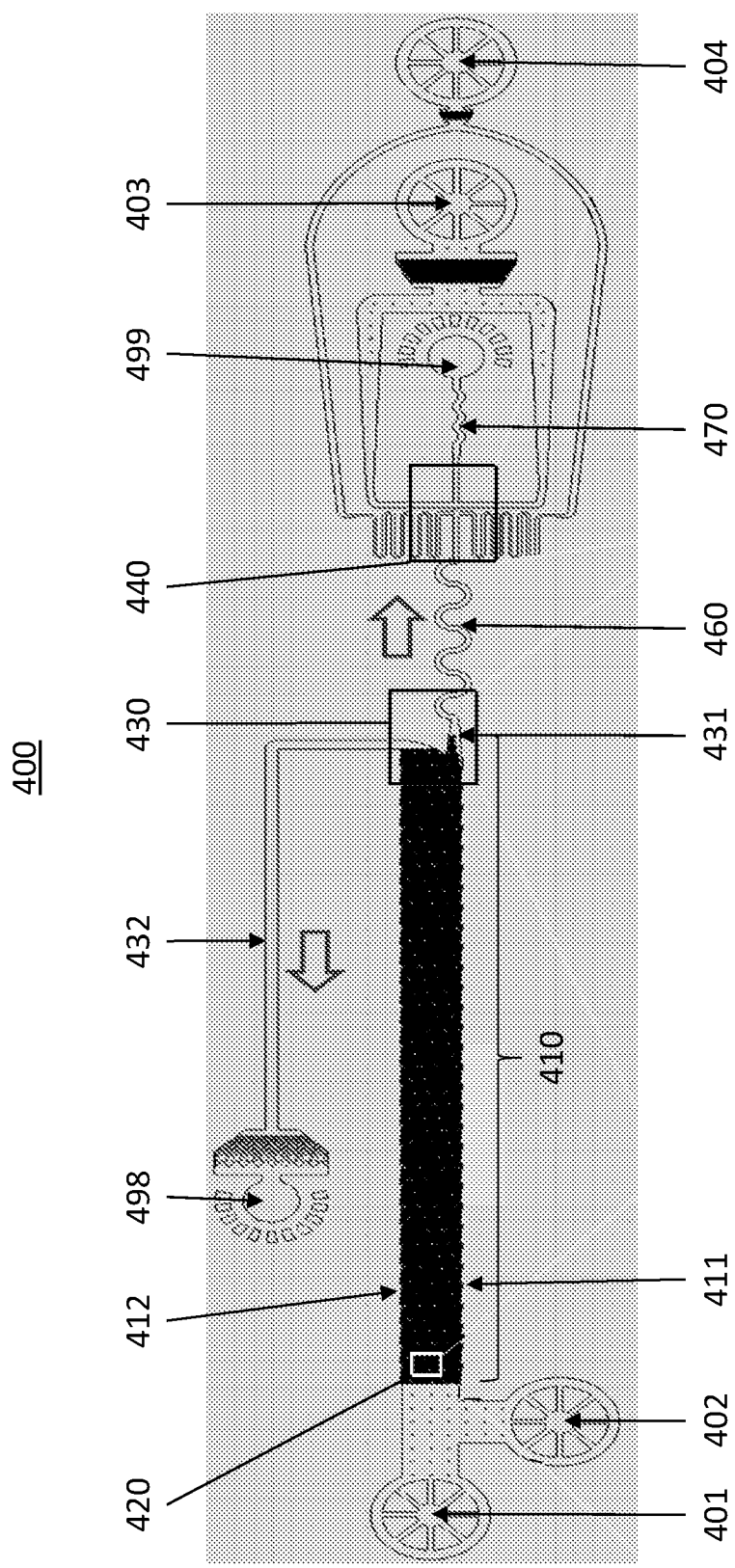
FIG. 4A illustrates a cross-sectional view of a design of a microfluidic device for the separation of barcoded T cells from unattached nanoparticles and isolation in single-cell droplets.

FIG. 4A is a cross-sectional view of a design of a microfluidic device 400 for the separation of barcoded T cells from unattached nanoparticles, according to an embodiment of the invention. As shown, the microfluidic device comprises a sample inlet port 401 and a buffer inlet port 402, an immiscible fluid inlet port 403, a reagent inlet port 404, a collection outlet 499 to collect droplets, and a waste outlet 498 from the chip. The microfluidic device comprises a separation channel 410 that includes DLD arrays 420 (i.e., arrays of obstacles) for the separation of large barcoded cells from unbound nanoparticles. Following the DLD array, the separation channel bifurcates into two paths 430: the top waste channel 432 is for unattached nanoparticles and the bottom collection channel 431 is for barcoded T-cells. The barcoded T-cells are sorted to the bottom wall 411 by the DLD array, then enter a cell-focusing channel 460 with a serpentine structure, where the barcoded T-cells are slowed and orderly arranged into a single-cell stream. The unattached nanoparticles are carried across the top path along the top wall 412 and carried to the waste outlet 498. From the cell-focusing channel, barcoded T cells flow into the droplet generator and isolated into single-cell droplets. The single cell droplets then pass though tubing 470 and exit the microfluidic device at the collection outlet 499.

In order to separate the barcoded T-cells in a buffer solution while leaving the unattached nanoparticles in a sample solution, a DLD array has been designed with an array of obstacles arranged and shaped to efficiently separate barcoded T cells from unbound nanoparticles. Previous papers report that circular pillars are prone to clogging within the gap between the pillars resulting in a drastic reduction in separation efficiency. To resolve this issue, topology optimization has been applied to find optimal structure which would increase the gap between the pillars without scarifying the critical diameter. It has been shown that this new pillar shape allows the gap between the pillars to be increased by 30% compared to the circular pillar shape.

Figure 4B:
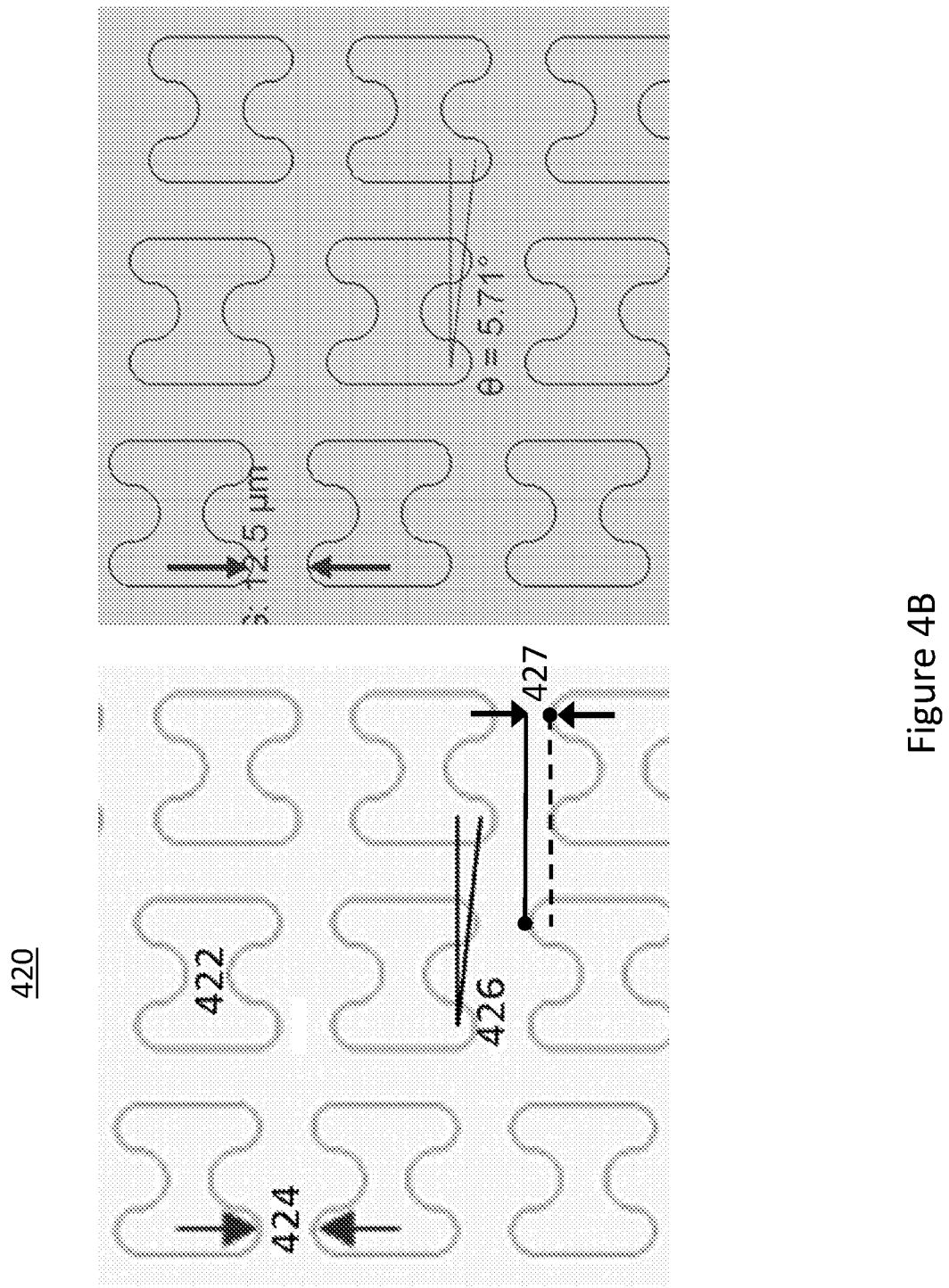
FIG. 4B illustrates an array of obstacles (DLD) used in the microfluidic device to separate unbound nanoparticles and barcoded T cells.

An embodiment of an array of obstacles to use in a microfluidic device as a DLD array 420 to separate unbound nanoparticles and barcoded T cells is illustrated in FIG. 4B. The parameters of the array and the obstacle topology 422 have been optimized to separate T-cells, which are bigger than 4 µm, from unbound nanoparticles smaller than 4 µm (i.e., the critical size is 4 µm). Here, the DLD array uses an "I-shape" pillar design 422. Also as shown in FIG. 4B, obstacles are arranged in rows and columns, and the rows are offset from an average direction of fluid flow in the channel by a tilted angle 426. In some embodiments, the tilted angle 426 is about 6 degrees. The DLD array is also characterized by a gap 424 between adjacent obstacles along a column. In some embodiments, this gap 424 is about 13 µm. The DLD array is also characterized by row shift 427 between adjacent obstacles on a row, which is related to the tilted angle. In some embodiments, the row shift 427 is about 5 µm. FIG. 4B is an enlarged cross-sectional view of the DLD array 420. In the specific embodiments shown here, the DLD array uses an "I-shape" pillar design 422 with 12.5 µm gap 424, 45 µm pitch, and 4.5 µm row shift 427 (i.e. θ[426]=5.71°).

Figure 4C:
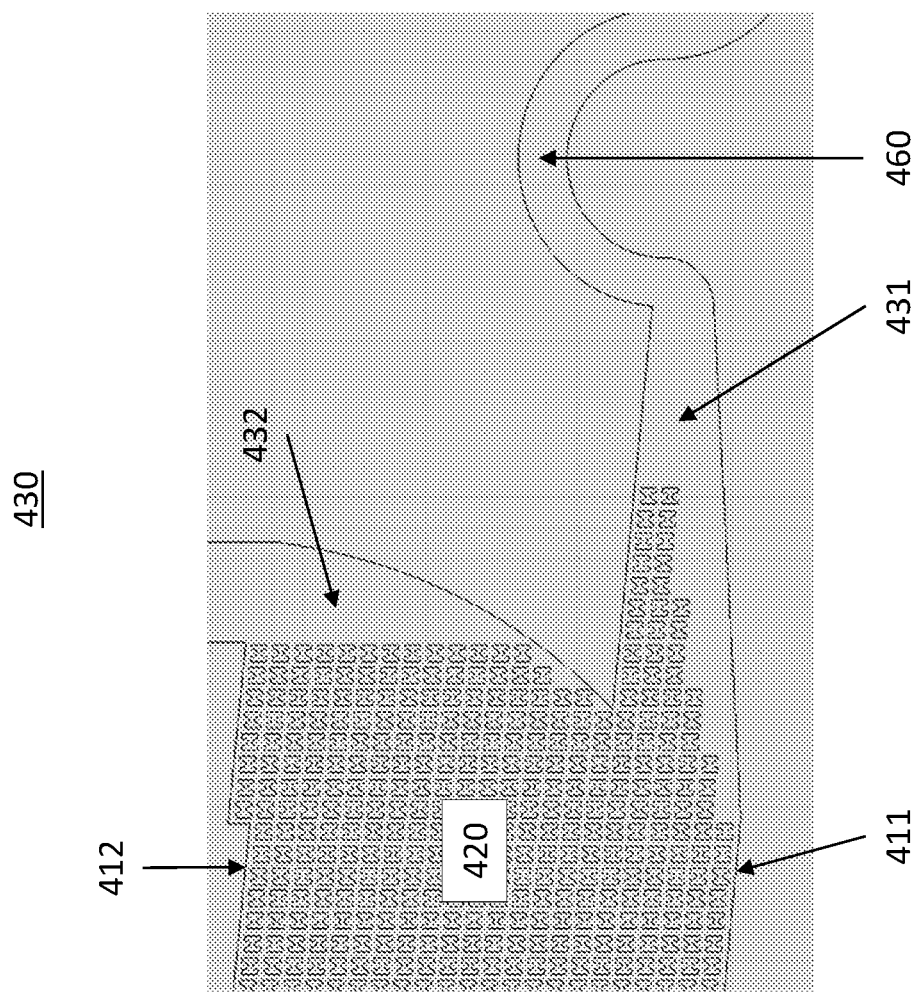
FIG. 4C illustrates an enlarged cross-sectional view of the bifurcation of the separation channel and waste channel following the DLD array.

Following the separation channel 420, the barcoded T-cell are then directed into a separate channel from unbound nanoparticles, i.e., the barcoded T cells are sent to be isolated in single-cell droplets, while unbound nanoparticles are removed from the microfluidic device 400. FIG. 4C is an enlarged cross-sectional view of the bifurcation 430 of the separation channel and waste channel following the DLD array 420. The separation channel bifurcates into a waste channel 432 that shares the top wall 412 of the separation channel, and a collection channel 431 that shares the bottom wall 411. The barcoded T cells are directed to bottom wall 411 by the DLD array 420 and from there flow into the separation channel 431. Subsequently, the cells are directed to the cell focusing channel 460. At the same time, unbound particles flow along the top wall 412 and from there flow into the waste channel 432.

Figure 4D:
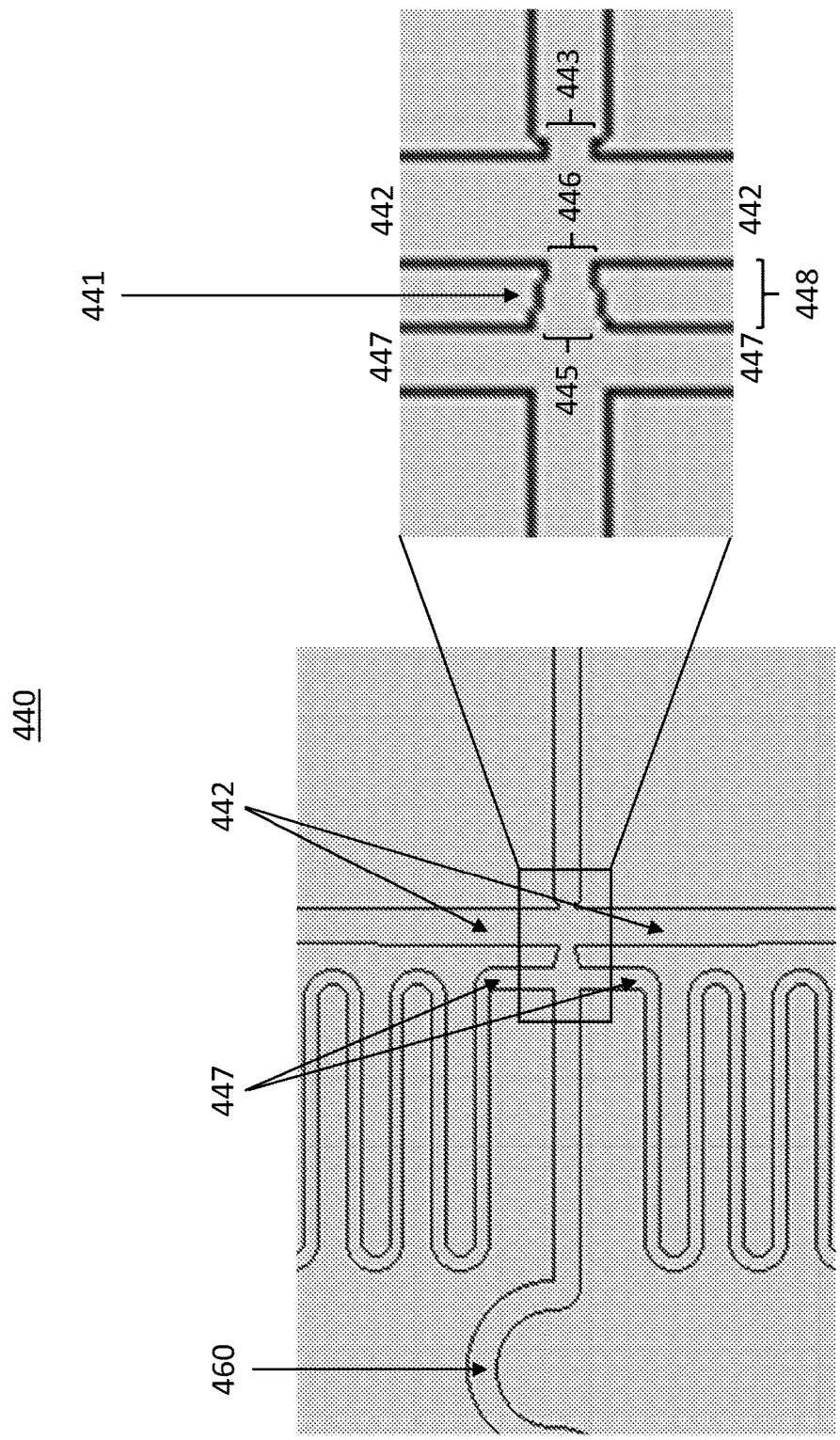
FIG. 4D illustrates an enlarged cross-sectional view of the droplet generator, and the right panel is a further enlargement of the channel intersections within the droplet generator.

The barcoded T cells, once arranged into a single-cell stream by the cell focusing channel 460, enter into the droplet generating device 440. FIG. 4D left panel is an enlarged cross-sectional view of the droplet generator, and the right panel is a further enlargement of the channel intersections within the droplet generator. Two reagent inlets 447 are configured to intersect the cell focusing channel 460 and introduce reagents for subsequent processing and analysis into the fluid containing the barcoded T cells. The mixture of reagents and the cells then enter a flow focusing nozzle 441 through a flow focusing inlet 445 and are extruded through a flow focusing outlet 446. The flow focusing outlet 446 then intersects two carrier inlets 442 configured to encapsulate the cells and reagents in an immiscible carrier fluid (e.g., fluorinated oil) and generate a droplet. The generated droplets flow into droplet outlet 443 to be collected downstream. Droplet size is an important size to control to optimize subsequent processing and analysis. As shown here, the droplet generator is configured to generate droplets between 40 and 60 micrometers in diameter and between 30 and 110 picoliters, more specifically droplets about 55 micrometers diameter and 80 picoliters in volume. To generate such droplets, the flow focusing inlet 445 tapers in diameter to the final diameter of 60 micrometers for the flow focusing outlet 446. In addition, the length 448 of the flow focusing nozzle is 30 micrometers.

Figure 4E:
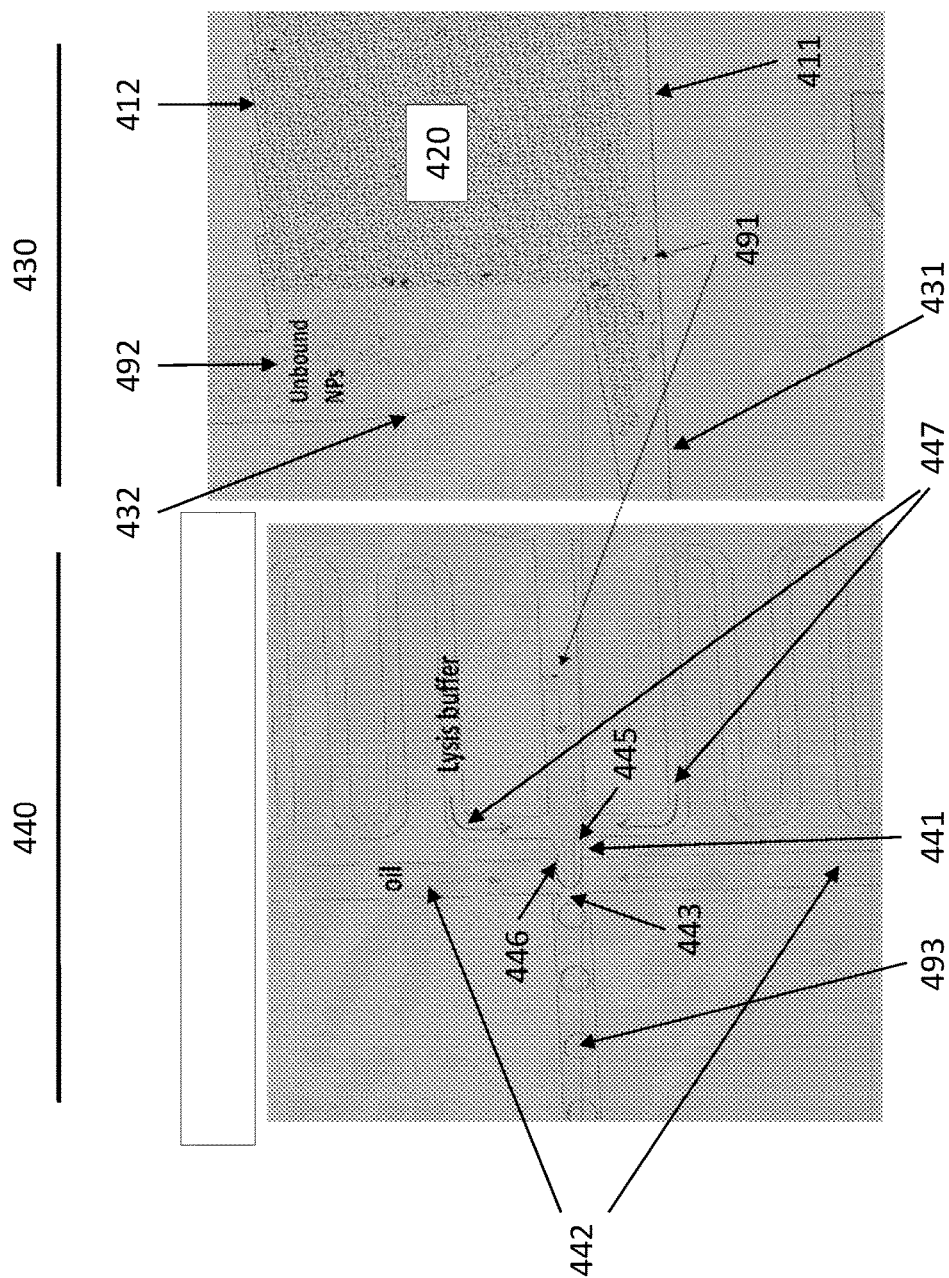
FIG. 4E shows a cross-sectional views of an embodiment of the microfluidic device in operation for the separation of barcoded T cells from unattached nanoparticles.

FIG. 4E shows a cross-sectional views of an embodiment of the microfluidic device in operation for the separation of barcoded T cells 491 from unattached nanoparticles 492. The right panel shows a cross-sectional view of a design of the bifurcation point 430 demonstrating the DLD array 420 directing barcoded T cells 491 to the bottom wall 411 and the cells entering the collection channel 431. The right panel also demonstrates unbound nanoparticles 492 flowing along the upper wall 412 and into the waste channel 432. The left panel shows a cross-sectional view of a design of the droplet generator 440 delivering the barcoded T cell in a single cell stream, where the stream intersects with reagent inlets 447 configured to introduce reagents for subsequent processing and analysis (e.g., the "lysis buffer"). Also shown in the left panel, the mixture of reagents and particle containing fluid enters into the flow focusing inlet 455 and extruded out of the flow focusing outlet 446 and encapsulated by the immiscible carrier fluid (e.g., the "oil") delivered by the carrier inlets 442. Generated droplets 493 then enter the droplet outlet 443 and are collected downstream. Examples of single-cell droplets (494) are demonstrated in FIG. 4F, which also demonstrates that the majority of droplets (493) do not contain a cell.

The engineered microfluidic chips described herein enable the barcoded T-cells to be separated and isolated at the single cell level with high efficiency in a continuous manner.

Although the microfluidic device has been described with respect to separation of bound and unbound particles for T cell analysis, the device can be used broadly for application to separation of particles in a sample by size and isolating particles for further analysis. Thus, provided herein, according to some embodiments are microfluidic devices designed to separate objects on the basis of physical size and to isolate separated objects for subsequent analysis. The objects can be cells, biomolecules, inorganic beads, or other objects of round or other shape. Typical sizes fractionated can range from 100 nanometers to 50 micrometers; smaller or larger sizes can be fractionated. Use of these arrays can involve continuous flows in one direction, and particles can be separated from the flow direction by an angle which is a monotonic function of their size.

The methods, compositions, devices, and/or systems described herein can be used for high-throughput processing (e.g., chemical and/or enzymatic treatment), purification, isolation, and/or concentration of particles. The methods, compositions, devices, and/or systems described herein can be used to isolate particles with relatively high purity, yield, and/or viability if the particles are living, (e.g., cells or organisms). One or more samples can be applied to one or more inlets on a device. One or more buffers can be applied to one or more inlets on a device. Particles of at least a critical (predetermined) size can be passed through an array of obstacles and be deflected to one outlet, and particles less than the critical size can pass to a region for isolation and subsequent analysis.

Fluorescence Activated Cell Sorting

Barcoded NP-antigen-MHC complexes bound to T cells are able to be isolated as single cells using methods other than the DLD device described above. Barcoded T cells can be sorted using fluorescence-activated cell sorting (FACS). In some embodiments, the barcoded NP-antigen-MHC complexes bound to a T cell is made fluorescent using a variety of methods. In specific embodiments, one or more of the attachment moieties are fluorescent. In one example, the streptavidin core is attached to or binds to a fluorescent molecule. In other embodiments, the T cell is stained using antibodies conjugated to a fluorescent molecule. In certain embodiments, the T cell is stained using a panel of antibodies conjugated to different fluorescent molecules. In still other embodiments, the nanoparticle can be fluorescent or conjugated to a fluorophore directly. In some embodiments, multiple elements within the complex (e.g., the attachment moiety, the stained T cell, and the nanoparticle) can be fluorescent, including each comprising a different fluorophore. The nanoparticles used can also be magnetic or non-magnetic. If magnetic, the nanoparticles separated using the magnetic methods in conjunction with FACS, (e.g., before, after, or before and after FACS). The method also The barcoded T cells can be separated by FACS into a bulk collection container (e.g., every barcoded T cell isolated is collected in the same container). Individual barcoded T cells can be also separated by FACS into individual collection containers, such as a multi-well plate. The individual collection container can be single-cell reaction vessels. For example, components used for downstream processing and analysis can be added to each single-cell reaction vessel, as described in greater detail below.

T Cell Receptor Amplification and Analysis

After isolation of barcoded T cells into single-cell droplets, the nucleic acid of the barcoded T cell can be further processed for downstream analysis. Specifically, the expressed TCRα and TCRβ mRNA transcripts can be first converted to cDNA by reverse transcription and the cDNA is amplified for next generation sequencing. As part of this process, the cDNA is barcoded allowing downstream pairing of the TCRα and TCRβ mRNA transcripts with the specific antigen recognized by the T cell. The general protocol to generate the barcoded TCRα and TCRβ cDNA is illustrated in FIG. 3.

As described above, multiple copies of two defined single-stranded polynucleotide sequences are attached to the NP-antigen-MHC complex. Each defined barcoded polynucleotide comprises in a 5' to 3' orientation (1) a universal PCR primer target sequence (UP1), (2) a defined barcode sequence (NI), and (3) either a TCRα or a TCRβ primer sequence (FIG. 1B). The defined barcode sequence (NI) is unique for the antigen in the NP-antigen-MHC complex but is shared between the first and the second single-stranded polynucleotide sequence.

In embodiments, following isolation of the single antigen specific T cell bound to one or more barcoded NP-antigen-MHC complex, the transcripts for the expressed TCRα and TCRβ chains are converted to cDNA. To do so, the nucleic acid from the T cell can be released. In some embodiments, the T cell is lysed to release the nucleic acid. Examples of lysis agents include, but are not limited to lysis enzymes (e.g. lysozyme) and surfactants or detergents. In certain embodiments, the surfactant is a non-ionic surfactant including, but not limited to, IGEPAL CA 630, TritonX-100, and Tween 20. In other embodiments, the surfactant is an ionic surfactants including, but not limited to, sarcosyl and sodium dodecyl sulfate (SDS). In certain embodiments, the surfactant is at a final concentration that disrupts cellular membrane but does not disrupt the immiscible fluid (e.g., the oil) encapsulating the droplet. In specific embodiments, the lysis reagent is IGEPAL CA 630 at a final concentration of 0.25%. In other embodiments, non-reagent based lysis systems can be used to release nucleic acid from the cell including, but not limited to, heat, electroporation, mechanical disruption, and acoustic disruption (e.g., sonication).

Figure 2:
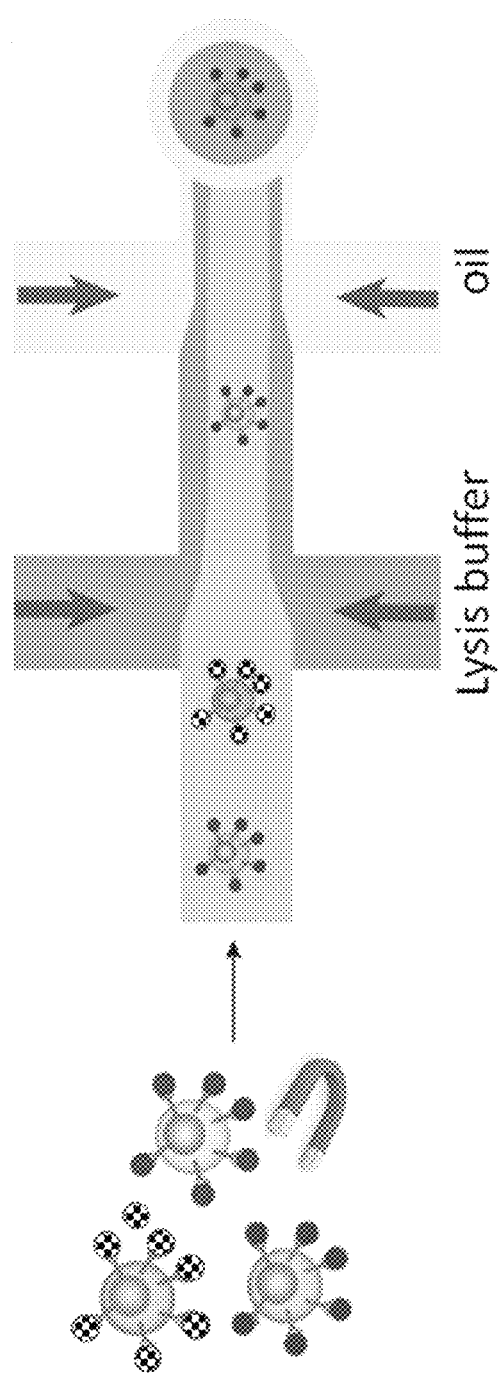
FIG. 2 illustrates a general overview of single-cell droplet formation containing additional reagents.

In some embodiments, lysis is carried out directly in a droplet. In some embodiments, a lysing reagent is added immediately prior to droplet formation such that lysis only occurs in the droplet. In certain embodiments, as exemplified in the microfluidic device described above, the lysing reagent is introduced into the cell containing fluid immediately upstream of droplet formation (see FIGS. 2 and 4E) with other reagents (e.g., RT, releasing, and PCR amplification reagents described elsewhere).

In some embodiments, the single-cell droplet is disrupted (e.g., emulsified) in a single-cell reaction vessel prior to the addition of lysis reagents.

Following release of the nucleic acid (e.g., the TCRα and TCRβ mRNA transcripts) from the cell into the droplet or single-cell reaction vessel, mRNA is reverse transcribed into cDNA. To do so, reverse transcriptase (RT) is added to the single-cell droplet or single-cell reaction vessel. In certain embodiments, as exemplified in the microfluidic device described above, the RT is introduced into the cell containing fluid immediately upstream of droplet formation (see FIGS. 2 and 4E). In other embodiments, RT is added directly to a single-cell reaction vessel. In some embodiments, RT is added to the single-cell reaction vessel following droplet disruption. In specific embodiments, the RT is added simultaneously with other reagents (e.g., the lysing, releasing, and PCR amplification reagents described elsewhere). In addition to the RT, additional components are added to carry out the first strand synthesis of cDNA. Examples of additional components are well known to those skilled in the art and include, but are not limited to, dNTPs, RNase inhibitors, buffering agents (e.g., Tris-HCL), chelators (e.g., EDTA), and DTT. In specific examples, the additional components, such as DTT, are added to increase efficiency of the RT reaction. In preferred embodiments, the final DTT concentration is 5 mM.

To generate cDNA from mRNA, a single-stranded DNA polynucleotide anneals to the mRNA and reverse transcriptase transcribes the first strand cDNA using the mRNA as a template. In embodiments of the present invention, the two defined single-stranded polynucleotide sequences attached to the NP-antigen-MHC complex act as the initial primers that anneal to the mRNA. In specific embodiments, the TCRα and TCRβ primer sequences regions of the single-stranded DNA polynucleotides act as the initial primers by annealing to regions of the TCRα and TCRβ constant region sequences of the mRNA transcripts. During this step, since the defined sequence unique for the antigenic peptide (e.g., the barcode or NI) is attached to the TCRα and TCRβ primer sequences, the cDNA becomes barcoded during the RT reaction. In embodiments of the present invention, since the mRNA is from a single antigen specific T cell, the barcoded TCRα and TCRβ cDNAs generated can be paired and associated with a specific antigen during subsequent sequence analysis.

In some embodiments, efficiency of the RT reaction step is improved by first releasing the two defined single-stranded polynucleotide sequences attached to the NP-antigen-MHC complex. In certain embodiments, the single-stranded polynucleotide sequences comprise a cleavable linker 5' of the universal PCR primer target sequence UP1. In specific embodiments, the cleavable linker is a photo-cleavable linker. In preferred embodiments, the photo-cleavable linker is a UV cleavable linker. An example of a UV cleavable linker useful for the present invention is a biotin modification with a photocleavable group having the formula shown below ("5PCBio", synthesized by IDT):

simultaneously with the (e.g., the lysing, RT, and PCR amplification reagents described elsewhere). In other embodiments, the single-cell reaction vessel is exposed to a releasing stimulus. In some embodiments, the single-cell reaction vessel is exposed to a releasing stimulus following droplet disruption.

Before performing next generation sequencing, the cDNA is additionally amplified by PCR. In embodiments of the present invention, a first round of PCR amplification is performed in the droplet following generation of the cDNA in the RT reaction. In some embodiments, reagents for PCR amplification are introduced into the single-cell droplet. In certain embodiments, as exemplified in the microfluidic device described above, the PCR amplification reagents are introduced into the cell containing fluid immediately upstream of droplet formation (see FIGS. 2 and 4E). In other embodiments, PCR amplification is performed in a single-cell reaction vessel. In certain embodiments, PCR amplification is performed following droplet disruption. In specific embodiments, PCR amplification reagents are added directly to a single-cell reaction vessel. In some embodiments, PCR amplification reagents are added to the single-cell reaction vessel following droplet disruption. In specific embodiments, the PCR amplification reagents are added simultaneously with other reagents (e.g., the lysing, RT, and releasing reagents described elsewhere). PCR amplification

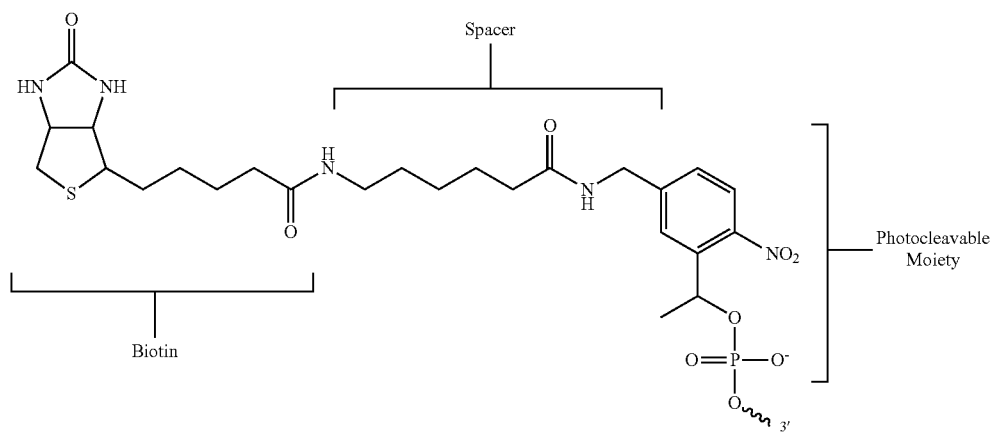

<www (dot) idtdna (dot) com/pages/education/decoded/article/which-biotin-modification-to-use-> (retrieved Mar. 1, 2018)

Other examples of cleavable linkers include linkages that can be cleaved by enzymatic or chemical means. Examples of chemical means include, but are not limited to, use of reducing agents, an example of which is described in further detail in US Publication No. 2015/0376609, herein incorporated in its entirety.

In embodiments of the present inventions, release of the polynucleotide sequences can be carried out by exposing the single-cell droplets or single-cell reaction vessels to a releasing stimulus. In a specific embodiment, the single-cells droplets or single-cell reaction vessels are exposed to a light stimulus. In a preferred embodiment, the single-cell droplets or single-cell reaction vessels are exposed to UV light. In specific embodiments, the single-cell droplets are exposed to UV light in the collection container or the tubing described in the above microfluidic devices. In other embodiments, a releasing stimulus is introduced into the single-cell droplet. In certain embodiments, the releasing stimulus is introduced reagents are well known to those skilled in the art and include, but are not limited to, DNA polymerase, dNTPs, buffering agents (e.g., Tris-HCL), and chelators (e.g., EDTA). In a specific embodiment, the DNA polymerase is KOD hot DNA polymerase (EMD) In addition, primers are introduced to amplify the cDNA. In embodiments of the current invention, the two defined single-stranded polynucleotide sequences described above are also used as reverse primers during the first DNA amplification round. In some embodiments, forward primers comprise a TCRα and a TCRβ forward primer. In certain embodiments, each forward primer comprises a second universal PCR primer target sequence ("UP3") and a sequence designed to hybridize to a TCRα and a TCRβ variable region, respectively. In specific embodiments, the sequences designed to hybridize to a TCRα and a TCRβ variable region are a set of multiplexed primers designed to anneal to known TCRα and a TCRβ variable region sequences. In a preferred embodiment, the set of multiplexed primers are designed to selectively amplify at least a TCR complementarity determining region (CDR) 3 sequence.

In embodiments of the present invention, following the first round of amplification, the amplified cDNA is further amplified. In some embodiments, the cDNA is extracted from the droplet prior to amplification. In certain embodiments, the droplet is de-emulsified using a de-emulsifying reagent to extract the cDNA. Examples of de-emulsifying reagents include, but are not limited to, fluorocarbon alcohols, such as perfluorooctanol. In some embodiments, additional amplification primers, as well as any reagents necessary for further PCR amplification, are added to the extracted DNA. In other embodiments, additional amplification primers, as well as any reagents necessary for further PCR amplification, are added directly to a single-cell reaction vessel. In some embodiments, PCR amplification reagents are added to the single-cell reaction vessel following droplet disruption. In specific embodiments, the primers anneal to the first and second universal PCR primer target sequences (e.g., UP1 and UP3). The use of amplification primers that anneal to universal PCR primer target sequences allows for the pooling of cDNA from all the droplets and using a common set of reagents. The cDNAs do not require being separated In some embodiments, another DNA amplification round is performed and another set of primers is provided. In certain embodiments, the primers include (1) a forward sequencing primer comprising a third universal PCR primer target sequence ("UP2") and a sequence capable of hybridizing to at least a portion of the first universal PCR primer target sequence, and (2) a reverse sequencing primer comprising a fourth universal PCR primer target sequence ("UP4") and a sequence capable of hybridizing to at least a portion of the second universal PCR primer target sequence. In specific embodiments, the third and fourth universal PCR primer target sequences are sequencing adaptors for use in next generation sequencing. In preferred embodiments, the sequencing adaptors are Illumina adaptors.

In some embodiments, in addition to the UP1, NI, and Cα or Cβ sequences, each copy of the two defined single-stranded polynucleotide sequences further comprises a unique molecular identifier ("UMI"). A UMI, as used herein, is a random nucleotide sequence that is, in principle, unique for every individual polypeptide. UMIs are useful in downstream sequencing analysis, specifically single-cell sequencing analysis, to remove sequencing errors due to amplification bias of certain sequences and is well known to those skilled in the art, for example, as described in further detail in Islam et al. (Nature Methods volume11, pages 163-166; 2014), herein incorporated by reference in its entirety.

Following amplification of the barcoded TCRα and a TCRβ cDNAs, including attachment of sequencing adaptors, the cDNAs are sequenced using next generation sequencing (NGS) methods known to those skilled in the art, including, but not limited to, sequencing by synthesis technologies (Illumina). Once sequenced, the resulting sequencing reads can be analyzed and the defined barcode sequence (i.e., the barcode or NI) used to pair antigen specific TCRα and a TCRβ chains.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* 3rd Ed. (Plenum Press) Vols A and B (1992).

Example 1: Barcoded NP-Antigen-MHC Complexes

Barcoded NP-antigen-MHC complexes were used to successfully identify correctly paired TCRα/β genes from a single antigen specific T cell. The design of the barcoded NP-antigen-MHC complexes allowed for capturing an antigen specific T cell, sequencing both a TCRα and a TCRβ gene, and assigning the sequenced genes to the specific antigen recognized by the T cell. Referring to FIG. 1B, the barcoded NP-antigen-MHC complexes were composed of magnetic nanoparticles ("NP"), each with three components attached to its surface. The first component was a major histocompatibility complex (MHC)-antigen complex assembled as a multimer using a streptavidin scaffold and displaying an antigenic peptide. The second and third components on the surface were both single stranded DNA oligomers ("barcoded polynucleotides"). Each of those oligomers had 3 segments. The first ("UP1") is a universal target sequence, the second ("NI") is a defined barcode sequence that is operably associated with the identity of the antigenic peptide, and the third (Cα or Cβ) is a sequence designed to hybridize to a portion of a constant region of a TCRα or TCRβ mRNA expressed in a T cell.

Example 2: MHC-Antigen Complex Production

MHC bound peptide complexes (pMHC) were generated using a UV-mediated peptide exchange method (FIG. 1A). Photo-labile peptide KILGFVFJV (SEQ ID NO: 1) and other antigenic peptides were synthesized with standard automated Fmoc-peptide synthesis methodology (J, (S)-3-(Fmoc-amino)-3-(2-nitrophenyl) propionic acid, is the photo-labile amino acid residue). Plasmids encoding human MHC class I heavy chain and human β2m containing bacterial strain were from Ton N M Schumacher. MHC photo-labile protein was folded from MHC heavy chain inclusion body, β2m inclusion body and a photo-labile peptide according to the published protocol and then biotinylated using the BirA biotin ligase. A mixture of MHC photo-labile protein (0.5 µM) and a single antigenic peptide sequence (50 µM) was exposed to 365 nm UV light for 1 hour to generate pMHC complexes. Examples of general methods for UV-mediated peptide exchange are described in greater detail in Toebes et al., 2006, *Nat. Med.* 12:246-251 and Bakker et al., *PNAS*, 2008, 105:3825-3830, herein incorporated by reference in their entirety.

The biotinylated pMHC complexes were then bound to a modified streptavidin core (FIG. 1A). To produce the DNA bound streptavidin core (the "DNA-SAC"), cysteine-modified streptavidin conjugated to a polynucleotide hybridization domain complementary to the polynucleotide hybridization domain contained on the nanoparticle was produced following a previously published protocol as described in Kwong et al., 2009, *J. Am. Chem Soc.*, 131:9695-9703, the entire contents of which are herein incorporated by reference. Briefly, SAC was first expressed from the pTSA-C plasmid containing the SAC gene (Addgene), as described in Sano et al., 1990, *PNAS*, 87:142-146, the entire contents of which is herein incorporated by reference. Before conjugation to the polynucleotide hybridization domain, SAC (1 mg/ml) was buffer exchanged to PBS containing Tris(2-Carboxyethyl) phosphine Hydrochloride (TCEP, 5 mM) using zeba desalting columns (Pierce). Then MHPH (3-N-Maleimido-6-hydraziniumpyridine hydrochloride, 100 mM, Solulink) in DMF was added to SAC at a molar excess of 300:1. In addition, SFB (succinimidyl 4-formylbenzoate, 100 mM, Solulink) in DMF was added to 5'-amine modified ssDNA (500 µM) (5'-NH$_2$-AAA AAA AAA A TAG GCA TCC CGA GGA TTC AG [SEQ ID NO: 2]) in a 40:1 molar ratio. After reacting at room temperature (rt) for 4 hours, MHPH-labeled SAC and SFB-labeled DNA were buffer exchanged to citrate buffer (50 mM sodium citrate, 150 mM NaCl, pH 6.0), and then mixed in a 20:1 ratio of DNA to SAC to react at room temperature overnight. DNA-SAC conjugate was purified using the Superdex 200 gel filtration column (GE health) and concentrated with 10K MWCO ultra-centrifuge filters (Millipore). The DNA-SAC was then incubated with the biotinylated pMHC produced above to generate the antigen-MHC complexes to be hybridized to nanoparticles (FIG. 1A).

Example 3: Magnetic Nanoparticle Labeling

In an illustrative example, a barcoded NP-antigen-MHC complex was generated using a magnetic nanoparticle. DNA polynucleotides UP1-NI-Cα, UP1-NI-Cβ and the polynucleotide hybridization domains (Table 1) were synthesized (Integrated DNA technologies, Inc. "IDT"). UP1-NI-Cα and UP1-NI-Cβ were also modified at the 5' end with a biotin and a photocleavable group with the formula shown below ("5PCBio", synthesized by IDT):

<www (dot) idtdna (dot) com/pages/education/decoded/article/which-biotin-modification-to-use-> (retrieved Mar. 1, 2018)

In addition to the UP1, NI, and Cα or Cβ sequences, the synthesized UP1-NI-Cα and UP1-NI-Cβ polynucleotides also possessed an 8 nucleotide random sequence between the UP1 and NI (i.e., the 8 consecutive Ns, Table 1). This 8-mer randomer is a unique molecular identifier ("UMI") that is in principal unique for every polypeptide synthesized and typically used during subsequent sequencing analysis to remove sequencing errors due to amplification bias of certain sequences, described in further detail in Islam et al. (Nature Methods volume 11, pages 163-166; 2014), herein incorporated by reference in its entirety.

Figure 7:
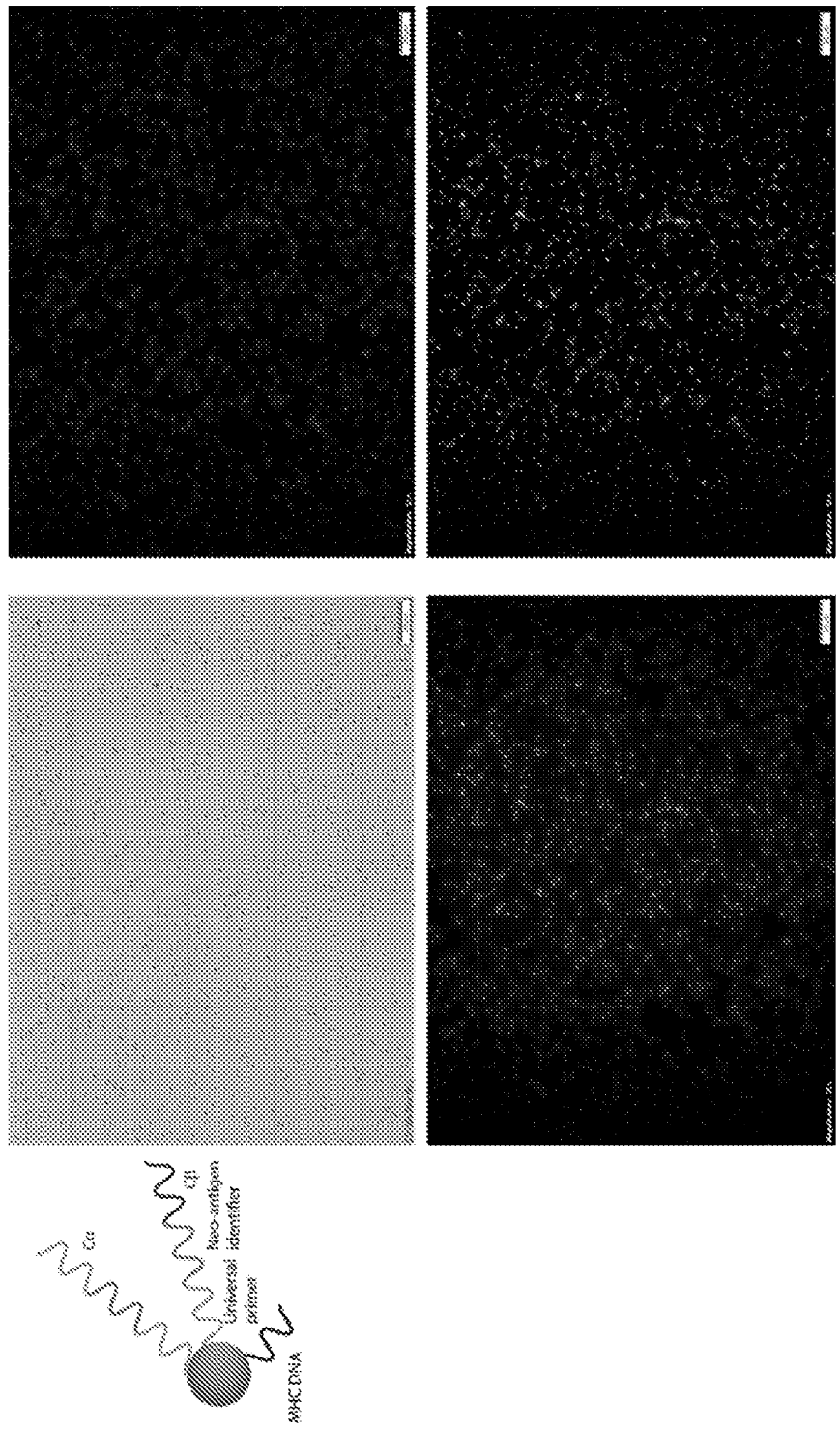
FIG. 7 The nanoparticle is labeled with three different DNA (UP1-NI-Cα, UP1-NI-Cβ and MHC linker DNA) at the same time. Magnetic nanoparticles are shown (top left panel). Complementary DNA for Cα (top right panel), Cβ (bottom left panel) and MHC-DNA (bottom right panel) are hybridized to the DNA on the nanoparticle and give the correct fluorescence, indicating the successful DNA labeling on the nanoparticles.

Streptavidin coated magnetic nanoparticles (1 µM, Dynabeads™ MyOne™ Streptavidin T1, ThermoFisher catalog #: 65601) were incubated with a mixture of the synthesized polynucleotides at a ratio of 1 streptavidin/8 DNA. UP1-NI-Cα, UP1-NI-Cβ and the polynucleotide hybridization domains in were added at an equal ratio to the mixture. Attachment of UP1-NI-Cα, UP1-NI-Cβ and the polynucleotide hybridization domains to the nanoparticles was confirmed by incubating the nanoparticles with complementary DNA labeled with fluorescent dyes. As shown in FIG. 7, fluorescence was detected on the magnetic nanoparticles (top left panel) for UP1-NI-Cα (top right panel), UP1-NI-Cβ (bottom left panel), and the polynucleotide hybridization domain (bottom right panel) demonstrating proper attachment of each element to the magnetic nanoparticles.

After attachment of the polynucleotides, the barcoded nanoparticles were then hybridized to a given pMHC-DNA-SAC complex to generate barcoded NP-antigen-MHC complexes (FIG. 1B). For each nanoparticle, approximately $3\times10^3$ copies of UP1-NI-Cα, UP1-NI-Cβ, and the pMHC-DNA-SAC complexes were attached. In examples using a library, barcoded nanoparticles displaying different antigenic peptides were mixed together. By designing different DNA sequences in the neo-identifier (NI) region, a unique NI was generated to barcode each distinct pMHC in the library. In a typical library, 50 different barcoded NP-antigen-MHC complexes are used, but can be scaled up or down as needed. Approximately $1\times10^6$ nanoparticles of each barcoded NP-antigen-MHC complex was incubated with a sample, but can also be scaled up or down as needed.

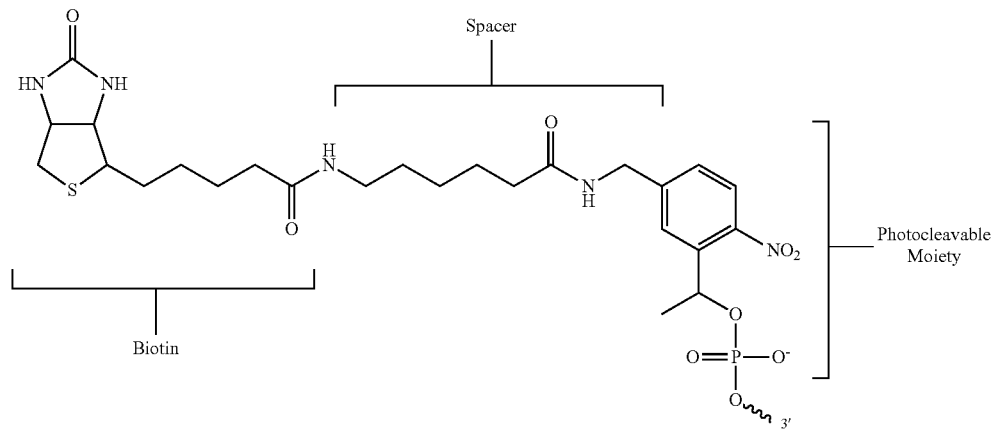

TABLE 1

Representative DNA sequence used for the nanoparticle labeling.

| Name | DNA sequence |
|---|---|
| UP1 | TCGTCGGCAGCGTCAGATGTGTATAAGAGACAG (SEQ ID No: 3) |
| Cα | TCTCTCAGCTGGTACACGGC (SEQ ID No: 4) |
| Cβ | GATGGCTCAAACACAGCGACCTC (SEQ ID No: 5) |
| UP1-NI-Cα | /5PCBio/TCGTCGGCAGCGTCAGATGTGTATAAGAGACAGNNNNNNNNN _CGAGTC_TCTCTCAGCTGGTACACGGC (SEQ ID No: 6) NI barcodes denoted as bold italic, Ns refer to random nucleotide UMI barcodes |
| UP1-NI-Cβ | /5PCBio/TCGTCGGCAGCGTCAGATGTGTATAAGAGACAGNNNNNNNNN _CGAGTC_GATGGCTCAAACACAGCGACCTC (SEQ ID No: 7) NI barcodes denoted as bold italic, Ns refer to random nucleotide UMI barcodes |
| Polynucleotide Hybdrization Domain | /5BiosG/AAAAAAAAACTATGTCGATACAAGTCAGATAGTTCAACT CGTTCACTATAA_CTGAATCCTCGGGATGCCTA_ (SEQ ID No: 43) DNA sequence that hybridizes with DNA-SAC polynucleotide hybdrization domain denoted as bold italic |
| Complementary Polynucleotide Hybdrization Domain | TAGGCATCCCGAGGATTCAG (SEQ ID No: 9) |

Example 4: Magnetic Isolation of Cells

Barcoded NP-antigen-MHC complexes displaying the NY-ESO specific antigenic peptide SLLMWITQV (SEQ ID NO: 10) were incubated with NY-ESO Jurkat cells (stained green) for 15 min at room temperature. The nanoparticles, including nanoparticles bound to the NY-ESO Jurkat T cells, were isolated using a magnet (DynaMag™-2 Magnet, Thermo, 12321D), away from unbound cells and then imaged by microscope. The results indicated that all the fluorescent cells (right panel) correlated with dark brightfield images (left panel) demonstrating the cells were coated with nanoparticles, demonstrating that barcoded NP-antigen-MHC complexes can be used to efficiently enrich target cells (FIG. 8).

Example 5: DLD Microfluidic Device Design

The microchip (e.g. the DLD microfluidic device) used a seamless integration of two distinct functions: 1) separation of NP-labeled CTLs from unbound NPs, and 2) capture of single labeled CTLs in individual droplets with lysis buffer and RT-PCR reagents. To carry out these functions, the device used 4 inlets (buffer [402], NP/cell [401], oil [403], and lysis/RT-PCR reagents [404]) and 2 outlets (NP waste and collection outlet [499]), as shown in FIG. 4a.

The DLD device was designed with the following parameters.

DLD array design: A DLD array separates unbound NPs (1-μm diameter) and labeled cells (~8-μm diameter) based on size differential. The flowing cells collide with a pillar array [420], deflecting their trajectory toward the droplet generator, while the unbound NPs continue to flow toward the waste reservoir without disruption. FIG. 4A is a cross-sectional view of a design of a microfluidic device (400) for the separation of barcoded T cells from unattached nanoparticles. As shown, the microfluidic device comprises a sample inlet port (401) and a buffer inlet port (402), an immiscible fluid inlet port (403), a reagent inlet port (404), a collection outlet (499) to collect droplets, and a waste outlet (498) from the chip. The microfluidic device comprises a separation channel (410) that includes DLD arrays (420, i.e., arrays of obstacles) for the separation of large barcoded cells from unbound nanoparticles. Following the DLD array, the separation channel bifurcates into two paths (430): the top waste channel (432) is for unattached nanoparticles and the bottom collection channel (431) is for barcoded T-cells. The barcoded T-cells are sorted to the bottom wall (411) by the DLD array, then enter a cell-focusing channel (460) with a serpentine structure, where the barcoded T-cells are slowed and orderly arranged into a single-cell stream. The unattached nanoparticles are carried across the top path along the top wall (412) and carried to the waste outlet (498). From the cell-focusing channel, barcoded T cells flow into the droplet generator and isolated into single-cell droplets. The single cell droplets then pass though tubing (470) and exit the microfluidic device at the collection outlet (499) and into a collection container.

As shown in FIGS. 4A and 4B, the efficiency of separation using this device (400) was optimized by tuning design parameters of the DLD array (420), including pillar shape (422), gap (424), row offset tilt angle (426), width of the pillar array, and length of the pillar array (410). The parameters of the array and the obstacle topology (422) have been optimized to separate T-cells, which are bigger than 4 μm, from unbound nanoparticles smaller than 4 μm (i.e., the critical size is 4 μm). The optimized design used an "I-shape" pillar design with 12.5 μm gap, 45 μm pitch, 4.5 μm row shift (i.e. θ=5.71° tilt angle), and was 14 mm in length, 4 mm longer than the circular pillar design. The array design is not limited to that illustrated in FIG. 4. Other tested configurations included use of circular pillars with 11 μm gap, 30 μm pitch, and 3 μm row shift (i.e. θ=5.71°). Such configurations were also used successfully (data not shown).

Droplet generator design; The barcoded T cells, once arranged into a single-cell stream by the cell focusing channel (460), enter into the droplet generating device (440). FIG. 4D left panel is an enlarged cross-sectional view of the droplet generator, and the right panel is a further enlargement of the channel intersections within the droplet generator. Two reagent inlets (447) are configured to intersect the cell focusing channel (460) and introduce reagents for subsequent processing and analysis into the fluid containing the barcoded T cells. The mixture of reagents and the cells then enter a flow focusing nozzle (441) through a flow focusing inlet (445) and are extruded through a flow focusing outlet (446). The flow focusing outlet (446) then intersects two carrier inlets (442) configured to encapsulate the cells and reagents in an immiscible carrier fluid (e.g., fluorinated oil) and generate a droplet. The generated droplets flow into droplet outlet 443 to be collected downstream.

Since RT-PCR is performed in a droplet, an important consideration is optimizing thermal stability of the droplet. Although fluorosurfactants, such as 5% w/w PEG-PFPE amphiphilic block copolymer, can be used to stabilize droplet interface, a droplet can still burst during thermal cycling if it is too large. However, if the droplet is too small, there can be insufficient reagents to complete an RT-PCR reaction for a single cell. Thus, an important parameter to control in the microchip is droplet size.

We determined empirically in this example that the maximum droplet size that does not rupture after 40 cycles of thermal cycling was about 55 micrometers diameter and 80 picoliters in volume. To generate such droplets, the flow focusing inlet (445) tapers in diameter to the final diameter of 60 micrometers for the flow focusing outlet (446). In addition, the length (448) of the flow focusing nozzle is 30 micrometers.

In addition, the number and location of the syringe pumps attached to microfluidic to control fluid rate was optimized to improve operation efficiency and to reduce cost. Conventional droplet generation microchips inject fluids in each inlet using syringe pumps, adjusting flow rates of the pumps to maintain optimal conditions in the device. For example, the oil inlet is typically pumped three times faster than the aqueous inlets (e.g. cell or RT-PCR reagents). However, this strategy uses at least 4 syringe pumps, which makes the microchip difficult and expensive to operate.

To simplify device operation, the microchannel geometry (width and length) was optimized to reliably and accurately control fluid flow, enabling operation of the device with two syringe pumps connected at the outlet (NP waste and droplet collector). To start the initial droplet generation, oil was loaded, and a syringe vacuum pressure of 0.75 atmosphere was applied at the droplet collector, followed by a constant withdrawal of 5 mL/hr. The vacuum was applied by attaching a 60 ml syringe (BD) to the collection outlet with the plunger adjusted to the 30 ml mark. Once connected, the plunger was moved to the 40 ml mark and held in place by a syringe pump holder, applying about 0.75 atm of negative pressure at the collection outlet (i.e. P_outlet=1 atm*30/40=0.75 atm). Once droplet generation began, bare NPs were used to determine the optimal withdrawal speed at the NP waste outlet attached to a 1 ml syringe (BD), which was typically around 0.2 mL/hr. A PHD 22/2000 syringe pump (Harvard Apparatus) was connected to each syringe and used to control plunger position and flow rate. After the remaining reagents were loaded in the inlets, the NP waste withdrawal speed was further tuned to 1) maintain a lysis/RT-PCR reagent to cell aqueous input ratio of 2:1 (determined visually at the flow focusing junction) and 2) prevent unbound NP from leaking into the droplet generator. The 2:1 ratio established the correct final reagent concentration in the droplet. The reagent concentration (e.g. reverse transcriptase and other RT and PCR application components) in the miscible fluid was set at 1.5×, such that a 2:1 ratio produced a final 1× concentration in the droplet after formation. If device is consistently producing a different ratio than 2:1, the concentration of the miscible fluid can be adjusted so that the final droplet will be at 1×.

Example 6: Single Cell Droplet Generation

Before addition of sample, the DLD-droplet device described above (FIG. 4A) was primed to enable droplet generation (aqueous droplets in oil). Device surfaces were made hydrophobic by treatment with Aquapel. Then, four sets of solutions were sequentially pumped into the device: 1) 70% ethanol (to remove bubbles), 2) 3% F68 pluronic (to passivate surface from cell and biomolecular fouling), 3) PBS (to wash out excess pluronic), and 4) optimized buffer (for single-cell RT-PCR).

Figure 4F:
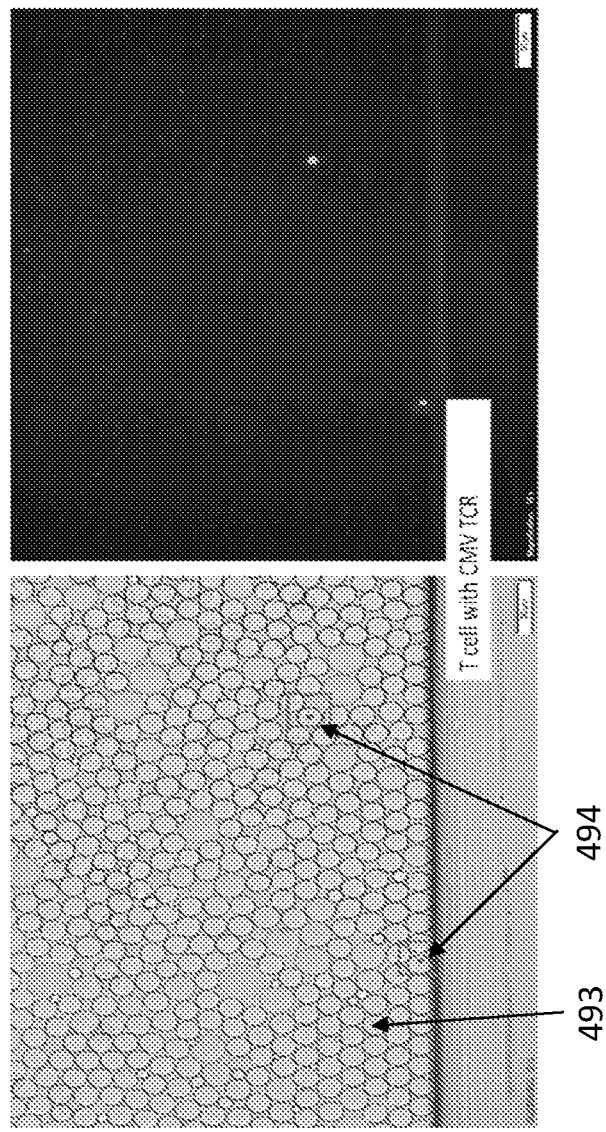
FIG. 4F shows examples of droplets containing isolated single cells collected from the device.

Next, isolated nanoparticles, including both bound and unbound to T cells, were added to a DLD-droplet device. As demonstrated in FIG. 4E (right panel), the unbound nanoparticles (492) were directed to the waste channel (432) by the DLD array (420), while the T cells bound to barcoded NP-antigen-MHC complexes (491) were directed to the collection channel (431). In the droplet generator (440), each individual T cell (491) was mixed with RT-PCR reagents (i.e., "lysis buffer") and then encapsulated by a fluorinated oil (HFE-7500 containing 5% w/w PEG-PFPE amphiphilic block copolymer fluorsurfactant, RAN Biotechnologies #008-FluoroSurfactant-5wtH) to generate the single cell droplet (494, FIG. 4F). Lysis buffer was excluded in the RT-PCR buffer in an illustrative example to allow downstream visualization and confirmation of encapsulated intact single cells (FIG. 4F, left panel bright field, right panel fluorescence. The majority of the droplets had zero cells in them and only a small fraction contained 1 cell (FIG. 4F, left panel). This low dilution was used in the example to ensure that each droplet had, a most, 1 cell, as 2 or more-cells/droplet can interfere with interpretation of sequencing results.

Example 6. RT-PCR in a Single Cell Droplet

Figure 5:
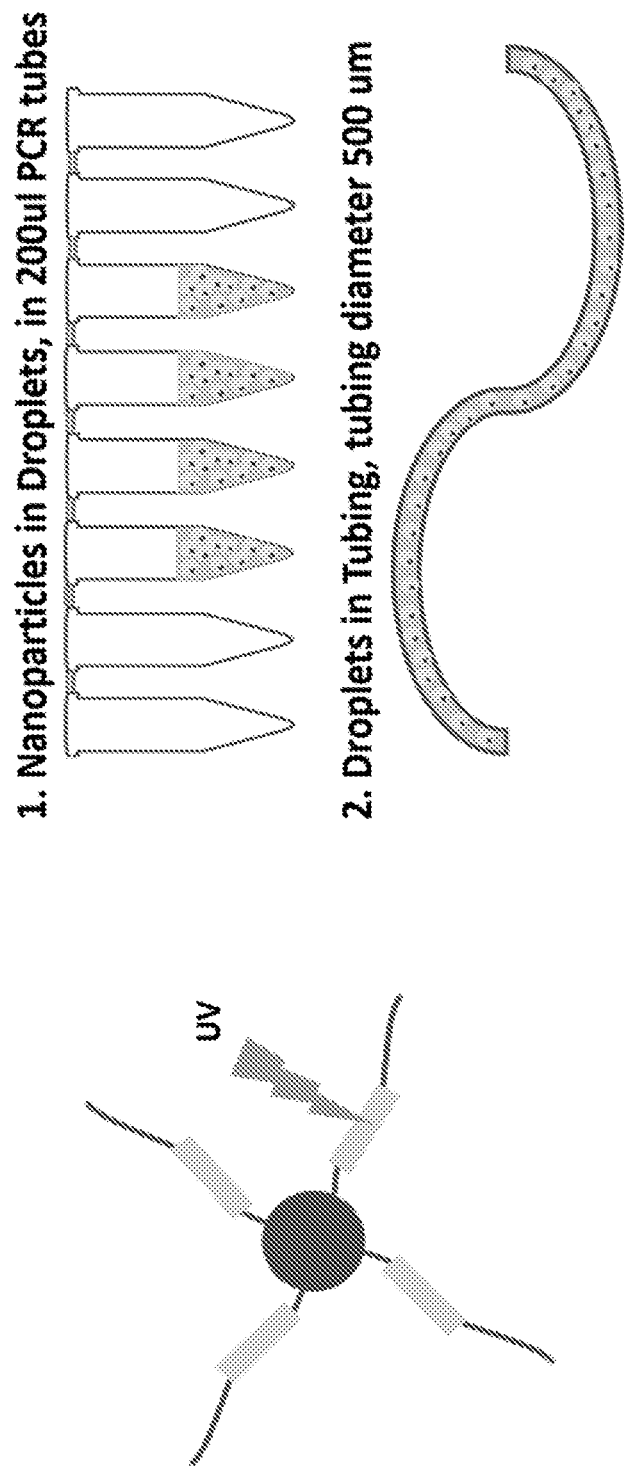
FIG. 5 illustrates different UV cleavage schemes.

Droplets containing an individual T cell bound to barcoded NP-antigen-MHC complexes were then exposed to 365 nm UV light to release the UP1-NI-Cα and UP1-NI-Cβ polynucleotides from the NP-antigen-MHC complex. This was done to improve the efficiency of the reverse transcription (RT) reaction. Previous attempts to perform RT-PCR using UP1-NI-Cα and UP1-NI-Cβ polynucleotides remaining directly to the nanoparticles resulted in poor efficiency of cDNA generation (not shown). To improve efficiency, UP1-NI-Cα and UP1-NI-Cβ polynucleotides were released from the NP-antigen-MHC complex prior to reverse transcription and DNA amplification.). UV mediated release of UP1-NI-Cα and UP1-NI-Cβ polynucleotides was performed using two different methods: 1) UV exposure of bulk droplets in 200 ul PCR tubes, and 2) UV exposure of droplets dispersed in about 500 μm diameter UV permissible tubing (Tygon) (FIG. 5). In the second example, the droplets dispersed within the tubing were exposed to UV light from a separate light source (not shown). Following UV exposure, droplets were collected in the collection containers described above. Release of UP1-NI-Cα and UP1-NI-Cβ in droplets dispersed in tubing was 6 times greater than droplets in 200 ul PCR tubes as quantified by measuring the amount of free DNA released in solution (Table 2).

FIG. 3 illustrates the general workflow used to generate the final desired PCR products UP2-UP1-NI—Cα-Vα-UP3-UP4 and UP2-UP1-NI—Cβ-Vβ-UP3-UP4, which represent the TCRα and TCRβ genes expressed in the single T cell contained in the droplet, respectively. After UV cleavage, the droplets were subjected to RT-PCR to generate the DNA product of UP1-NI—Cα-Vα-UP3 and UP1-NI—Cβ-Vβ-UP3. The "lysis buffer" containing the RT-PCR reagents added during the droplet generation step described above include, 0.25% IGEPAL CA 630 to lyse to the cells, RT-PCR reagents (Qiagen OneStep, #210212) as the source for the reverse transcriptase and PCR polymerase, DTT at a final concentration of 5 mM to improve RT-PCR efficiency. Vα-UP3 (Table 3) and Vβ-UP3 (Table 4) primers were also added for the DNA amplification step following the RT-PCR reaction. UP1-NI-Cα and UP1-NI-Cβ, previously released from the nanoparticles, were also used as reverse primers during the first DNA amplification round. In addition, due to the slow extension speed of the polymerase provided in the Qiagen kit, KOD hot DNA polymerase (EMD/Millipore, #71086) was added at a final concentration of 0.02 U/μl to the lysis/RT-PCR buffer to increase extension speed and decrease the total time and cycles required for DNA amplification. Minimizing the total amplification time and number of amplification rounds can be an important consideration in maintaining the integrity of the droplet to minimize cross contamination. RT-PCR reaction conditions used were: 50° C. for 1 hour, followed by 95° C. for 5 min. Next 40 cycles of DNA amplification were performed (94° C. for 10 s, 68° C. for 20 s, 72° C. for 20 s), followed by a final extension at 72° C. for 10 min and then held at 12° C.).

TABLE 2

| UV cleavage efficiency | |
| --- | --- |
| Condition | DNA cleavage efficiency |
| Nanoparticle in droplets | 14% |
| Droplets in tubing | 87% |

TABLE 3

Single cell TCRa cloning primers
Vα-gene-specific primers for cloning TCRα genes

| TRAV gene | UP3 | Vα |
| --- | --- | --- |
| TRAV1-1*01 | 5'-TACAGGAAGCCTCAGCA (SEQ ID NO 44) | GGACAAAGCCTTGAGCAGCCCTC-3' (SEQ ID NO 46) |
| TRAV 1-2*01 | 5'-TACAGGAAGCCTCAGCA (SEQ ID NO 44) | GGACAAAACATTGACCAGCCCACTG-3' (SEQ ID NO 47) |
| TRAV2*01 | 5'-TACAGGAAGCCTCAGCA (SEQ ID NO 44) | AAGGACCAAGTGTTTCAGCCTTCCAC-3' (SEQ ID NO 48) |
| TRAV3*01 | 5'-TACAGGAAGCCTCAGCA (SEQ ID NO 44) | GCTCAGTCAGTGGCTCAGCCGGA-3' (SEQ ID NO 49) |
| TRAV4*01 | 5'-TACAGGAAGCCTCAGCA (SEQ ID NO 44) | CTTGCTAAGACCACCCAGCCCATC-3' (SEQ ID NO 50) |
| TRAV5*01 | 5'-TACAGGAAGCCTCAGCA (SEQ ID NO 44) | GGAGAGGATGTGGAGCAGAGTCTTTTCC-3' (SEQ ID NO 51) |
| TRAV6*01 | 5'-TACAGGAAGCCTCAGCA (SEQ ID NO 44) | AGCCAAAAGATAGAACAGAATTCCGAGGC-3' (SEQ ID NO 52) |
| TRAV6*03 | 5'-TACAGGAAGCCTCAGCA (SEQ ID NO 44) | GAGGCCCTGAACATTCAGGAGGG-3' (SEQ ID NO 53) |
| TRAV7*01 | 5'-TACAGGAAGCCTCAGCA (SEQ ID NO 44) | GAAAACCAGGTGGAGCACAGCCC-3' (SEQ ID NO 54) |
| TRAV8-1*01 | 5'-TACAGGAAGCCTCAGCA (SEQ ID NO 44) | GCCCAGTCTGTGAGCCAGCATAACC-3' (SEQ ID NO 55) |
| TRAV8-2*01 | 5'-TACAGGAAGCCTCAGCA (SEQ ID NO 44) | GCCCAGTCGGTGACCCAGCTTG-3' (SEQ ID NO 56) |
| TRAV8-2*02 | 5'-TACAGGAAGCCTCAGCA (SEQ ID NO 44) | GCCCAGTCGGTGACCCAGCTTAG-3' (SEQ ID NO 57) |
| TRAV8-3*01 | 5'-TACAGGAAGCCTCAGCA (SEQ ID NO 44) | GCCCAGTCAGTGACCCAGCCTG-3' (SEQ ID NO 58) |
| TRAV8-4*06 | 5'-TACAGGAAGCCTCAGCA (SEQ ID NO 44) | CTCTTCTGGTATGTGCAATACCCCAACC-3' (SEQ ID NO 59) |
| TRAV8-4*07 | 5'-TACAGGAAGCCTCAGCA (SEQ ID NO 44) | GTTGAACCATATCTCTTCTGGTA TGTGCAATACC-3' (SEQ ID NO 60) |

TABLE 3-continued

Single cell TCRa cloning primers
Vα-gene-specific primers for cloning TCRα genes

| TRAV gene | UP3 | Vα |
|---|---|---|
| TRAV8-6*01 | 5'-TACAGGAAGCCTCAGCA (SEQ ID NO 44) | GCCCAGTCTGTGACCCAGCTTGAC-3' (SEQ ID NO 61) |
| TRAV8-7*01 | 5'-TACAGGAAGCCTCAGCA (SEQ ID NO 44) | ACCCAGTCGGTGACCCAGCTTG-3' (SEQ ID NO 62) |
| TRAV9-1*01 | 5'-TACAGGAAGCCTCAGCA (SEQ ID NO 44) | GGAGATTCAGTGGTCCAGACAGAAGGC-3' (SEQ ID NO 63) |
| TRAV9-2*01 | 5'-TACAGGAAGCCTCAGCA (SEQ ID NO 44) | GGAAATTCAGTGACCCAGATGGAAGG-3' (SEQ ID NO 64) |
| TRAV9-2*02 | 5'-TACAGGAAGCCTCAGCA (SEQ ID NO 44) | GGAGATTCAGTGACCCAGATGGAAGG-3' (SEQ ID NO 65) |
| TRAV10*01 | 5'-TACAGGAAGCCTCAGCA (SEQ ID NO 44) | AAAAACCAAGTGGAGCAGAGTCCTCAGTC-3' (SEQ ID NO 66) |
| TRAV11*01 | 5'-TACAGGAAGCCTCAGCA (SEQ ID NO 44) | CTACATACACTGGAGCAGAGTCCTTCATTCC-3' (SEQ ID NO 67) |
| TRAV12-1*01 | 5'-TACAGGAAGCCTCAGCA (SEQ ID NO 44) | CGGAAGGAGGTGGAGCAGGATCC-3' (SEQ ID NO 68) |
| TRAV12-2*01 | 5'-TACAGGAAGCCTCAGCA (SEQ ID NO 44) | CAGAAGGAGGTGGAGCAGAATTCTGG-3' (SEQ ID NO 69) |
| TRAV12-2*03 | 5'-TACAGGAAGCCTCAGCA (SEQ ID NO 44) | GGACCCCTCAGTGTTCCAGAGGG-3' (SEQ ID NO 70) |
| TRAV12-3*01 | 5'-TACAGGAAGCCTCAGCA (SEQ ID NO 44) | CAGAAGGAGGTGGAGCAGGATCCTG-3' (SEQ ID NO 71) |
| TRAV13-1*02 | 5'-TACAGGAAGCCTCAGCA (SEQ ID NO 44) | GGAGAGAATGTGGAGCAGCATCCTTC-3' (SEQ ID NO 72) |
| TRAV13-2*01 | 5'-TACAGGAAGCCTCAGCA (SEQ ID NO 44) | GGAGAGAGTGTGGGGCTGCATCTTC-3' (SEQ ID NO 73) |
| TRAV14/ DV4*01 | 5'-TACAGGAAGCCTCAGCA (SEQ ID NO 44) | GCCCAGAAGATAACTCAAACCCAACCAG-3' (SEQ ID NO 74) |
| TRAV14/ DV4*04 | 5'-TACAGGAAGCCTCAGCA (SEQ ID NO 44) | CAGAAGATAACTCAAACCCAACCAGGAATG-3' (SEQ ID NO 75) |
| TRAV16*01 | 5'-TACAGGAAGCCTCAGCA (SEQ ID NO 44) | GCCCAGAGAGTGACTCAGCCCGA-3' (SEQ ID NO 76) |
| TRAV17*01 | 5'-TACAGGAAGCCTCAGCA (SEQ ID NO 44) | AGTCAACAGGGAGAAGAGGATCCTCAGG-3' (SEQ ID NO 77) |
| TRAV18*01 | 5'-TACAGGAAGCCTCAGCA (SEQ ID NO 44) | GGAGACTCGGTTACCCAGACAGAAGG-3' (SEQ ID NO 78) |
| TRAV19*01 | 5'-TACAGGAAGCCTCAGCA (SEQ ID NO 44) | GCTCAGAAGGTAACTCAAGCGCAGACTG-3' (SEQ ID NO 79) |
| TRAV20*01 | 5'-TACAGGAAGCCTCAGCA (SEQ ID NO 44) | GAAGACCAGGTGACGCAGAGTCCC-3' (SEQ ID NO 80) |
| TRAV21*01 | 5'-TACAGGAAGCCTCAGCA (SEQ ID NO 44) | AAACAGGAGGTGACGCAGATTCCTGC-3' (SEQ ID NO 81) |
| TRAV22*01 | 5'-TACAGGAAGCCTCAGCA (SEQ ID NO 44) | GGAATACAAGTGGAGCAGAGTCCTCCAG-3' (SEQ ID NO 82) |
| TRAV23/ DV6*01 | 5'-TACAGGAAGCCTCAGCA (SEQ ID NO 44) | CAGCAGCAGGTGAAACAAAGTCCTCA-3' (SEQ ID NO 83) |
| TRAV23/ DV6*04 | 5'-TACAGGAAGCCTCAGCA (SEQ ID NO 44) | CAGCAGGTGAAACAAAGTCCTCAATCTTTG-3' (SEQ ID NO 84) |
| TRAV24*01 | 5'-TACAGGAAGCCTCAGCA (SEQ ID NO 44) | ATACTGAACGTGGAACAAAGTCCTCAGTCAC-3' (SEQ ID NO 85) |

TABLE 3-continued

Single cell TCRa cloning primers
Vα-gene-specific primers for cloning TCRα genes

| TRAV gene | UP3 | Vα |
|---|---|---|
| TRAV25*01 | 5'-TACAGGAAGCCTCAGCA (SEQ ID NO 44) | GGACAACAGGTAATGCAAATTCCTCAGTACC-3' (SEQ ID NO 86) |
| TRAV26-1*01 | 5'-TACAGGAAGCCTCAGCA (SEQ ID NO 44) | GATGCTAAGACCACCCAGCCCCC-3' (SEQ ID NO 87) |
| TRAV26-1*02 | 5'-TACAGGAAGCCTCAGCA (SEQ ID NO 44) | GATGCTAAGACCACCCAGCCCACC-3' (SEQ ID NO 88) |
| TRAV26-2*01 | 5'-TACAGGAAGCCTCAGCA (SEQ ID NO 44) | GATGCTAAGACCACACAGCCAAATTCAATG-3' (SEQ ID NO 89) |
| TRAV27*01 | 5'-TACAGGAAGCCTCAGCA (SEQ ID NO 44) | ACCCAGCTGCTGGAGCAGAGCC-3' (SEQ ID NO 90) |
| TRAV29/ DV5*01 | 5'-TACAGGAAGCCTCAGCA (SEQ ID NO 44) | GACCAGCAAGTTAAGCAAAATTCACCATC-3' (SEQ ID NO 91) |
| TRAV30*01 | 5'-TACAGGAAGCCTCAGCA (SEQ ID NO 44) | CAACAACCAGTGCAGAGTCCTCAAGC-3' (SEQ ID NO 92) |
| TRAV34*01 | 5'-TACAGGAAGCCTCAGCA (SEQ ID NO 44) | AGCCAAGAACTGGAGCAGAGTCCTCAG-3' (SEQ ID NO 93) |
| TRAV35*01 | 5'-TACAGGAAGCCTCAGCA (SEQ ID NO 44) | GGTCAACAGCTGAATCAGAGTCCTCAATC-3' (SEQ ID NO 94) |
| TRAV36/ DV7*01 | 5'-TACAGGAAGCCTCAGCA (SEQ ID NO 44) | GAAGACAAGGTGGTACAAAGCCCTCTATCTC-3' (SEQ ID NO 95) |
| TRAV36/ DV7*02 | 5'-TACAGGAAGCCTCAGCA (SEQ ID NO 44) | GAAGACAAGGTGGTACAAAGCCCTCAATC-3' (SEQ ID NO 96) |
| TRAV38-1*01 | 5'-TACAGGAAGCCTCAGCA (SEQ ID NO 44) | GCCCAGACAGTCACTCAGTCTCAACCAG-3' (SEQ ID NO 97) |
| TRAV38-1*04 | 5'-TACAGGAAGCCTCAGCA (SEQ ID NO 44) | GCCCAGACAGTCACTCAGTCCCAGC-3' (SEQ ID NO 98) |
| TRAV38-2/ DV8*01 | 5'-TACAGGAAGCCTCAGCA (SEQ ID NO 44) | GCTCAGACAGTCACTCAGTCTCAACCAGAG-3' (SEQ ID NO 99) |
| TRAV39*01 | 5'-TACAGGAAGCCTCAGCA (SEQ ID NO 44) | GAGCTGAAAGTGGAACAAAACCCTCTGTTC-3' (SEQ ID NO 100) |
| TRAV40*01 | 5'-TACAGGAAGCCTCAGCA (SEQ ID NO 44) | AGCAATTCAGTCAAGCAGACGGGC-3' (SEQ ID NO 101) |
| TRAV41*01 | 5'-TACAGGAAGCCTCAGCA (SEQ ID NO 44) | AAAAATGAAGTGGAGCAGAGTCCTCAGAAC-3' (SEQ ID NO 102) |

TABLE 4 single cell TCRβ cloning primers.
Vβ-gene-specific primers for cloning TCRα genes

| TRBV gene | UP3 | Vβ |
|---|---|---|
| TRBV1*01 | 5'-CAGGAGGGCTCGGCA (SEQ ID NO 45) | GATACTGGAATTACCCAGACACCAAAATACCTG-3' (SEQ ID NO 103) |
| TRBV2*01 | 5'-CAGGAGGGCTCGGCA (SEQ ID NO 45) | GAACCTGAAGTCACCCAGACTCCCAG-3' (SEQ ID NO 104) |
| TRBV3-1*01 | 5'-CAGGAGGGCTCGGCA (SEQ ID NO 45) | GACACAGCTGTTTCCCAGACTCCAAAATAC-3' (SEQ ID NO 105) |

TABLE 4-continued single cell TCRP cloning primers.
Vβ-gene-specific primers for cloning TCRα genes

| TRBV gene | UP3 | Vβ |
|---|---|---|
| TRBV3-2*01 | 5'-CAGGAGGGCTCGGCA (SEQ ID NO 45) | GACACAGCCGTTTCCCAGACTCCA-3' (SEQ ID NO 106) |
| TRBV4-1*01 | 5'-CAGGAGGGCTCGGCA (SEQ ID NO 45) | GACACTGAAGTTACCCAGACACCAAAACAC-3' (SEQ ID NO 107) |
| TRBV4-1*02 | 5'-CAGGAGGGCTCGGCA (SEQ ID NO 45) | CACCTGGTCATGGGAATGACAAATAAGAAG-3' (SEQ ID NO 108) |
| TRBV4-2*01 | 5'-CAGGAGGGCTCGGCA (SEQ ID NO 45) | GAAACGGGAGTTACGCAGACACCAAG-3' (SEQ ID NO 109) |
| TRBV4-3*04 | 5'-CAGGAGGGCTCGGCA (SEQ ID NO 45) | AAGAAGTCTTTGAAATGTGAACAACATCTGGG-3' (SEQ ID NO 110) |
| TRBV5-1*01 | 5'-CAGGAGGGCTCGGCA (SEQ ID NO 45) | AAGGCTGGAGTCACTCAAACTCCAAGATATC-3' (SEQ ID NO 111) |
| TRBV5-1*02 | 5'-CAGGAGGGCTCGGCA (SEQ ID NO 45) | AGGGCTGGGGTCACTCAAACTCC-3' (SEQ ID NO 112) |
| TRBV5-3*01 | 5'-CAGGAGGGCTCGGCA (SEQ ID NO 45) | GAGGCTGGAGTCACCCAAAGTCCC-3' (SEQ ID NO 113) |
| TRBV5-4*01 | 5'-CAGGAGGGCTCGGCA (SEQ ID NO 45) | GAGACTGGAGTCACCCAAAGTCCCAC-3' (SEQ ID NO 114) |
| TRBV5-4*03 | 5'-CAGGAGGGCTCGGCA (SEQ ID NO 45) | CAGCAAGTGACACTGAGATGCTCTTCTCAG-3' (SEQ ID NO 115) |
| TRBV5-4*04 | 5'-CAGGAGGGCTCGGCA (SEQ ID NO 45) | ACTGTGTCCTGGTACCAACAGGCCCT-3' (SEQ ID NO 116) |
| TRBV5-5*01 | 5'-CAGGAGGGCTCGGCA (SEQ ID NO 45) | GACGCTGGAGTCACCCAAAGTCC-3' (SEQ ID NO 117) |
| TRBV5-8*01 | 5'-CAGGAGGGCTCGGCA (SEQ ID NO 45) | GAGGCTGGAGTCACACAAAGTCCCAC-3' (SEQ ID NO 118) |
| TRBV5-8*02 | 5'-CAGGAGGGCTCGGCA (SEQ ID NO 45) | AGGACAGCAAGCGACTCTGAGATGC-3' (SEQ ID NO 119) |
| TRBV6-1*01 | 5'-CAGGAGGGCTCGGCA (SEQ ID NO 45) | AATGCTGGTGTCACTCAGACCCCA-3' (SEQ ID NO 120) |
| TRBV6-4*01 | 5'-CAGGAGGGCTCGGCA (SEQ ID NO 45) | ATTGCTGGGATCACCCAGGCAC-3' (SEQ ID NO 121) |
| TRBV6-4*02 | 5'-CAGGAGGGCTCGGCA (SEQ ID NO 45) | ACTGCTGGGATCACCCAGGCAC-3' (SEQ ID NO 122) |
| TRBV7-1*01 | 5'-CAGGAGGGCTCGGCA (SEQ ID NO 45) | GGTGCTGGAGTCTCCCAGTCCCTG-3' (SEQ ID NO 123) |

TABLE 4-continued single cell TCRP cloning primers.
Vβ-gene-specific primers for cloning TCRα genes

| TRBV gene | UP3 | Vβ |
|---|---|---|
| TRBV7-2*01 | 5'-CAGGAGGGCTCGGCA (SEQ ID NO 45) | GGAGCTGGAGTCTCCCAGTCCCC-3' (SEQ ID NO 124) |
| TRBV7-2*04 | 5'-CAGGAGGGCTCGGCA (SEQ ID NO 45) | GGAGCTGGAGTTTCCCAGTCCCC-3' (SEQ ID NO 125) |
| TRBV7-3*01 | 5'-CAGGAGGGCTCGGCA (SEQ ID NO 45) | GGTGCTGGAGTCTCCCAGACCC-3' (SEQ ID NO 126) |
| TRBV7-3*05 | 5'-CAGGAGGGCTCGGCA (SEQ ID NO 45) | TGGGAGCTCAGGTGTGATCCAATTTC-3' (SEQ ID NO 127) |
| TRBV7-4*01 | 5'-CAGGAGGGCTCGGCA (SEQ ID NO 45) | GGTGCTGGAGTCTCCCAGTCCC-3' (SEQ ID NO 128) |
| TRBV7-6*01 | 5'-CAGGAGGGCTCGGCA (SEQ ID NO 45) | GGTGCTGGAGTCTCCCAGTCTCCC-3' (SEQ ID NO 129) |
| TRBV7-9*01 | 5'-CAGGAGGGCTCGGCA (SEQ ID NO 45) | GATACTGGAGTCTCCCAGAACCCCAG-3' (SEQ ID NO 130) |
| TRBV7-9*03 | 5'-CAGGAGGGCTCGGCA (SEQ ID NO 45) | GATACTGGAGTCTCCCAGGACCCCAG-3' (SEQ ID NO 131) |
| TRBV7-9*04 | 5'-CAGGAGGGCTCGGCA (SEQ ID NO 45) | ATATCTGGAGTCTCCCACAACCCCAGAC-3' (SEQ ID NO 132) |
| TRBV7-9*07 | 5'-CAGGAGGGCTCGGCA (SEQ ID NO 45) | CACAACCGCCTTTATTGGTACCGACAG-3' (SEQ ID NO 133) |
| TRBV9*01 | 5'-CAGGAGGGCTCGGCA (SEQ ID NO 45) | GATTCTGGAGTCACACAAACCCCAAAGC-3' (SEQ ID NO 134) |
| TRBV10-1*01 | 5'-CAGGAGGGCTCGGCA (SEQ ID NO 45) | GATGCTGAAATCACCCAGAGCCCAAG-3' (SEQ ID NO 135) |
| TRBV10-2*01 | 5'-CAGGAGGGCTCGGCA (SEQ ID NO 45) | GATGCTGGAATCACCCAGAGCCCA-3' (SEQ ID NO 136) |
| TRBV10-2*02 | 5'-CAGGAGGGCTCGGCA (SEQ ID NO 45) | AAGGCAGGTGACCTTGATGTGTCACC-3' (SEQ ID NO 137) |
| TRBV11-1*01 | 5'-CAGGAGGGCTCGGCA (SEQ ID NO 45) | GAAGCTGAAGTTGCCCAGTCCCC-3' (SEQ ID NO 138) |
| TRBV11-2*01 | 5'-CAGGAGGGCTCGGCA (SEQ ID NO 45) | GAAGCTGGAGTTGCCCAGTCTCCCAG-3' (SEQ ID NO 139) |
| TRBV11-3*01 | 5'-CAGGAGGGCTCGGCA (SEQ ID NO 45) | GAAGCTGGAGTGGTTCAGTCTCCCAGA-3' (SEQ ID NO 140) |
| TRBV11-3*03 | 5'-CAGGAGGGCTCGGCA (SEQ ID NO 45) | GGTCTCCCAGATATAAGATTATAGAGAAGAAACAGC-3' (SEQ ID NO 141) |

TABLE 4-continued single cell TCRP cloning primers.
Vβ-gene-specific primers for cloning TCRα genes

| TRBV gene | UP3 | Vβ |
|---|---|---|
| TRBV12-1*01 | 5'-CAGGAGGGCTCGGCA (SEQ ID NO 45) | GATGCTGGTGTTATCCAGTCACCCAGG-3' (SEQ ID NO 142) |
| TRBV12-2*01 | 5'-CAGGAGGGCTCGGCA (SEQ ID NO 45) | GATGCTGGCATTATCCAGTCACCCAAG-3' (SEQ ID NO 143) |
| TRBV12-3*01 | 5'-CAGGAGGGCTCGGCA (SEQ ID NO 45) | GATGCTGGAGTTATCCAGTCACCCC-3' (SEQ ID NO 144) |
| TRBV12-5*01 | 5'-CAGGAGGGCTCGGCA (SEQ ID NO 45) | GATGCTAGAGTCACCCAGACACCAAGG-3' (SEQ ID NO 145) |
| TRBV13*01 | 5'-CAGGAGGGCTCGGCA (SEQ ID NO 45) | GCTGCTGGAGTCATCCAGTCCCC-3' (SEQ ID NO 146) |
| TRBV14*01 | 5'-CAGGAGGGCTCGGCA (SEQ ID NO 45) | GAAGCTGGAGTTACTCAGTTCCCCAGC-3' (SEQ ID NO 147) |
| TRBV15*01 | 5'-CAGGAGGGCTCGGCA (SEQ ID NO 45) | GATGCCATGGTCATCCAGAACCCAAG-3' (SEQ ID NO 148) |
| TRBV16*01 | 5'-CAGGAGGGCTCGGCA (SEQ ID NO 45) | GGTGAAGAAGTCGCCCAGACTCCA-3' (SEQ ID NO 149) |
| TRBV17*01 | 5'-CAGGAGGGCTCGGCA (SEQ ID NO 45) | GAGCCTGGAGTCAGCCAGACCC-3' (SEQ ID NO 150) |
| TRBV18*01 | 5'-CAGGAGGGCTCGGCA (SEQ ID NO 45) | AATGCCGGCGTCATGCAGAAC-3' (SEQ ID NO 151) |
| TRBV19*01 | 5'-CAGGAGGGCTCGGCA (SEQ ID NO 45) | GATGGTGGAATCACTCAGTCCCCAAAG-3' (SEQ ID NO 152) |
| TRBV20-1*01 | 5'-CAGGAGGGCTCGGCA (SEQ ID NO 45) | GGTGCTGTCGTCTCTCAACATCCGAG-3' (SEQ ID NO 153) |
| TRBV20/OR9-2*01 | 5'-CAGGAGGGCTCGGCA (SEQ ID NO 45) | AGTGCTGTCGTCTCTCAACATCCGAG-3' (SEQ ID NO 154) |
| TRBV21-1*01 | 5'-CAGGAGGGCTCGGCA (SEQ ID NO 45) | GACACCAAGGTCACCCAGAGACCTAGAC-3' (SEQ ID NO 155) |
| TRBV21/OR9-2*01 | 5'-CAGGAGGGCTCGGCA (SEQ ID NO 45) | GACACCAAGGTCACCCAGAGACCTAGATTTC-3' (SEQ ID NO 156) |
| TRBV23-1*01 | 5'-CAGGAGGGCTCGGCA (SEQ ID NO 45) | CATGCCAAAGTCACACAGACTCCAGG-3' (SEQ ID NO 157) |
| TRBV24-1*01 | 5'-CAGGAGGGCTCGGCA (SEQ ID NO 45) | GATGCTGATGTTACCCAGACCCCAAG-3' (SEQ ID NO 158) |
| TRBV25-1*01 | 5'-CAGGAGGGCTCGGCA (SEQ ID NO 45) | GAAGCTGACATCTACCAGACCCCAAGATAC-3' (SEQ ID NO 159) |

TABLE 4-continued single cell TCRP cloning primers.
Vβ-gene-specific primers for cloning TCRα genes

| TRBV gene | UP3 | Vβ |
|---|---|---|
| TRBV26*01 | 5'-CAGGAGGGCTCGGCA (SEQ ID NO 45) | GATGCTGTAGTTACACAATTCCCAAGACACAG-3' (SEQ ID NO 160) |
| TRBV26/OR9-2*01 | 5'-CAGGAGGGCTCGGCA (SEQ ID NO 45) | GATGCTGTAGTTACACAATTCTCAAGACACAGAATC-3' (SEQ ID NO 161) |
| TRBV27*01 | 5'-CAGGAGGGCTCGGCA (SEQ ID NO 45) | GAAGCCCAAGTGACCCAGAACCC-3' (SEQ ID NO 162) |
| TRBV28*01 | 5'-CAGGAGGGCTCGGCA (SEQ ID NO 45) | GATGTGAAAGTAACCCAGAGCTCGAGATATC-3' (SEQ ID NO 163) |
| TRBV29-1*01 | 5'-CAGGAGGGCTCGGCA (SEQ ID NO 45) | AGTGCTGTCATCTCTCAAAAGCCAAGC-3' (SEQ ID NO 164) |
| TRBV29-1*03 | 5'-CAGGAGGGCTCGGCA (SEQ ID NO 45) | ACGATCCAGTGTCAAGTCGATAGCCAAG-3' (SEQ ID NO 165) |
| TRBV30*01 | 5'-CAGGAGGGCTCGGCA (SEQ ID NO 45) | TCTCAGACTATTCATCAATGGCCAGCG-3' (SEQ ID NO 166) |
| TRBV30*04 | 5'-CAGGAGGGCTCGGCA (SEQ ID NO 45) | ACTATTCATCAATGGCCAGCGACCC-3' (SEQ ID NO 167) |

Example 7: Further DNA Amplification Following RT-PCR

Figure 6A:
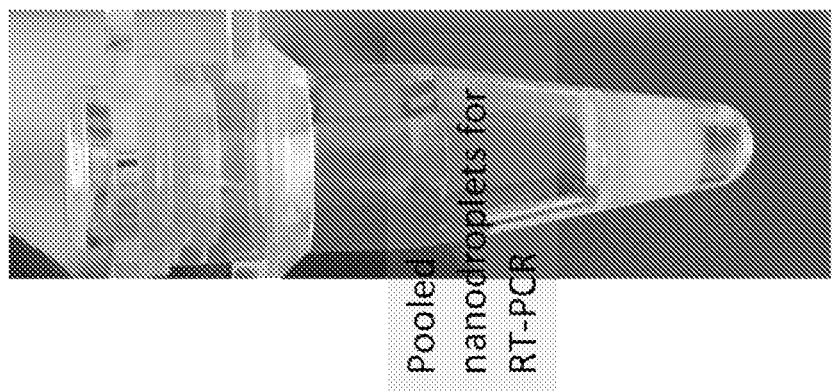
FIG. 6A shows an example of droplets collected in a collection container.
Figure 6B:
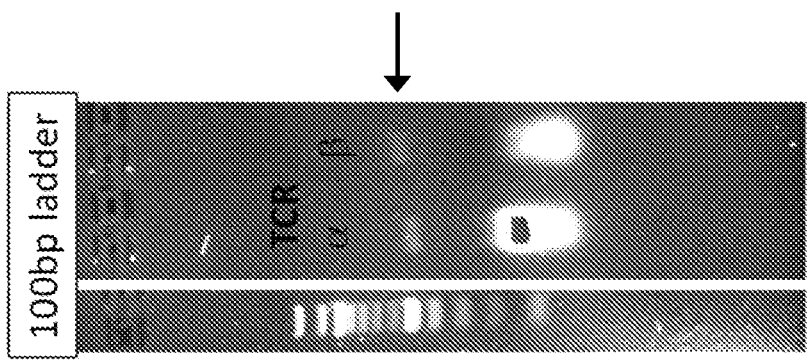
FIG. 6B shows specific amplification of TCRα and TCRβ transcripts.

Following RT-PCR, amplified DNA products were extracted from the droplets. In detail, 1 volume of 50% PFO (perfluorooctanol) solution in HFE-7500 was added to the droplets, vortexed, and spun down at about 1000 g for 2 min. The supernatant was recovered for subsequent PCR. A series of additional primers designed to amplify the DNA products UP1-NI—Cα-Vα-UP3 and UP1-NI—Cβ-Vβ-UP3 were added to the extracted supernatant (Table 5). The primers used for PCR are listed in Table 5. In a first amplification round, PS-2, Seq2-Vα, and Seq2-Vβ were designed to anneal to UP1 and UP3/Vα and UP3/Vβ, respectively. In a second amplification round, UP2-UP1 was designed to anneal to UP1 and attach an i5 Illumina sequencing adaptor (i.e., "UP2"), and UP4-UP3 was designed to anneal to UP3 for both TCRα and TCRβ, and attach an i7 Illumina sequencing adaptor (i.e., "UP2"). The amplified product was analyzed by gel electrophoresis for confirmatory purposes, an example of which is shown in FIG. 6B. The TCR DNA can be recovered from the gel and used for next generation sequencing.

TABLE 5

Primers for PCR

| | Sequence |
|---|---|
| 2nd step PCR primers | |
| PS-2 | 5'TCGTCGGCAGCGTCAGATG (SEQ ID NO 168) |
| Seq2-Va | 5'GTCTCGTGGGCTCGGAGATGTGTATAAGAGACAGTACAGGAAGCCTCAGCA (SEQ ID NO 169) |
| Seq2-Vb | 5'GTCTCGTGGGCTCGGAGATGTGTATAAGAGACAGCAGGAGGGCTCGGCA (SEQ ID NO 170) |
| 3rd step PCR primers | |
| UP2-UP1 | 5'-*AATGATACGGCGACCACCGAGATCTACAC*TCGTCGGCAGCGTCAGATGTGTATAAGAGACAG (SEQ ID NO 171) Bold italic denotes Illumina i5 sequencing adaptor |
| UP3-UP4 | 5'-*CAAGCAGAAGACGGCATACGAGAT*GTCTCGTGGGCTCGGAGATGTGTATAAGAGACAG (SEQ ID NO 172) Bold italic denotes Illumina i7 sequencing adaptor |

Example 8: Identification of Antigen-Specific TCRα and TCRβ Sequences in Primary T Cells Barcoded NP-antigen-MHC complexes, described above, were successfully used to identify antigen-specific paired TCRα and TCRβ sequences from a patient sample comprising antigen-specific T cells. CMV reactive T cells from PBMCs were mixed with a barcoded library containing barcoded NP-antigen-MHC complexes displaying a selected CMV antigen (NLVPMVATV [SEQ ID NO: 11]). In addition, the library contained three additional barcoded NP-antigen-MHC complexes displaying antigenic peptides not recognized CMV reactive T cells (MHC-J-KILGFVFJV SEQ ID NO: 12; Mart-1-ELAGIGILTV SEQ ID NO: 13; and EBV-GLCTLVAML SEQ ID NO: 14). As shown in Table 6, each NI was uniquely associated with the identity of each corresponding antigen. Following isolation of the NP-antigen-MHC complexes, single-cell droplets each containing a single barcoded T cell were generated using the above described DLD microfluidic device. Next, the RT-PCR reaction and PCR amplification steps described above were performed. After gel purification, the amplified UP2-UP1-NI—Cα-Vα-UP3-UP4 and UP2-UP1-NI—Cβ—Vβ-UP3-UP4 products representing the TCRα and TCRβ genes expressed in single T cells, respectively, were sent out for sequencing by a third party vendor. The sequencing was carried out in an Illumina Miseq machine using a 2×150 kit. Since the antisense primers were designed to anneal near the junction of the constant region and variable region of the TCRα and TCRβ genes, 150 base reads covering the CDR3 region, typically the most variable region in TCR genes, were generated.

Following sequencing analysis, TCRα and TCRβ sequences containing the CMV specific NI barcode "ACTCTT" were identified, demonstrating the efficiency of the separation and isolation methods used to generate the single cell droplets. As shown in Table 7, the majority of sequences represented a single TCRα and TCRβ sequence. Thus, sequencing identified a pair of TCRα and TCRβ sequences specific for the CMV antigen, specifically, the CDR3 amino acid sequences representing the TRAV16 TCRα gene (CASSTVSGAPSEQFF, SEQ ID NO: 15) and the TRBV6-5 TCRβ gene (CALYFFFGNEKLTF, SEQ ID NO: 16). In addition, the sequencing likely identified an unproductively rearranged TCRα gene TRAV4. The results demonstrate that sequencing using the barcoded NP-antigen-MHC complexes successfully identified antigen-specific paired TCRα and TCRβ sequences. Thus, the methods and compositions can be used to uniquely match a given MHC-antigen pair to a particular antigen-specific T cell via its TCR sequences.

TABLE 6

Barcoded Polynucleotides for Unique Antigens

| Name | DNA sequence (NI barcodes unique for each antigen denoted as bold italic) |
|---|---|
| UP1-NI1-Cα CMV | /5PCBio/TCGTCGGCAGCGTCAG ATGTGTATAAGAGACAGNNNNNNN N*ACTCTT*GATGGCTCAAACACAGC GACCTC (SEQ ID NO: 17) |
| UP1-NI1-Cβ CMV | /5PCBio/TCGTCGGCAGCGTCAGA TGTGTATAAGAGACAGNNNNNNNN *ACTCTT*TCTCTCAGCTGGTACACG GC (SEQ ID NO: 18) |
| UP1-NI2-Cα MHC-J | /5PCBio/TCGTCGGCAGCGTCAGA TGTGTATAAGAGACAGNNNNNNNN N*CGAGTC*TCTCTCAGCTGGTACA CGGC (SEQ ID NO: 19) |
| UP1-NI2-Cβ MHC-J | /5PCBio/TCGTCGGCAGCGTCAGA TGTGTATAAGAGACAGNNNNNNNN N*CGAGTC*GATGGCTCAAACACAGC GACCTC (SEQ ID NO: 20) |
| UP1-NI3-Cα Mart-1 | /5PCBio/TCGTCGGCAGCGTCAGA TGTGTATAAGAGACAGNNNNNNNN N*TAGACG*TCTCTCAGCTGGTACAC GGC (SEQ ID NO: 21) |
| UP1-NI3-Cβ Mart-1 | /5PCBio/TCGTCGGCAGCGTCAGA TGTGTATAAGAGACAGNNNNNNNN N*TAGACG*GATGGCTCAAACACAGC GACCTC (SEQ ID NO: 22) |
| UP1-NI4-Cα EBV | /5PCBio/TCGTCGGCAGCGTCAGA TGTGTATAAGAGACAGNNNNNNNN N*TTCAGG*TCTCTCAGCTGGTACAC GGC (SEQ ID NO: 23) |
| UP1-NI4-Cβ EBV | /5PCBio/TCGTCGGCAGCGTCAGA TGTGTATAAGAGACAGNNNNNNNN N*TTCAGG*GGATGGCTCAAACACAG CGACCTC (SEQ ID NO: 24) |

TABLE 7

Sequencing analysis of CMV specific T cells

| No | Total read | UMI | CDR3 amino acid sequence | TCR V gene |
|---|---|---|---|---|
| 1 | 3441655 | 394 | CASSTVSGAPSEQFF (SEQ ID NO: 15) | TRBV6-5 |
| 2 | 2282256 | 208 | CALYFFFGNEKLTF (SEQ ID NO: 16) | TRAV16 |
| 3 | 520852 | 48 | CLE*IME~SQGNLIF (SEQ ID NO: 25) | TRAV4 |
| 4 | 93517 | 7 | CAVEYGNQFYF (SEQ ID NO: 26) | TRAV3 |
| 5 | 41 | 1 | CLE*IMEEAKE~LIFGNEKLTF (SEQ ID NOS: 27 and 173) | TRAV4 |
| 6 | 34 | 1 | CASSTGAGAPSEQFV (SEQ ID NO: 28) | TRBV6-5 |
| 7 | 25 | 1 | CIVRVASSGGATNKLIF (SEQ ID NO: 29) | TRAV26-1 |
| 8 | 23 | 1 | CAYRSALNDKIIF (SEQ ID NO: 30) | TRAV38-2DV8 |
| 9 | 22 | 1 | CALYFFF (SEQ ID NO: 31) | TRAV16 |
| 10 | 19 | 1 | CASSTVSGAPSEQGV (SEQ ID NO: 32) | TRBV6-5 |
| 11 | 18 | 1 | CASSFSPPDGISYEQYF (SEQ ID NO: 33) | TRBV7-2 |

TABLE 7-continued

Sequencing analysis of CMV specific T cells

| No | Total read | UMI | CDR3 amino acid sequence | TCR V gene |
|---|---|---|---|---|
| 13 | 17 | 1 | CLVGDGNQAGTALIF (SEQ ID NO: 34) | TRAV4 |
| 14 | 17 | 1 | CLE*IME~QGNLIF (SEQ ID NO: 35) | TRAV4 |
| 12 | 17 | 1 | CASSTVSGAPSEQGV (SEQ ID NO: 36) | TRBV6-5 |
| 16 | 15 | 1 | CVVV*QH~TGKLIF (SEQ ID NOS: 37 and 174) | TRAV10 |
| 15 | 15 | 1 | CAHTASGTYKYIF (SEQ ID NO: 38) | TRAV38-1 |
| 17 | 15 | 1 | CAAQDRGSEQFF (SEQ ID NO: 39) | TRBV10-3 |
| 18 | 14 | 1 | CIVRDRMDSNYQLIW (SEQ ID NO: 40) | TRAV26-1 |
| 19 | 13 | 1 | CASSWVAGEGSEQFF (SEQ ID NO: 41) | TRBV7-2 |
| 20 | 12 | 1 | CVVSAGGTSYGKLTF (SEQ ID NO: 42) | TRAV12-1 |

Example 9: Identification of TCR Sequences Specific for Neoantigens

The above methods are used to identify neo-antigen specific TCR sequences. Specifically, a library containing barcoded NP-antigen-MHC complexes displaying potential neoantigens is prepared, with each antigen associated with a unique barcode ("NI"). For identification of a patient's putative neoantigens (tumor or pathogen), in silico predictive algorithmic programs are utilized that analyze the tumor, viral, or bacterial sequencing data, including whole genome, whole exome, or transcriptome sequencing data, to identify somatic mutations corresponding to putatively expressed neoantigens. Additionally, human leukocyte antigen (HLA) typing can be determined from a tumor or blood sample of the patient, and this HLA information can be utilized together with the identified putative neoantigen peptide sequences in a predictive algorithm for MHC binding, as verified by Fritsch et al., 2014, *Cancer Immunol Res.*, 2:522-529, the entire contents of which are herein incorporated by reference. Additional examples of methods to identify neoantigens include combining sequencing with mass-spectrometry and MHC presentation prediction (e.g., US Publication No. 2017/0199961), and combining sequencing with MHC binding affinity prediction (e.g., issued U.S. Pat. No. 9,115,402). In addition, methods useful for identifying whether neoantigen specific T cells are present in a patient sample can be used in combination with the methods described here, e.g., as described in US Publication No. 2017/0003288 and PCT/US17/59598, herein incorporated by reference in their entirety. These analyses result in a ranked list of the patient's candidate neoantigen peptides which can be readily synthesized using routine methods for screening of cognate antigen-specific T cells.

Once the neoantigen list is generated, the candidate peptides are synthesized and of a library of barcoded NP-antigen-MHC complexes displaying the candidate neoantigen peptides is produced. The library is mixed with patient samples containing potential neoantigen-specific T cells. Barcoded T cells are separated and isolated, and cDNA libraries are generated and sequenced, e.g., as described above. The sequences are analyzed, and paired neoantigen-specific TCRα and TCRβ sequences are identified.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The invention claimed is:

1. A composition comprising:
   a) a major histocompatibility complex (MHC) display moiety comprising at least one antigenic peptide;
   b) a first single-stranded polynucleotide sequence comprising in a 5' to 3' orientation:
      1) a first universal target sequence;
      2) a unique, defined barcode sequence, wherein the defined barcode sequence is operably associated with the identity of the antigenic peptide; and
      3) a T cell receptor (TCR) a primer sequence, wherein the TCRα primer sequence is complementary to a TCRα RNA transcript; and
   c) a second single-stranded polynucleotide sequence comprising in a 5' to 3' orientation:
      1) the first universal target sequence;
      2) the defined barcode sequence; and
      3) a TCRβ primer sequence, wherein the TCRβ primer sequence is complementary to a TCRβ RNA transcript; and
   d) a first particle; and wherein the MHC display moiety, the first single-stranded polynucleotide sequence, and the second single-stranded polynucleotide sequence are independently attached to the first particle.

2. A composition comprising:
   a) an MHC display moiety comprising:
      a streptavidin core bound to four copies of a biotinylated MHC; and
      four copies of at least one antigenic peptide, wherein the at least one antigenic peptide is a neoantigen, wherein each copy is independently bound to one of the biotinylated MHCs; and
      a first polynucleotide hybridization domain;
   b) a first single-stranded polynucleotide sequence comprising in a 5' to 3' orientation:
      1) a biotin; and
      2) a photocleaveable group;
      3) a first universal target sequence;
      4) a unique, defined barcode sequence, wherein the defined barcode sequence is operably associated with the identity of the neoantigen; and 5) a T cell receptor (TCR) a primer sequence, wherein the TCRα primer sequence is complementary to a TCRα RNA transcript; and
c) a second single-stranded polynucleotide sequence comprising in a 5' to 3' orientation:
1) a biotin;
2) a photocleaveable group;
3) the first universal target sequence;
4) the defined barcode sequence; and
5) a TCRβ primer sequence, wherein the TCRβ primer sequence is complementary to a TCRβ RNA transcript; and
d) a first particle that is a magnetic nanoparticle comprising:
streptavidin; and
a second polynucleotide hybridization domain complementary to the first polynucleotide hybridization domain,
wherein the MHC display moiety is attached to the at least one-magnetic nanoparticle by hybridization of the first and the second polynucleotide hybridization domains, and
wherein the first and the second single-stranded polynucleotide sequence are independently attached to the magnetic nanoparticle through a biotin-streptavidin interaction.

3. The composition of claim 1 or 2, wherein the first universal target sequence is a polymerase chain reaction (PCR) primer target sequence.

4. The composition of claim 1, wherein the first particle is selected from the group consisting of: a surface, a nanoparticle, a bead, and a polymer.

5. The composition of claim 4, wherein the nanoparticle is a magnetic nanoparticle or a polystyrene nanoparticle.

6. The composition of claim 2 or 5, wherein the magnetic nanoparticle comprises magnetic iron oxide.

7. The composition of claim 4, wherein the first particle is the bead that is an agarose bead.

8. The composition of claim 1 or 2, further comprising a fluorophore.

9. The composition of claim 8, wherein the fluorophore is attached, with or without a linker, to the first particle.

10. The composition of claim 1, wherein the first and the second single-stranded polynucleotide sequences are each independently and directly attached to the first particle.

11. The composition of claim 10, wherein the first and the second single-stranded polynucleotide sequences each further comprise a cleavage moiety positioned between the first particle and the respective sequence.

12. The composition of claim 11, wherein the cleavage moiety comprises a photocleavable group.

13. The composition of claim 2 or 12, wherein the photocleavable group is cleavable by UV-light.

14. The composition of claim 2 or 12, wherein the photocleavable group comprises the formula:

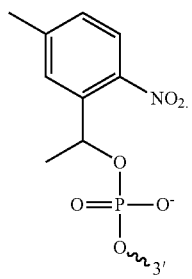

15. The composition of claim 1, wherein the MHC display moiety is directly attached to the first particle.

16. The composition of claim 1, wherein the first particle further comprises a first polynucleotide hybridization domain and the MHC display moiety further comprises a second polynucleotide hybridization domain.

17. The composition of claim 16, wherein the first polynucleotide hybridization domain comprises the nucleotide sequence CTGAATCCTCGGGATGCCTA (SEQ ID NO: 8) and the second polynucleotide hybridization domain comprises the reverse complement TAGGCATCCCGAGGATTCAG (SEQ ID NO: 9).

18. The composition of claim 16 or 17, wherein the MHC display moiety is attached to the first particle by hybridization of the first polynucleotide hybridization domain to the second polynucleotide hybridization domain.

19. The composition of claim 1, wherein the first and the second single-stranded polynucleotide sequences further comprise an attachment moiety, and the first particle further comprises a complementary attachment moiety.

20. The composition of claim 19, wherein the attachment moiety comprises biotin and the complementary attachment moiety comprises streptavidin, and wherein the first and the second single-stranded polynucleotide sequences are attached to the first particle through a biotin-streptavidin interaction.

21. The composition of claim 20, wherein the streptavidin is a cysteine-modified streptavidin.

22. The composition of claim 19, wherein the attachment moiety further comprises a fluorophore.

23. The composition of claim 19, further comprising a cleavage moiety positioned between the attachment moiety and the first single-stranded polynucleotide sequence.

24. The composition of claim 19, further comprising a cleavage moiety positioned between the attachment moiety and the second single-stranded polynucleotide sequence.

25. The composition of claim 1 or 2, wherein the at least one antigenic peptide is selected from the group consisting of: a tumor antigen, a viral antigen, a phosphoantigen, a bacterial antigen, a microbial antigen, and combinations thereof.

26. The composition of claim 1, wherein the at least one antigenic peptide is a neoantigen.

27. The composition of claim 2 or 26, wherein the neoantigen is selected by analyzing tumor, viral, or bacterial sequencing data from a subject to identify one or more somatic mutations.

28. The composition of claim 27, wherein the analyzing is performed using an in silico predictive algorithm.

29. The composition of claim 28, wherein the predictive algorithm comprises an MHC binding algorithm to predict binding between the neoantigen and a MHC allele of the subject.

30. The composition of claim 29, wherein the MHC display moiety is the MHC allele of the subject.

31. The composition of claim 1 or 2, wherein the MHC display moiety comprises a mammalian MHC.

32. The composition of claim 31, wherein the mammalian MHC comprises a human MHC.

33. The composition of claim 31, wherein the mammalian MHC comprises a MHC class I molecule.

34. The composition of claim 33, wherein the MHC class I molecule comprises a MHC molecule selected from the group consisting of: HLA-A, HLA-B, and HLA-C.

35. The composition of claim 33, wherein the at least one antigenic peptide is 7-15, 7-10, 8-9, 7, 8, 9, 10, 11, 12, 13, 14, or 15 amino acids in length.

36. The composition of claim 33, wherein the at least one antigenic peptide is between 8-10 amino acids in length.

37. The composition of claim 31, wherein the mammalian MHC comprises a MHC class II molecule.

38. The composition of claim 37, wherein the MHC class II molecule comprises an MHC molecule selected from the group consisting of: HLA-DQ and HLA-DR.

39. The composition of claim 37, wherein the at least one antigenic peptide is 11-30, 14-20, 15-18, 11, 12, 13, 14, 15, 16, 17, 18, 19, 20, 21, 22, 23, 24, 25, 26, 27, 28, 29, or 30 amino acids in length.

40. The composition of claim 37, wherein the at least one antigenic peptide is between 10 and 35, between 10 and 30, between 10 and 25, or between 10 and 20 amino acids in length.

41. The composition of claim 1, wherein the MHC display moiety comprises a multimerized MHC.

42. The composition of claim 41, wherein the multimerized MHC comprises a streptavidin core bound to multiple MHCs.

43. The composition of claim 42, wherein the streptavidin core further comprises a fluorescent molecule.

44. The composition of claim 42, wherein the streptavidin core is bound to four copies of biotinylated MHC.

45. The composition of claim 42, wherein the streptavidin core is bound to three copies of biotinylated MHC.

46. The composition of claim 1, wherein the MHC display moiety comprises a single chain trimer MHC.

47. The composition of claim 46, wherein the single chain trimer comprises a disulfide trap.

48. The composition of claim 1 or 2, wherein the first universal target sequence is between 10-50, between 15-40, between 15-35, between 15-30, between 20-40, between 25-40, or between 30-40 nucleotides in length.

49. The composition of claim 1 or 2, wherein the first universal target sequence is between 25-35 nucleotides in length.

50. The composition of claim 1 or 2, wherein the first universal target sequence is at least 15 nucleotides in length.

51. The composition of claim 1 or 2, wherein the first universal target sequence comprises the sequence TCGTCGGCAGCGTCAGATGTGTATAAGAGACAG (SEQ ID NO: 3).

52. The composition of claim 1 or 2, wherein the defined barcode sequence is between 4-10 nucleotides in length.

53. The composition of claim 52, wherein the defined barcode sequence is 6 nucleotides in length.

54. The composition of claim 52, wherein the defined barcode sequence is 6 nucleotides in length.

55. The composition of claim 1 or 2, wherein the TCRα primer sequence and the TCRβ primer sequence are between 10-50, between 15-40, between 15-35, between 15-30, between 15-25, between 15-20, or between 10-20 nucleotides in length.

56. The composition of claim 1 or 2, wherein the TCRα RNA transcript sequence comprises a TCRα constant region sequence.

57. The composition of claim 56, wherein the TCRα primer sequence comprises the nucleotide sequence TCTCTCAGCTGGTACACGGC (SEQ ID NO: 4).

58. The composition of claim 1 or 2, wherein the TCRβ RNA transcript sequence comprises a TCRβ constant region sequence.

59. The composition of claim 58, wherein the TCRβ primer sequence comprises the nucleotide sequence GATGGCTCAAACACAGCGACCTC (SEQ ID NO: 5).

60. The composition of claim 1 or 2, wherein the TCRα RNA transcript and the TCRβ RNA transcript comprise mammalian transcripts.

61. The composition of claim 60, wherein the mammalian transcripts comprise human transcripts.

62. The composition of claim 1 or 2, wherein the first and the second single-stranded polynucleotide sequences each further comprise a random nucleotide sequence.

63. The composition of claim 62, wherein each of the random nucleotide sequences is between 6-20, between 6-15, between 6-12, between 6-10, or between 6-8 nucleotides in length.

64. The composition of claim 62, wherein each of the random nucleotides sequence is 8 nucleotides in length.

65. The composition of claim 62, wherein each of the random nucleotide sequences is positioned between the first universal target sequence and the defined barcode sequence.

66. The composition of claim 1 or 2, wherein multiple copies of the first and the second single-stranded polynucleotide sequences are attached to the first particle.

67. The composition of claim 66, wherein each of the multiple copies of the first and the second single-stranded polynucleotide sequences comprises a random nucleotide sequence, wherein each of the random sequences is unique for each of the multiple copies.

68. The composition of claim 1 or 2, wherein the first particle is further bound to a TCR, wherein the TCR specifically binds the MHC display moiety.

69. The composition of claim 68, wherein the TCR is on the surface of a T cell.

70. The composition of claim 69, wherein the T cell is selected from the group consisting of: a CTL, a CD8+ T cell, a CD4+ T cell, a primary T cell, an ex vivo cultured T cell, a tumor infiltrating T cell, and an engineered T cell.

71. The composition of claim 69, wherein the T cell is isolated from a subject.

72. The composition of claim 71, wherein the subject is known or suspected to have cancer.

73. The composition of claim 1 or 2, wherein the first particle is isolated within a droplet.

74. The composition of claim 73, wherein the droplet is a water-in-oil emulsion.

75. The composition of claim 73, wherein the droplet further comprises a lysis reagent.

76. The composition of claim 75, wherein the lysis reagent comprises a surfactant.

77. The composition of claim 76, wherein the surfactant comprises IGEPAL CA 630.

78. The composition of claim 73, wherein the droplet further comprises one or more components for reverse transcription.

79. The composition of claim 78, wherein the components for reverse transcription are selected from the group consisting of: reverse transcriptase, dNTPs, RNase inhibitors, buffering agents, chelators, DTT, and combinations thereof.

80. The composition of claim 79, wherein the reverse transcriptase comprises a RNaseH positive recombinant reverse transcriptase.

81. The composition of claim 79, wherein the final concentration of the DTT is 5 mM.

82. The composition of claim 73, wherein the droplet further comprises components for DNA PCR amplification.

83. The composition of claim 82, wherein the components for DNA PCR amplification are selected from the group consisting of: DNA polymerase, dNTPs, buffering agents, chelators, amplification primers, and combinations thereof.

84. The composition of claim 83, wherein the DNA polymerase is a recombinant *Thermococcus kodakaraensis* KOD1 DNA polymerase.

85. The composition of claim 83, wherein the amplification primers comprise a TCRα forward primer and a TCRβ forward primer.

86. The composition of claim 85, wherein the TCRα forward primer and TCRβ forward primer are designed to amplify at least a portion of a TCR complementarity determining region (CDR) 3 sequence.

87. The composition of claim 85, wherein the TCRα forward primer and TCRβ forward primer are multiplexed primers.

88. The composition of claim 87, wherein each of the TCRα multiplexed primers comprises a sequence selected from SEQ ID NOs: 46-102 that hybridizes to a TCRα variable region ("Vα"), and each of the TCRβ multiplexed primers comprises a sequence selected from SEQ ID NOs: 103-167 that hybridizes to a TCRβ variable region ("Vβ").

89. The composition of claim 73, wherein the droplet has been exposed to a releasing stimulus.

90. The composition of claim 89, wherein the releasing stimulus comprises a light stimulus.

91. The composition of claim 90, wherein the light stimulus comprises UV light.

92. The composition of claim 89, wherein the releasing stimulus comprises a releasing reagent introduced into the droplet.

93. The composition of claim 92, wherein the releasing reagent is an enzymatic or chemical reagent.

94. The composition of claim 93, wherein the releasing reagent comprises a reducing reagent.

95. The composition of claim 1 or 2, further comprising:
a) a second particle;
b) a second MHC display moiety comprising at least one second antigenic peptide, wherein the second antigenic peptide has a distinct sequence relative to the at least one antigenic peptide of claim 1 or 2;
c) a third single-stranded polynucleotide sequence, comprising in a 5' to 3' orientation:
 1) the universal target sequence;
 2) a second unique, defined barcode sequence, wherein the second defined barcode sequence is operably associated with the identity of the second antigenic peptide, and wherein the second defined barcode sequence is distinct from the defined barcode sequence of any of claim 1 or 2; and
 3) the T cell receptor (TCR) a primer sequence, and
d) a fourth single-stranded polynucleotide sequence comprising in a 5' to 3' orientation:
 1) the first universal target sequence;
 2) the second defined barcode sequence; and
 3) The TCRβ primer sequence,
wherein the second MHC display moiety, the third single-stranded polynucleotide sequence, and the fourth single-stranded polynucleotide sequence are attached to the second particle.

96. The composition of claim 95, further comprising a plurality of the first and the second particles.

97. A library comprising the composition of claim 95, wherein the library comprises greater than or equal to two distinct particles, each distinct particle comprising a unique antigen and a unique, defined barcode sequence operably associated with the identity of each unique antigen.

98. A kit comprising the composition of claim 1 or 2 and instructions for use.

99. A method of manufacturing the composition of claim 1 or 2, comprising:
(i) obtaining elements (a)-(d) of claim 1 or 2, wherein one or more of elements (a)-(c) are optionally attached to the first particle prior to obtaining elements (a)-(d); and
(ii) attaching one or more of elements (a)-(c) to the first particle.

100. The method of claim 99, wherein the at least one antigenic peptide is a cleavable peptide, and the method further comprises:
(iii) replacing the at least one antigenic peptide comprised in the MHC display moiety with another antigenic peptide of interest.

101. The method of claim 99, wherein the obtaining step comprises:
synthesizing or having synthesized one or more of elements (a)-(c).

102. A method for isolating an antigen specific T cell, the method comprising the steps of:
(i) providing the composition of claim 1 or 2;
(ii) providing a sample known or suspected to comprise one or more T cells;
(iii) contacting the composition with the sample, wherein the contacting comprises providing conditions sufficient for a single T cell to bind the MHC display moiety attached to the first particle; and
(iv) isolating the single T cell associated with the first particle.

103. The method of claim 102, wherein the isolating comprises magnetic separation when the first particle is magnetic.

104. The method of claim 103, wherein the magnetic separation comprises capturing the first particle against a wall with a magnet and removing elements not captured against the wall.

105. The method of claim 102, wherein the isolating comprises using fluorescence-activated cell sorting (FACS).

106. The method of claim 102, wherein the isolating step comprises using a microfluidic device.

107. The method of claim 106, wherein the microfluidic device comprises a flow cytometer.

108. The method of claim 106, wherein the microfluidic device comprises a deterministic lateral displacement (DLD) device.

109. The method of claim 108, wherein the DLD device that separates the single T cell associated with the first particle from unbound particles.

110. The method of claim 106, wherein the microfluidic device comprises a droplet generating device that isolates the single T cell in a droplet, and the droplet does not contain another T cell or an unbound particle.

111. The method of claim 110, wherein the droplet comprises an aqueous fluid encapsulated in an immiscible carrier fluid.

112. The method of claim 111, wherein the immiscible carrier fluid comprises an oil.

113. The method of claim 112, wherein the oil comprises a fluorinated oil.

114. The method of claim 113, wherein the fluorinated oil comprises HFE-7500.

115. The method of claim 111, wherein the immiscible carrier fluid further comprises a surfactant.

116. The method of claim 115, wherein the surfactant comprises a fluorosurfactant.

117. The method of claim 116, wherein the fluorosurfactant comprises a 5% w/w PEG-PFPE amphiphilic block copolymer.

118. The method of claim 110, wherein the method further comprises adding a lysis reagent.

119. The method of claim 118, wherein the lysis reagent is added immediately prior to isolating the single T cell in the droplet, such that the lysis reagent is contained within the droplet.

120. The method of claim 110, wherein the method further comprises adding a RNA reverse transcriptase.

121. The method of claim 120, wherein the RNA reverse transcriptase is added immediately prior to isolating the single T cell in the droplet, such that the reverse transcriptase is contained within the droplet.

122. The method of claim 120, wherein the RNA reverse transcriptase comprises a RNaseH positive recombinant reverse transcriptase.

123. The method of claim 110, wherein the method further comprises adding a DNA polymerase.

124. The method of claim 123, wherein the DNA polymerase is added immediately prior to isolating the single T cell in the droplet, such that the DNA polymerase is contained within the droplet.

125. The method of claim 123, wherein the DNA polymerase is a recombinant *Thermococcus kodakaraensis* KOD1 DNA polymerase.

126. The method of claim 110, wherein the method further comprises adding:
   a) a TCRα forward primer, the TCRα forward primer comprising a second universal target sequence and a sequence designed to hybridize to a TCRα variable region sequence;
   b) a TCRβ forward primer, the TCRβ forward primer comprising the second universal target sequence and a sequence designed to hybridize to a known TCRβ variable region sequence;
   wherein the TCRα forward primer and TCRβ forward primer are contained within the droplet.

127. The method of claim 126, wherein the TCRα forward primer and TCRβ forward primer are added immediately prior to isolating the single T cell in the droplet, such that the TCRα forward primer and TCRβ forward primer are contained within the droplet.

128. The method of claim 126, wherein the TCRα forward primer and TCRβ forward primer are designed to amplify at least a portion of a TCR complementarity determining region (CDR) 3 sequence.

129. The method of claim 126, wherein the TCRα forward primer and TCRβ forward primer comprise TCRα multiplexed primers and TCRβ multiplexed primers.

130. The method of claim 129, wherein each of the TCRα multiplexed primers comprises a sequence selected from SEQ ID NOs: 46-102 that hybridizes to a TCRα variable region ("Vα"), and each of the TCRβ multiplexed primers comprises a sequence selected from SEQ ID NOs: 103-167 that hybridizes to a TCRβ variable region ("Vβ").

131. The method of claim 110, wherein the method further comprises adding dithiothreitol (DTT).

132. The method of claim 131, wherein the DTT is added immediately prior to isolating the single T cell in the droplet, such that the DTT is contained within the droplet.

133. The method of claim 131, wherein the final concentration of the DTT is 5 mM.

134. The method of claim 110, wherein the method further comprises adding additional components for nucleic acid amplification, wherein the additional components are selected from the group consisting of: dNTPs, DNase inhibitors, RNase inhibitors, buffering agents, chelators, divalent ions, and combinations thereof.

135. The method of claim 134, wherein one or more of the additional components are added immediately prior to isolating the single T cell in the droplet such that the additional components are contained within the droplet.

136. The method of claim 110, wherein the isolating step comprises collecting the droplet.

137. The method of claim 110, wherein the isolating step comprises dispersing the droplet in tubing, followed by collecting the droplet in a collection tube.

138. The method of claim 110, wherein the droplet is 70 micrometers or less, 65 micrometers or less, 60 micrometers or less, 55 micrometers or less, or 50 micrometers or less in diameter.

139. The method of claim 110, wherein the droplet is 40-70 micrometers, 40-60 micrometers, or 50-60 micrometers in diameter.

140. The method of claim 110, wherein the droplet is about 55 micrometers in diameter.

141. The method of claim 110, wherein the droplet is 30-110 picoliters, 50-100 picoliters, 60-100 picoliters, 70-100 picoliters, 70-90 picoliters, or 75-85 picoliters in volume.

142. The method of claim 110, wherein the droplet is about 80 picoliters in volume.

143. The method of claim 102, further comprising releasing a portion of the first and a portion of the second single-stranded polynucleotide sequences from the first particle, each of the portions of the first and second single-stranded polynucleotide sequences comprising the first universal target sequence, the defined barcode sequence, and the respective TCRα or TCRβ primer sequence.

144. A method for isolating an antigen specific T cell, the method comprising the steps of:
   (i) providing the composition of claim 11;
   (ii) providing a sample known or suspected to comprise one or more T cells;
   (iii) contacting the composition with the sample, wherein the contacting comprises providing conditions sufficient for a single T cell to bind the MHC display moiety attached to the first particle;
   (iv) isolating the single T cell associated with the first particle;
   (v) releasing a portion of the first and a portion of the second single-stranded polynucleotide sequences from the first particle, each of the portions of the first and second single-stranded polynucleotide sequences comprising the first universal target sequence, the defined barcode sequence, and the respective TCRα or TCRβ primer sequence, wherein the releasing comprises cleaving the cleavage moiety.

145. The method of claim 144, wherein the cleaving comprises exposing the first particle to ultraviolet (UV) light.

146. The method of claim 144, wherein the cleaving comprises exposing the first particle to a releasing agent.

147. The method of claim 146, wherein the releasing agent comprises an enzymatic or chemical reagent.

148. The method of claim 147, wherein the chemical cleavage reagent is a reducing agent.

149. The method of claim 146, the method further comprises adding the releasing agent immediately prior to isolating the single T cell in a droplet, such that the releasing agent is contained within the droplet.

150. The method of claim 143, wherein the releasing is performed in a collection tube.

151. The method of claim 143, wherein the isolating step comprises collecting a droplet comprising the single T cell in a collection tube, and wherein the releasing is performed in tubing prior to collecting the droplet in the collection tube.

152. The method of claim 126, further comprising generating or having generated a cDNA mixture, wherein the generating comprises reverse transcription, and the cDNA mixture comprises a sequence complementary to the TCRα RNA transcript and a sequence complementary to the TCRβ RNA transcript.

153. The method of claim 152, further comprising extracting or having extracted the cDNA mixture from the droplet.

154. The method of claim 153, wherein the extracting comprises the steps of:
A) adding a de-emulsification reagent;
B) collecting an aqueous solution, wherein the aqueous solution comprises the cDNA mixture.

155. The method of claim 154, the method further comprising:
(v) contacting the resulting cDNA mixture with a forward amplification primer, the forward amplification primer comprising a third universal target sequence and a sequence capable of hybridizing to at least a portion of the first universal target sequence;
(vi) contacting the resulting cDNA mixture with a reverse amplification primer, the reverse amplification primer comprising a fourth universal target sequence and a sequence capable of hybridizing to at least a portion of the second universal target sequence; and
(vii) performing a DNA amplification to produce an amplified cDNA mixture.

156. The method of claim 155, comprising purifying the amplified cDNA mixture, wherein the purifying comprises isolating the amplified cDNA mixture on an agarose gel.

157. The method of claim 152, further comprising sequencing or having sequenced the cDNA mixture.

158. The method of claim 157, wherein the sequencing comprises next generation sequencing.

159. The method of claim 157, further comprising assigning or having assigned a paired TCRα sequence and TCR β sequence to the at least one antigenic peptide associated with the single T cell using the defined barcode sequence.

160. The method of claim 102, wherein the antigen specific T cell is selected from the group consisting of: a primary T cell, an ex vivo cultured T cell, a tumor infiltrating T cell, and an engineered T cell.

161. The method of claim 102, wherein the sample is selected from the group consisting of: blood, plasma, a peripheral blood mononuclear cell population, a tissue homogenate, a tumor homogenate, and an ex vivo T cell culture.

* * * * *